United States Patent
Shah et al.

(10) Patent No.: US 11,510,930 B2
(45) Date of Patent: *Nov. 29, 2022

(54) GATIFLOXACIN, PREDNISOLONE, AND BROMFENAC COMPOSITIONS AND METHODS

(71) Applicant: Somerset Therapeutics, LLC, Hollywood, FL (US)

(72) Inventors: Mandar V. Shah, Rockaway, NJ (US); Ilango Subramanian, Warren, NJ (US); Veerappan Subramanian, Warren, NJ (US); Aman Trehan, Somerset, NJ (US)

(73) Assignee: Somerset Therapeutics, LLC, Hollywood, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/458,529

(22) Filed: Aug. 26, 2021

(65) Prior Publication Data

US 2022/0062302 A1 Mar. 3, 2022

Related U.S. Application Data

(60) Provisional application No. 63/070,549, filed on Aug. 26, 2020.

(51) Int. Cl.
| | | |
|---|---|---|
| *A61K 31/573* | (2006.01) | |
| *A61K 9/00* | (2006.01) | |
| *A61K 31/196* | (2006.01) | |
| *A61K 31/4709* | (2006.01) | |
| *A61K 9/08* | (2006.01) | |

(52) U.S. Cl.
CPC .......... *A61K 31/573* (2013.01); *A61K 9/0048* (2013.01); *A61K 9/08* (2013.01); *A61K 31/196* (2013.01); *A61K 31/4709* (2013.01)

(58) Field of Classification Search
CPC .. A61K 31/365; A61K 31/381; A61K 31/443; A61K 31/506; A61K 31/5377; A61K 31/69; A61K 31/7048; A61K 31/706; A61P 31/16; A61P 31/18
See application file for complete search history.

(56) References Cited

U.S. PATENT DOCUMENTS

| | | |
|---|---|---|
| 4,136,177 A | 1/1979 | Lin |
| 6,331,540 B1 | 12/2001 | Bhagwati |
| 6,333,045 B1 | 12/2001 | Yasueda |
| 6,716,830 B2 | 4/2004 | Cagle |
| 8,450,311 B2 | 5/2013 | Campins et al. |
| 2009/0247543 A1 | 10/2009 | Sawa |
| 2014/0213561 A1 | 7/2014 | Rajan |
| 2015/0024996 A1 | 1/2015 | Liegner |
| 2015/0129457 A1 | 5/2015 | Flodin |
| 2015/0164882 A1 | 6/2015 | Dilzer |
| 2016/0015632 A1 | 1/2016 | Anuradha |
| 2016/0101118 A1 | 4/2016 | Fernandez |
| 2016/0175323 A1 | 6/2016 | Wiley |
| 2016/0279055 A1 | 9/2016 | Liegner |
| 2018/0318319 A1* | 11/2018 | Sampietro ............ A61K 31/137 |
| 2019/0105320 A1 | 4/2019 | Fernandez |
| 2019/0111045 A1 | 4/2019 | Wiley |
| 2021/0038592 A1 | 2/2021 | Liegner |
| 2021/0046001 A1 | 2/2021 | Liegner |

OTHER PUBLICATIONS

Al-Kinani, et al., "Ophthalmic gels: Past, present and future," Adv Drug Deliv Rev. Feb. 15, 2018;126:113-126. doi: 10.1016/j.addr.2017.12.017. Epub Dec. 27, 2017. PMID: 29288733.
ARVO Annual Meeting Abstract, "New recombinant hyaluronic acid for eye care and ophthalmic drug delivery", Jun. 2013, Investigative Ophthalmology & Visual Science Jun. 2013, vol. 54, 4327.
Gaballa, et al., "Corticosteroids in Ophthalmology: drug delivery innovations, pharmacology, clinical applications, and future perspectives", Drug Delivery Trans Res. Jun. 2021; 11(3):866-893. doi: 10.1007/s13346-020-00843.z.
Holland, et al., "Use of Topical Steroids in Conjunctivitis: A Review of the Evidence", Cornea, vol. 38, No. 8, Aug. 2019.
Koutosoviti, et al., "Recent Advances in the Excipients Used for Modified Ocular Drug Delivery", Materials 2021, 14, 4290, doi.org/10.3390/ma14154290.
Kumar, et al., "Pharmaceutical Suspensions: Patient Compliance Oral Dosage Forms", World Journal of Pharmacy and Pharmaceutical Sciences, vol. 5, Issue 12, 1471-1537.
Lynch, et al., "Hydrogel Biomaterials for Application in Ocular Drug Delivery", Frontiers in Bioengineering and Biotechnology, Mar. 20, 2020, vol. 8, Article 228, doi: 10.3389/bioe.2020.00228.
Müller-Lierheim WGK., "Why Chain Length of Hyaluronan in Eye Drops Matters." Diagnostics (Basel). 2020;10(8):511. Published Jul. 23, 2020. doi: 10.3390/diagnostics10080511.
Thompson, et al., "Pred-Moxi-Brom: The Whole is Greater Than the Sum of its Parts", Glaucoma Physician Mar. 2021.
Avelox® Label—Moxifloxacin hydrochloride tablet, film coated; Physicians Total Care, Inc. Revised: Dec. 2011.
Prednisolone Acetate Moxifloxacin; Imprimis Rx; Rev3 Jun. 2020 (Brochure).
Prednisolone Acetate Moxifloxacin Nepafenac; Imprimis Rx; Rev4 Jun. 2020 (Brochure).

(Continued)

*Primary Examiner* — Savitha M Rao
(74) *Attorney, Agent, or Firm* — Transformative Legal LLC; Len S. Smith; Denise M. Brown

(57) ABSTRACT

Provided here are new ophthalmologically suitable pharmaceutical compositions comprising an effective amount of gatifloxacin, prednisolone, and bromfenac. In aspects, the compositions are suspensions that include a suspension component comprising one or more suspension agents. In aspects, the suspension component includes an ionic suspension agent. In aspects, the composition also or alternatively comprises a non-ionic surfactant, non-ionic suspension agent, or both, or an agent that provides both functions. In aspects, such compositions further comprise an effective amount of a chelating agent/component. Further described are related compositions and methods of making and using such compositions, e.g., in the treatment of eye infections.

24 Claims, No Drawings

(56) References Cited

OTHER PUBLICATIONS

Moxifloxacin 4 mg; Imprimis; Rev5 Aug. 2020 (Brochure).
Poloxamer 407 Specification Sheet (www.signmaaldrich.com/us/en/specification-sheet/SIGMA/16758 [Aug. 26, 2021 1:40:58 PM] ).
Prednisolone Bromfenac: Imprimis, Rev.3 Jun. 2020 (Brochure).
Prednisolone Gatifloxacin Bromfenac: Imprimis, Rev. Feb. 2018 (Brochure).
Prednisolone Moxifloxacin Bromfenac: Imprimis, Rev.2 Jun. 2020 (Brochure).
Moxeza® Label Moxifloxacin Hydrochloride Solution: Alcon Laboratories, Inc. Rev. Aug. 2021.
Tobradex® ST Label tobramycin and dexamethasone ointment: Alcon Laboratories, Inc, Rev. Oct. 2020.
Vigamox® Label Moxifloxacin Hydrochloride solution drops: Alcon Laboratories, Inc, Rev. Jun. 2020.
Zymar™ Box Label Gatifloxacin Solution Drops: Allergan, Inc, Rev. Apr. 2018.
Zymaxid™ Label Gatifloxacin ophthalmic solution 0.5%: Allergan, Inc, Rev. May 2010.
Tobradex® ST Label tobramycin and dexamethasone drops: Eyevance Pharmaceuticals LLC, Rev. May 2021.
Pluronic® F127 Block Copolymer Surfactant, Technical Bulletin, BASF Corporation 2012.
Prednisolone-Bromfenac (1/0.075)% Ophthalmic Drops; Imprimis NJOF, LLC (Package label) Jan. 2018.
Prednisolone Acetate Bromfenac; Imprimis NJOF, LLC (Brochure) Jan. 2018.
Synperonic™ PE/F127 Technical Sheet, Corda Industrial Chemicals 2012.

\* cited by examiner

GATIFLOXACIN, PREDNISOLONE, AND BROMFENAC COMPOSITIONS AND METHODS

CROSS REFERENCE TO RELATED APPLICATIONS

This patent application claims priority to U.S. Provisional Patent Application No. 63/070,549, filed Aug. 26, 2020, titled, "Gatifloxacin, Prednisolone and Bromfenac Ophthalmic Composition". This application claims the benefit of priority to, and incorporates by reference the entirety of, this above-referenced priority application.

FIELD OF THE INVENTION

The invention relates to compositions or methods for the treatment ophthalmological conditions, such as bacterial infections of the eye.

BACKGROUND OF THE INVENTION

It is estimated that 80% of what a typical human perceives comes through the sense of sight. Accordingly, humans place a remarkable value on vision. In fact, reportedly 88% of participants in one study ranked vision as their most valued sense.

According to the American Academy of Ophthalmology, "Visual impairment is a . . . national health concern that has a negative impact on physical and mental health." Unfortunately, there are a number of medical conditions that threaten good eye health. For example, WebMD describes 19 "common" eye ailments. Some of these conditions, like glaucoma, impact millions of people per year. For example, conjunctivitis of the eye (e.g., pink eye), which can be caused by viral or bacterial infections, impacts an estimated six million Americans annually. Bacterial infections are considered one of the most common types of eye disorders. Such ophthalmic infections are frequently accompanied by inflammation of the infected ophthalmic tissues and sometimes the surrounding tissues. Similarly, ophthalmic surgical procedures that pose a risk of microbial infections may also cause inflammation of the affected tissues.

Disorders of the eye, such as bacterial infections of the eye, can lead to the need for application of pharmaceutical treatments, ocular surgical procedures, or both. Examples of these ophthalmic surgical procedures include cataract or lens replacement surgery. Given such facts, it is perhaps not surprising that an estimated 39 billion dollars was spent on treatments for conditions of the eye in 2021. The global market for conjunctivitis treatments alone is expected to exceed 6.5 billion dollars by the end of the decade. A large number of treatments have been approved over the last several decades to deal with bacterial conjunctivitis, including application of various aminoglycosides (e.g., tobramycin, gentamycin, etc.), macrolides (e.g., erythromycin, etc.), and use of other agents such as bacitracin, neomycin, polymyxin, sulfacetamide, chloramphenicol, fusidic acid, povidone-iodine, as well as a number of $2^{nd}$, $3^{rd}$ and $4^{th}$ generation fluoroquinolone antibiotics.

The quinolone antibiotics were developed in the early 1960s. Nalidixic acid is considered to be the predecessor of all members of the quinolone family, including the fluoroquinolones. Since the introduction of nalidixic acid, reportedly more than 10,000 quinolone analogs have been synthesized, but only a handful of such compounds have found their way into clinical practice. Some quinolone antibiotic compositions are effective in treating ophthalmic infections and have distinct advantages over prior ophthalmic antibiotic compositions, particularly those having relatively limited spectrums of antimicrobial activity. For example, neomycin, polymyxin B, gentamicin and tobramycin are primarily useful only against gram negative bacteria while bacitracin, gramicidin, and erythromycin are primarily useful only against gram positive bacteria. This well-known disparity in effectiveness reflects just some of the ways that quinolone antibiotics can vary in terms of pharmaceutical properties. For example, while FDA approved quinolone antibiotic products are useful for ophthalmologic and non-ophthalmologic applications, this is not always the case. In 2006, Bristol-Myers Squibb removed its gatifloxacin from the market after significant development, and sales of S150 million in 2005, due to safety concerns, despite the fact that ophthalmic gatifloxacin is considered well tolerated and has remained on the market since its launch in 2010 (marketed under the tradename Zymaxid®—Allergan).

Quinolones were widely used as a first-line treatment for many infections, including very commons ones such as acute sinusitis, acute bronchitis, and uncomplicated UTIs. Beginning in 2003, the topical ocular fourth-generation fluoroquinolones, moxifloxacin and gatifloxacin, were approved for treating bacterial conjunctivitis. These antibiotics represent the most advanced group of compounds within the class, offer a unique dual-binding mechanism of action in gram-positive organisms, and have activity against otherwise resistant species. However, reports of serious adverse events began emerging in the 2000s, and the FDA first added a "black box" warning to fluoroquinolone products in July 2008 for the increased risk of tendinitis and tendon rupture. In February 2011, the risk of worsening symptoms for those with myasthenia gravis was added to the warning. In August 2013, the agency required updates to the labels to describe the potential for irreversible peripheral neuropathy (serious nerve damage). In November 2015, an FDA Advisory Committee discussed the risks and benefits of fluoroquinolones for the treatment of acute bacterial sinusitis, acute bacterial exacerbation of chronic bronchitis, and uncomplicated UTIs based on new safety information. The new information focused on two or more side effects occurring at the same time and causing the potential for irreversible impairment. The FDA advisory committee concluded that the serious risks associated with the use of fluoroquinolones for these types of uncomplicated infections generally outweighed the benefits for patients with other treatment options, resulting in a recommendation of stronger safety warnings and more FDA safety communications regarding such drugs in 2016. There are also growing concerns about the use of these products due to the potential for developing antibiotic-resistant strains.

In addition to the serious concerns surrounding fluroquinolone antibiotics as active pharmaceutical ingredients ("APIs"), treating conditions of the eye, generally, is particularly challenging for the health care industry. For example, between 2003-2014, more than 14 pharmaceutical companies unsuccessfully attempted to secure FDA approval for dry eye drugs. Ocular tissue is one of the most complex and sensitive tissues in the human body. Accordingly, ophthalmological formulations can have a significant impact on the efficacy of such products. For example, the efficacy of many ophthalmological topical applications, such as, for example, those attempting to treat eye conditions such as conjunctivitis (inflammation of the conjunctiva) or other external ocular infections, often hinges on their ability to maintain contact with the afflicted eye anatomy or be retained by the eye, e.g., permeate and be held within, the cornea. Several excipients that are suitable for other types of pharmaceuticals or food are not suitable for ophthalmological applications (e.g., preservatives such as parabens, chlorocresol, and other agents are often not considered suitable for ophthalmological use). Moreover, changes to a single ingredient in ophthalmic formulations comprising even the same API can have significant effects on the pharmaceutical properties of such a formulation. For example, LUMIGAN® 0.01%, comprising one third the amount of the ophthalmological active ingredient bimatoprost, surprisingly shows very similar efficacy to LUMIGAN® 0.03%, despite only containing one-third of the active pharmaceutical ingredient ("API"), due to an increase in concentration of a single non-active excipient in the drug formulation (benzalkonium chloride). Even FDA-approved generic ophthalmologic products can be associated with significant challenges due to formulation issues. For example, with respect to prednisolone acetate 1% formulations, the generic formulation has exhibited caking of the drug and inadequate suspension of the product constituents, possibly compromising the treatment of inflamed eyes. Fiscella, Review of Optometry, 2002. Complaints of precipitated product clogging of the dropper tip have been filed, and two lots of generic prednisolone acetate were recalled due to precipitation of the active ingredient. Id.

The quinolones have properties that also require special attention with respect to drug product formulation. For example, published studies regarding the corneal penetration of fluoroquinolone products reflect that such products can exhibit different levels of penetration (e.g., with some studies demonstrating that on-market moxifloxacin and gatifloxacin products significantly greater levels in the aqueous humor than on-market ciprofloxacin product). Other studies have shown similar disparities in concentrations of other fluoroquinolone APIs from on-market formulations. Products containing multivalent cations, such as aluminum- or magnesium-containing antacids, and products containing calcium, iron, or zinc interact with fluoroquinolones and reduce drug efficacy. Other reactants with such APIs include sucralfate, probenecid, cimetidine, theophylline, warfarin, antiviral agents, phenytoin, cyclosporine, rifampin, pyrazinamide, and cycloserine.

There is a long history in patent records of attempts to address such problems with respect to fluroquinolone formulations. For example, U.S. Pat. No. 6,333,045 B1, which issued nearly 20 years ago, discloses, as a technique of enhancing cornea permeability of a drug, an aqueous liquid preparation containing gatifloxacin or a salt thereof at a relatively low concentration of gatifloxacin of lower than 0.5 w/v %, and sodium edetate at a low concentration. Furthermore, it reports that the solubility of gatifloxacin can be increased and precipitation of gatifloxacin crystals can be prevented in an aqueous liquid preparation containing gatifloxacin at a relatively low concentration of lower than 0.5 w/v % or a salt thereof by adding sodium edetate.

Many of the other formulations described in the patent literature focus on the use of xanthan gum. For example, U.S. Pat. No. 6,331,540 B1 discloses a pharmaceutical composition containing a fluoroquinolone antibiotic drug, xanthan gum and a water-soluble calcium salt. U.S. Publication No. 2009/0247543 A1 similarly discloses an aqueous liquid preparation comprising gatifloxacin or a pharmacologically acceptable salt thereof or a hydrate thereof, phosphoric acid or a salt thereof, and xanthan gum, wherein a pH thereof is 5.5 or more and less than 7.0. The suggested use of xanthan gum has been adopted in the art, with both moxifloxacin (e.g., Moxeza®—Novartis) and on-market moxifloxacin/Tobradex eye drop formulations containing xanthan gum.

U.S. Patent Publication No. 2014/0213561 A1 discloses a topical ophthalmic composition for treating ophthalmic bacterial infections in a human patient wherein the ophthalmic composition comprising gatifloxacin and prednisolone. The disclosed suspending agent in ophthalmic compositions disclosed in this patent publication includes METHOCEL™ F4M (a medium molecular weight hydroxypropyl methylcellulose (HPMC) thickener). Although Avelox IV is an intravenous formulation comprising moxifloxacin and microcrystalline cellulose, leading fluroquinolone ophthalmology formulations do not appear to have implemented the suggestion to use cellulose suspension agents.

These earlier products appear to be associated with shortcomings in terms of formulation properties, leading to the more recent suggestion to use other suspension agents, particularly non-ionic polyoxyethylene-polyoxypropylene block copolymer suspension agents (e.g., poloxamer suspension agents such as Pluronic® F-127 (BASF Corporation) and Poloxamer-407 (BASF Corporation)), to overcome such issues. For example, U.S. Patent Publication No. 2015/0024996 A1 discloses pharmaceutical compositions for intraocular administration comprising an anti-bacterial agent and anti-inflammatory agent, an excipient that acts as both a suspending agent and a solubilizing agent. The '996 application only cites non-ionic polyoxyethylene-polyoxypropylene block copolymers as providing such a function. The anti-bacterial agent selected from quinolone, a fluorinated quinolone, and pharmaceutically acceptable salts, hydrates, solvates, or N-oxides thereof and the anti-inflammatory agent selected from corticosteroids and pharmaceutically acceptable salts, hydrates, solvates, ethers, esters, acetals, and ketals thereof. U.S. Patent Publication No. 2019/0105320 A1 similarly discloses pharmaceutical compositions that include an anti-bacterial agent such as moxifloxacin and an anti-inflammatory agent such as prednisolone for intraocular injection. Both publications identify moxifloxacin as creating difficulties in forming stable suspension compositions when another component such as a corticosteroid like triamcinolone acetonide is present in the same formulation. These publications explain that the stable suspension problem is a result of moxifloxacin's tendency to deactivate many suspending agents, making unacceptable coagulation, clumping and flocculation. These publications also explain that numerous attempts by others to address this problem have been failed but the inventors were successful under specific conditions, namely by using a non-ionic polyoxyethylene-polyoxypropylene block copolymer at an amount of up to 10% by mass. The publication does not provide a different excipient that provides a stable composition with moxifloxacin or gatifloxacin and a corticosteroid such as triamcinolone acetonide.

As can be seen from the foregoing, in view of the sensitive and complex nature of the eye and the numerous known challenges in formulating ophthalmological products, particularly fluroquinolone formulations, inventive approaches are required to develop new effective fluroquinolone ophthalmological products that exhibit desirable properties such as reduced inflammation risk, uniform API distribution, and API stability.

Construction, Terms, and Acronyms

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention ("aspects") ("cases," "facets," or "embodiments"). The invention encompasses all aspects, as described individually and as can be arrived at by any combination of such individual aspects. The breadth and scope of the invention should not be limited by any exemplary embodiments. No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure". The term "i.a." ("ia" or "ia") means "inter glia" or "among other things." Uncontradicted, "elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means combinations of any or all such elements/steps. "Suitability" typically means acceptable or appropriate for performing a particular function/achieving particular state(s)/outcome(s), and typically means effective, practical, and non-deleterious/harmful in the context the term is used. "Pharmaceutical suitability", "pharmaceutically suitable", "ophthalmologically suitable" or "ophthalmological suitability" are phrases typically used to refer to compositions that are safe and effective for pharmaceutical administration and application, having sufficient potency, purity, strength, quality, and safety for pharmaceutical application, in cases specifically to the eye, as may be judged by regulatory authority review, and as established by, e.g., one or more well controlled and adequate clinical studies performed in compliance with generally prevailing regulatory authority standards. Compositions described as "ophthalmologically suitable" should be interpreted to mean suitable for ophthalmic delivery when provided in a potency, purity, strength, or quality making it safe for ophthalmic use. Components described as "ophthalmologically suitable" should be interpreted in a similar manner Uncontradicted, a description of "suitability" implicitly means that the referenced element, step, etc., is ophthalmologically/pharmaceutically suitable or otherwise medically suitable (e.g., safe and effective as determined by proper nonclinical/clinical testing).

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "—," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art, terms such as "about" should be interpreted as +/−10% of the indicated value(s).

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, for any value here that is not accompanied by a unit of measurement (e.g., a weight of 50), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

Uncontradicted, the term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," "mostly," or "primarily," means detectably >50% (e.g., mostly comprises, predominately includes, etc., mean >50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X).

Uncontradicted, any aspect described with respect to an optionally present element(s)/step(s) also provides implicit support for corresponding aspect(s) in which one, some, most, generally all, nearly all, essentially all, or all such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods described here can be performed in any suitable order regardless of presentation (e.g., a method comprising steps A, B, and C, can be performed in the order C, B, and A; B and A and C simultaneously, etc.). Uncontradicted, elements of a collection, system, device, or composition can be assembled in any suitable manner by any suitable method. In general, any methods and materials similar or equivalent to those described here can be used in the practice of embodiments. Uncontradicted, the use of ordinal numbers such as "first," "second," "third," and so on, is intended to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated using the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, or the like using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/ incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

Additional Terms, Concepts, and Acronyms

The following description of certain terms is provided to assist readers in understanding the invention. Additional defined terms may be only provided in other parts of this disclosure and use of acronyms that are well known in the art may not be provided here.

Uncontradicted, any description of the weight of any component without further description means a weight/ volume percent ("w/v. %"). In general, measurements of components in liquid formulations here are in weight/volume percent.

Except where explicitly indicated or clearly indicated by context, "improved" herein means "increased." In aspects, "improved" means "reduced," such as with respect to the toxicity of a composition, adverse events, and other negative characteristics, properties, or events. Uncontradicted, terms such as "enhanced," "improved," and the like are used synonymously. Any description of an improvement, increase, reduction, or enhancement or use of similar language, means a detectable or significant (DOS) such improvement, increase, reduction, or enhancement (or the like).

Uncontradicted, as suggested above, the term "suitable" generally means appropriate, acceptable, or in contexts sufficient, or providing at least generally or substantially all of an intended function, without causing or imparting significant negative/detrimental impact. For example, a suitable mixture means a mixture of elements/ingredients which may be present with one another without significant negative impact to any one or more such elements/ingredients in the mixture, e.g., the elements/ingredients are compatible with one another. As another example, suitable functionality means exhibiting/retaining function(s) that are not significantly different from a referenced counterpart function.

Terms such as "ophthalmologically suitable" should be interpreted as referencing a compound that is safe for ophthalmic delivery, or compounds modified in such a way so as to make such compounds safe for ophthalmic administration.

Described here are compositions which can be characterized, in aspects, by the elements of which they are comprised. In aspects, compositions provided by the invention are characterized as having one or more "components". Used here, uncontradicted, the term "components" refers to one or compounds which provide a specific function. For example, a "quinolone antibiotic component" is a component of a composition comprising one or more constituents which each alone or together provide(s) detectable or significant antimicrobial effect(s); an "anti-inflammatory steroid component" is a component of a composition comprising one or more constituents which each alone or together provide(s) an anti-inflammatory effect, etc. Here, the term "constituents" typically refers to a compound of a component or composition. The term "agent" also can be used synonymously with "constituent", "ingredient", or "compound". The term "ingredient", "ingredients", or "ingredient(s)" can refer to an individual compound (which may, or may not, be a constituent of a component) or a component of a composition. Terms such as "product" are used here in reference to compositions disclosed here. Based on context, such terms can either refer to either formulation compositions disclosed here or other compositions comprising such formulation compositions, such as drug/device combinations, kits, and the like A "therapeutically effective amount" typically means an amount of a compound or pharmaceutical composition that will elicit an intended (typically significant) biological or medical response of a tissue, system, animal, or human that is being sought by the researcher, medical doctor, or other clinician. In aspects, a therapeutically effective amount is demonstrated by at least one or at least two well controlled and adequate clinical studies in human subjects/patients (e.g., as would be considered sufficient for pharmaceutical approval).

The term "effective", when used in reference to an excipient/component of a composition, refers to detectably or significantly performing/increasing the functionality of one or more actives or primary ingredients of the composition or detectably or significantly modifying one or more characteristics of the composition in one or more intended manners (e.g., in terms of suspending the API for an excipient characterized as a suspending agent, in terms of buffering the composition for a component described as a buffer, etc.). An "effective" excipient is also an excipient that is suitable for ophthalmological use in terms of safety and maintaining effectiveness of associated API(s). For example, an effective amount of a suspension component is an amount that at least detectably or significantly increases the particle suspension of one or more active pharmaceutical ingredients (e.g., one or more fluoroquinolone antibiotic compounds, one or more steroid anti-inflammatory compounds, one or more non-steroid anti-inflammatory compounds, or any combination thereof), such that most, generally all, substantially all, or all particles of the composition are mostly, generally, or completely suspended for at least about 75%, >~80%, >~85%, >~90%, >95%, or, e.g., about 100% of the time the product is being applied or administered or, e.g., such that the uniformity of the composition does not change over a period of at least about 5 minutes, such as, e.g., ≥~10 minutes, ≥~20 minutes, ≥~30 minutes, >~40 minutes, >~50 minutes, ≥~1 hour, >~3 hours, ≥~6 hours, >~12 hours, >~18 hours, >~24 hours, >~2 days, >~3 days, >~4 days, >~5 days, >~6 days, ≥~1 week, >~2 weeks, >~3 weeks, >~1 month, >~2 months, >~3 months, >~4 months, >~5 months, >~6 months, >~1 year, >~1.5 years, >~2 years, >~2.5 years, or, e.g., >~3 years or more.

Terms such as "ophthalmologically suitable" generally mean that a referenced composition, excipient, API, etc., is suitable for application to the eye, the area around the eye, or both (e.g., as determined by safety testing such as through one or more well-controlled clinical studies in relevant subjects resulting in a significant determination of suitability in terms of safety, toxicity, irritability, lack of other major adverse events associated with ophthalmological products, and the like). In certain embodiments, an ophthalmologically suitable composition is a composition which does not detectably or significantly irritate or inflame the eye or the area surrounding the eye (e.g., in a significant number of patients as determined through such above-referenced studies), cause significant eye irritation, or cause the receiving subject to experience significant discomfort due to its application (again, typically as determined on a detectable or significant level through one or more well-controlled studies). Compositions, formulations, components/excipients, etc., described/referenced with respect to compositions or methods of the invention are implicitly to be understood as referring to ophthalmologically suitable material(s)/composition(s).

Sometimes terms such as "pharmaceutically acceptable" or "pharmacologically acceptable" also are used here with respect to compositions, excipients, steps, etc. In general, such terms should be construed the same as "ophthalmologically suitable."

A suitable excipient/component typically means a pharmaceutically inactive component that is compatible with other ingredients of the formulation (does not cause such other components to be inactivated or unstable, react to form undesirable reactants, etc.), which is not detectably or significantly deleterious to the recipient of the composition, which is formulated in combination with the APIs of the composition, and which typically detectably or significantly imparts one or more characteristics to a composition/API, improves one or more characteristics of the composition/API (e.g., delivery, stability, form, distribution of APIs, chemical characteristics of the composition, etc.), or both. This concept of suitable "compatibility" is applicable to any combination of ingredients in a composition of the invention.

Many characteristics of compositions are provided here which are described relative to storage conditions. In aspects, compositions are administered by injection and products relate to injectable products. In aspects, products disclosed herein are adapted to be administered or are administered topically (e.g., as ophthalmic drops). In aspects, storage conditions relative to descriptions of product stability are different for injectable products vs. topically applied ophthalmic products. Stability can be assessed under any suitable temperature and humidity conditions, such as those applied for the relevant type of product by FDA. In aspects, particular temperature and humidity conditions are provided. E.g., for topically applied ophthalmic products (e.g., drops) such conditions can be about 25° C. and about 40% relative humidity, or about 40° C. and no more than about 25% relative humidity and for injectable products such conditions can be 25° C. and about 60% relative humidity or at about 40° C. and about 75% relative humidity.

SUMMARY OF THE INVENTION

The compositions and methods disclosed herein have many attributes and aspects including, but not limited to, those set forth in, e.g., described or referenced in, this Summary of the Invention ("Summary"). This Summary is not intended to be all-inclusive, and the scope of the invention is not limited to or limited by the aspects, features, elements, or embodiments provided in this Summary. The Summary is provided for efficient illustrative purposes only and not restriction. Any aspects of compositions or methods described in this section can be combined with any other aspect in this section or any other part of this disclosure.

In aspects, the invention provides pharmaceutically acceptable/ophthalmologically suitable compositions or uses thereof comprising a quinolone (e.g., fluroquinolone) antibiotic(s), one or more anti-inflammatory steroid agents, or both. Such formulations can, in aspects, be characterized by being physically and chemically stable suspensions or solutions, in cases with improvements in terms of less flocculation, coagulation, and the like, with respect to other formulations. In aspects, compositions provided by the invention provide both broad-spectrum antibiotic activity and anti-inflammatory activity from one or more steroidal or non-steroidal agents.

In specific embodiments, the invention provides physically and chemically stable, pharmaceutically acceptable, and ophthalmologically suitable compositions comprising therapeutically effective amounts of one or more gatifloxacin compounds, one or more prednisolone compounds, and one or more bromfenac compounds in a suspension.

In aspects, the invention provides an ophthalmologically suitable pharmaceutical composition in the form of a solution or suspension comprising: (a) a suspension component consisting of both (1) an effective amount of least one non-ionic suspension agent and (2) an effective amount of at least one ionic suspension agent; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL.

In aspects, the invention provides an ophthalmologically suitable pharmaceutical composition in the form of a solution or suspension comprising: (a) an effective amount of at least one ionic suspension agent; (b) an effective amount of at least one non-ionic surfactant; (c) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (d) a pharmaceutically acceptable chelating agent that results in a significantly similar or improved stability of the active ingredients as compared to disodium edetate in a concentration of about 0.1 to 0.5 mg/mL.

In aspects, the invention provides an ophthalmologically suitable pharmaceutical composition in the form of a solution or suspension comprising: (a) at least 1.5 wt. % of a suspension agent component comprising an effective amount of a natural or semi-synthetic suspension agent other than xanthan gum; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL, (d) wherein (a) the composition has a viscosity of about 3.5-about 25 mPas and (b) the composition exhibits significantly less flocculation, coagulation, clumping, or combination of any or all thereof as opposed to a corresponding formulation comprising xanthan gum in place of the suspension agent.

In aspects, the invention provides an ophthalmologically suitable pharmaceutical composition in the form of a solution or suspension comprising: (a) an effective amount of least one natural or semi-synthetic suspension agent composed of a compound having an average molecular weight of between 10,000 and 1,000,000 Daltons; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL.

In aspects, the invention provides an ophthalmologically suitable pharmaceutical composition in the form of a solution or suspension comprising: (a) an effective amount of a suspension agent comprising effective amounts of two nonionic suspension agents, one of which nonionic suspension agents having surface active activity; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL.

In aspects, the invention provides an ophthalmologically suitable pharmaceutical composition in the form of a solution or suspension comprising: (a) an effective amount of a suspension agent; (b) an effective amount of a polyoxylethylated castor oil; (c) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (d) a pharmaceutically acceptable chelating agent that results in a significantly similar or improved stability of the active ingredients as compared to disodium edetate in a concentration of about 0.1 to 0.5 mg/mL.

In aspects, the invention provides a method of using any one or more pharmaceutically acceptable and ophthalmologically suitable compositions described herein to treat or prevent inflammation associated with physical trauma to ophthalmic tissue(s), inflammation associated with microbial (e.g., bacterial) infection(s), inflammation resulting from surgical procedure(s), or any combination thereof.

In aspects, the invention provides a method of using any one or more pharmaceutically acceptable and ophthalmologically suitable compositions described herein to treat or prevent an ocular microbial infection.

In aspects, the invention provides a method of using any one or more pharmaceutically acceptable and ophthalmologically suitable compositions described herein to treat or prevent significant inflammation associated with physical trauma to ophthalmic tissue(s), significant inflammation associated with microbial (e.g., bacterial) infection(s), inflammation resulting from surgical procedure(s), to treat or prevent an ocular microbial infection, or any combination thereof.

In aspects, the invention provides a method of treating or preventing a disease or condition benefiting from a combination therapy of a quinolone antibiotic antimicrobial component and a steroid or steroid and non-steroid anti-inflammatory component, the method comprising administering an effective amount of a pharmaceutically acceptable and ophthalmologically suitable composition, comprising pharmaceutically acceptable amounts of any one or more compositions described above.

DETAILED DESCRIPTION OF THE INVENTION

For convenience, both combinations of elements/steps and individual elements/steps may be described in this section of this disclosure. Despite the inclusion of passages focused on specific elements/steps, readers should understand that any aspect, facet, embodiment, or other description of particular step(s) or element(s) can be applied to any general description of the compositions/methods of the invention, or any other recited element(s)/step(s) thereof, which are provided in any part of this disclosure.

Compositions

The invention provides compositions comprising a therapeutically effective amount of pharmacologically acceptable/ophthalmologically suitable quinolone API(s), a therapeutically effective amount of a pharmacologically acceptable/ophthalmologically suitable, an anti-inflammatory steroid API, or both, and an ophthalmologically suitable suspension component. Uncontradicted, "compositions" herein mean compositions of the invention. As noted, compositions formed by mixtures of API(s) and excipients can be called formulations and formulation compositions are often simply called compositions, as will be clear to readers from context. In other cases, compositions can refer to drug/device combinations, kits, and other more complex compositions. The term composition also is sometimes used in reference to ingredients/components, which will be clear from context.

In aspects, compositions/formulations comprise one or more additional pharmacologically acceptable/ophthalmologically suitable excipients and API(s), typically ≥2 API(s) in combination. In cases, ≥2 APIs of a formulation are APIs that will DOS flocculate, coagulate, clump, cake, precipitate, or react or degrade, in a formulation that is not formulated with a suspension component provided here. Compositions described herein are suitable for ophthalmic application to a mammalian eye (e.g., to a human eye). In aspects, compositions comprise both a therapeutically effective amount of a quinolone antibiotic and a therapeutically effective amount of an anti-inflammatory steroid component, in combination with an effective and suitable suspension component. In aspects, compositions described here are free of certain agents. E.g., in aspects compositions are free of one or more, or all, block copolymers of poly(ethylene oxide) and poly (propylene oxide) (e.g., Pluronic or Poloxamer excipients, such as those specifically described in the Background of this disclosure), xanthan gum, crystalline cellulose/micro cellulose, or hydroxypropylmethylcellulose (HPMC).

The quinolone antibiotic API(s) or steroid anti-inflammatory agent API(s) of the formulation and the suspension agent are sometimes collectively described as the "primary ingredients" of formulations/compositions. In aspects, the "primary ingredients" also or alternatively include a surfactant component, such as a non-ionic surfactant component, a chelator component, or both. In aspects, a non-ionic surfactant of the composition also acts as a suspension agent. Additional ingredients, which in aspects are optional ingredients but which in embodiments can be required, are also described here. Such ingredients can, in aspects, provide one or more measurable, e.g., detectable or significant effect(s) when provided in effective amounts. In aspects, additional ingredients can be provided to aid in composition stability, composition application, composition characteristics (e.g., pH), composition effect, or any combination thereof. In aspects, one or more additional ingredients are directly related to a detectable or significant therapeutic/physiological effect, an effect on shelf life of the product, an effect on patient compliance, an effect in distribution of the product, etc. In aspects, one or more additional ingredients are directly related to a detectable or significant effect on product usability, such as, e.g., the prevention of the development of a detectable or significant non-uniform consistency of a composition, which in aspects is not directly related to a therapeutic effect yet can, in aspects, be directly related to the suitability of the composition for use in the eye.

In aspects, compositions comprise at least one quinolone antibiotic component and at least one anti-inflammatory component, which can be an NSAD, an anti-inflammatory steroid, another anti-inflammatory agent, or a combination of any or all thereof. In aspects, compositions provided by the invention comprise at least 2, such as, e.g., ≥~3, ≥~4, or ≥~5 or more active pharmaceutical ingredients (APIs). In aspects, the invention provides compositions comprising between 2-3 APIs (e.g., ≥2 quinolone antibiotic APIs and >1 anti-inflammatory steroid(s) or ≥1 quinolone antibiotic API(s) and >2 anti-inflammatory steroid APIs). In aspects, compositions comprise at least one quinolone antibiotic, e.g., at least one fluoroquinolone antibiotic. As noted, quinolone antibiotics can vary in terms of formulation properties, efficacy properties, and the like. Accordingly, certain aspects of the invention are limited to certain types of quinolone antibiotics. In aspects, compositions also or alternatively comprise at least one non-steroidal anti-inflammatory compound. In aspects, compositions comprise at least one steroidal anti-inflammatory compound and at least one non-steroidal anti-inflammatory compound.

Ingredients

To better illuminate the scope of the invention, a description of classes of ingredients of compositions/formulations of the invention is provided in this section.

Quinolone Antibiotic Component

In aspects, compositions comprise one or more quinolone antibiotic components. A quinolone antibiotic component means any ≥1 quinolone antibiotics, such as those quinolone antibiotics specifically referred to herein, equivalents thereof known in the art, effective derivatives/analogs thereof, or any suitable salt, hydrate, solvate, ether, ester, acetal, polymorph, and ketal thereof. In general, any quinolone antibiotic(s) can be included in formulations. However, readers will understand that certain quinolone antibiotic(s) described herein have advantageous properties and represent unique aspects of the invention.

In aspects, ≥1 of the quinolone antibiotics has a structure based on the 4-quinolone ring structure or having a structure according to Formula I—

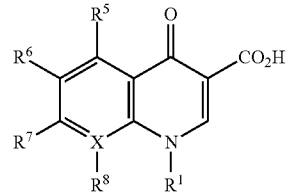

Wherein R1, R5-R8, & X are optionally any pharmaceutically acceptable substituent. In aspects, R1 is a cyclopropane or a difluorobenzene; R5 is an amino, hydroxyl, or methyl; R6 is a fluorine; R7 is an alkyl substituent, such as a nitrogen containing cycloalkyl (heterocycloalkyl); and R8 is a fluorine-, chlorine-, nitrogen-, or carbon-containing group, e.g., as exemplified in Pham et al., Med. Chem. Commun., 2019, 10, 1719-1739, DOI: 10.1039/C9MD00120D, which is specifically incorporated herein by reference. In aspects, one or more of positions (R) 6, 7, and 8 are substituted by fluoro, 3-methylpiperazin-1-yl, and methoxy groups, respectively. The structure of quinolone/fluoroquinolone antibiotics has been extensively studied in the art and, accordingly, does not have to be further described herein. In aspects, X is a carbon, which is typically found in quinolones.

Some quinolone antibiotics demonstrate broad-spectrum activity. Some quinolone antibiotics do not demonstrate broad-spectrum activity. In aspects, an effective amount of ≥1 quinolone antibiotics demonstrating broad spectrum activity are present in compositions. In aspects, as a quinolone antibiotic, can be any pharmaceutically acceptable or ophthalmologically suitable quinolone antibiotic, such as, e.g., first generation quinolones (e.g., nalidixic acid and cinoxacin), second generation quinolones (e.g., norfloxacin, lomefloxacin, enoxacin, ofloxacin, and ciprofloxacin), third generation quinolones (e.g., levofloxacin, sparfloxacin, gatifloxacin, and moxifloxacin), or fourth generation quinolones (e.g., trovafloxacin and gemifloxacin). The classification of the "generation" of quinolone antibiotics varies in the art, but in general these classes are now fairly well defined in the art based on functionality of included antibiotics (e.g., third generation fluroquinolones exhibit broad spectrum activity against aerobic gram-negative and gram-positive bacteria and fourth generation fluroquinolones, e.g., exhibit both broad-spectrum activity against aerobic and anaerobic species. See, e.g., Scoper S V. Review of third- and fourth-generation fluoroquinolones in ophthalmology: in-vitro and in-vivo efficacy. Adv Ther. 2008 October; 25(10):979-94. doi: 10.1007/s12325-008-0107-x. PMID: 18836691; Mather R, Karenchak L M, Romanowski E G, Kowalski R P. Fourth generation fluoroquinolones: new weapons in the arsenal of ophthalmic antibiotics. Am J Ophthalmol. 2002 April; 133 (4):463-6. doi: 10.1016/s0002-9394(02)01334-x. PMID: 11931779; and King et al., Am Fam Physician. 2000 May 1; 61(9):2741-2748.

In aspects, the quinolone antibiotic component comprises ≥1 quinolone antibiotic APIs which are any ophthalmologically suitable and classified/classifiable as broad-spectrum antibiotic compound(s). In aspects, the quinolone antibiotic is any ophthalmologically suitable quinolone antibiotic demonstrating suitable therapeutic efficacy against a target infective agent (such as, e.g., common ocular infective agents such as Staphylococcal & *Haemophilus* species).

In aspects, quinolone antibiotic components comprise one or more ophthalmologically suitable antibiotic compounds classifiable as a fluoroquinolone, chloroquine, or hydroxychloroquine. In aspects, a quinolone compound is a fluoroquinolone antibiotic compound. In aspects, compositions can comprise any suitable ≥1 fluoroquinolone compound(s). Exemplary fluoroquinolone compounds include, e.g., ciprofloxacin, ofloxacin, gemifloxacin, levofloxacin, moxifloxacin, and gatifloxacin. In aspects, fluoroquinolone antibiotic(s) in compositions include moxifloxacin, ofloxacin, ciprofloxacin, fleroxacin, lomefloxacin, nadifloxacin, norfloxacin, pefloxacin, rufloxacin, balofloxacin, grepafloxacin, levofloxacin, pazufloxacin, sparfloxacin, temafloxacin, clinafloxacin, gatifloxacin, sitafloxacin, prulifloxacin, besifloxacin, delafloxacin, etc. In aspects, one or more derivatives of such compositions are included. Examples of known derivatives include, e.g., delafloxacin, finafloxacin, ozenoxacin, avarofloxacin, cadazolid, zabofloxacin, lascufloxacin, nemonoxacin, ophthalmologically suitable (e.g., modified for ophthalmological use) OPS-2017 levonadifloxacin (WCK 771)+alalevonadifloxacin (WCK 23491, oral prodrug), TNP-2092 (a rifamycin-quinolizinone hybrid), MCB3837 (oxazolidinone-quinolone hybrid). In aspects, a derivative is a structurally similar compound having suitable, similar, or improved properties with respect to one or more known "parent" APIs, such as moxifloxacin or gatifloxacin. In aspects, compositions can comprise one or more therapeutically effective and ophthalmologically suitable derivative of any one or more quinolone compounds described herein, such as any therapeutically effective and ophthalmologically suitable derivative of a core quinolone structure (e.g., according to Formula 1, supra), wherein modifications are made at, e.g., one or more of R1 or R5-R8 thereof.

In aspects, the quinolone antibiotic component of compositions provided by the invention comprise one or more therapeutically effective and ophthalmologically suitable quinolone compounds, such as, e.g., a fluoroquinolone compound, in an amount representing between about 0.01-1 wt. % of the composition, such as, e.g., between ~0.01-~0.9 wt. %, ~0.01-~0.8 wt. %, ~0.01-~0.7 wt. %, ~0.01-~0.6 wt. %, ~0.01-~0.5 wt. %, ~0.01-~0.4 wt. %, ~0.01-~0.3 wt. %, ~0.01-~0.2 wt. %, ~0.01-~0.1 wt. %, such as, e.g., between ~0.02-~1 wt. %, ~0.03-~1 wt. %, ~0.04-~1 wt. %, ~0.05-~1 wt. %, ~0.06-~1 wt. %, ~0.07-~1 wt. %, ~0.08-~1 wt. %, ~0.09-~1 wt. %, ~0.1-~1 wt. %, as in, for example, between ~0.02-~0.8 wt. %, ~0.03-~0.7 wt. %, ~0.04-~0.6 wt. %, ~0.05-~0.4 wt. %, ~0.06-~0.3 wt. %, ~0.07-~0.2 wt. %, ~0.08-~0.2 wt. %, ~0.09-~0.2 wt. %, or, e.g., about 0.1 wt. % of the composition. In aspects, the quinolone compound is a fluoroquinolone.

In aspects, compositions comprise between about 0.01-10 mg/mL of a therapeutically effective and ophthalmologically suitable quinolone antibiotic compound, such as, e.g., between ~0.01-~9 mg/mL, ~0.01-~8 mg/mL, ~0.01-~7 mg/mL, ~0.01-~6 mg/mL, ~0.01-~4 mg/mL, ~0.01-~3 mg/mL, ~0.01-~2 mg/mL, ~0.01-~1 mg/mL, such as, e.g., between ~0.05-~10 mg/mL, ~0.1-~10 mg/mL, ~0.15-~10 mg/mL, ~0.20-~10 mg/mL, ~0.25-~10 mg/mL, ~0.30-~10 mg/mL, ~0.35-~10 mg/mL, ~0.40-~10 mg/mL, ~0.45-~10 mg/mL, ~0.50-~10 mg/mL, ~0.55-~10 mg/mL, ~0.60-~10 mg/mL, ~0.65-~10 mg/mL, ~0.70-~mg/mL, ~0.75-~10 mg/mL, ~0.80-~10 mg/mL, ~0.85-~10 mg/mL, ~0.90-~10 mg/mL, ~0.95-~10 mg/mL, ~1-~10 mg/mL, as in, for example, between ~0.1-9 mg/mL, ~0.2-~8 mg/mL, ~0.3-~7 mg/mL, ~0.4-~6 mg/mL, ~0.5-~5 mg/mL, ~0.6-~4 mg/mL, ~0.7-~3 mg/mL, ~0.8-~2 mg/L, ~0.9-~2 mg/mL, ~0.9-~1.9 mg/mL, ~0.9-~1.8 mg/mL, ~0.9-~1.7 mg/mL, ~0.9-~1.6 mg/mL, ~0.9-~1.5 mg/mL, ~0.9-~1.4 mg/mL, ~0.9-~1.3 mg/mL, ~0.9-~1.2 mg/mL, or ~0.9-~1.1 mg/mL, or, e.g., about 1 mg/mL of a quinolone antibiotic compound. In aspects, the quinolone compound is a fluoroquinolone.

In aspects, compositions comprise between about 0.01-2 wt. % of a therapeutically effective and ophthalmologically suitable quinolone antibiotic compound, such as, e.g., a fluoroquinolone compound, such as, e.g., between ~0.01-~1.9 wt. %, ~0.01-1.8 wt. %, ~0.01-~1.7 wt. %, ~0.01-~1.6 wt. %, ~0.01-~1.5 wt. %, ~0.01-~1.4 wt. %, ~0.01-~1.3 wt. %, ~0.01-~1.2 wt. %, ~0.01-~1.1 wt. %, ~0.01-~1 wt. %, ~0.01-~0.9 wt. %, ~0.01-~0.8 wt. %, ~0.01-~0.7 wt. %, ~0.01-~0.6 wt. %, ~0.01-~0.5 wt. %, ~0.01-~0.4 wt. %, ~0.01-~0.3 wt. %, ~0.01-~0.2 wt. %, ~0.01-~0.1 wt. % such as, e.g., between ~0.02-~2 wt. %, ~0.03-~2 wt. %, ~0.04-~2 wt. %, ~0.05-~2 wt. %, ~0.06-~2 wt. %, ~0.07-~2 wt. %, ~0.08-~2 wt. %, ~0.09-~2 wt. %, ~1-2 wt. %, ~1.1-~2 wt. %, ~1.2-~2 wt. %, ~1.3-~2 wt. %, ~1.4-~2 wt. %, ~1.5-~2 wt. %, ~1.6-~2 wt. %, ~1.7-~2 wt. %, ~1.8-~2 wt. %, ~1.9-~2 wt. %, as in, for example, between ~0.02-~1.9 wt. %, ~0.03-~1.8 wt. %, ~0.04-~1.7 wt. %, ~0.05-~1.6 wt. %, ~0.06-~1.5 wt. %, ~0.07-~1.4 wt. %, ~0.08-~1.3 wt. %, ~0.09-~1.2 wt. %, ~0.1-~1.1 wt. %, ~0.2-~1 wt. %, ~0.3-~0.9 wt. %, ~0.4-~0.8 wt. %, ~0.4-~0.7 wt. %, ~0.4-~0.6 wt. % or, e.g., about 0.5 wt. %. of a quinolone antibiotic compound. In aspects, the quinolone compound is a fluoroquinolone compound.

In aspects, compositions comprise between about 1-10 mg/mL of a therapeutically effective and ophthalmologically suitable quinolone antibiotic compound, such as, e.g., a fluoroquinolone compound such as, e.g., between ~1-~9.5 mg/mL, ~1-9 mg/mL, ~1-~8.5 mg/mL, ~1-~8 mg/mL, ~1-~7.5 mg/mL, ~1-~7 mg/mL, ~1-~6.5 mg/mL, ~1-~6 mg/mL, ~1-~5.5 mg/mL, ~1-~5 mg/mL, ~1-~4.5 mg/mL, ~1-~4 mg/mL, ~1-~3.5 mg/mL, ~1-~3 mg/mL, ~1-~2.5 mg/mL, ~1-~2 mg/mL, ~1-~1.5 mg/mL, such as, e.g. ~1.5-~10 mg/mL, ~2-~10 mg/mL, ~2.5-~10 mg/mL, ~3-~10 mg/mL, ~3.5-~10 mg/mL, ~4-~10 mg/mL, ~4.5-~10 mg/mL, ~5-~10 mg/mL, ~5.5-~10 mg/mL, ~6-~10 mg/mL, ~6.5-~10 mg/mL, ~7-~10 mg/mL, ~7.5-~10 mg/mL, ~8-~10 mg/mL, ~8.5-~10 mg/mL, ~9-~10 mg/mL, ~9.5-~10 mg/mL as in, for example, between ~1.5-~9.5 mg/mL, ~2-~9 mg/mL, ~2.5-~8.5 mg/mL, ~3-~8 mg/mL, ~3.5-~7.5 mg/mL, ~4-~7 mg/mL, ~4.5-6.5 mg/mL, ~4.5-~6 mg/mL, ~4.5-~5.5 mg/mL, or, e.g., about 5 mg/mL of a quinolone compound. In aspects, the quinolone compound is a fluoroquinolone compound.

In aspects, compositions comprise a quinolone antibiotic component comprising one or more quinolone antibiotic compounds, such as, e.g., one or more fluoroquinolone compounds, demonstrating a microbial inhibition activity of at least that demonstrated by moxifloxacin, at least that demonstrated by gatifloxacin, or both, against common ophthalmic infective microbes, such as, e.g., *Haemophilus influenza, Streptococcus pneumoniae,* and *Staphylococcus aureus,* coagulase-negative staphylococci, *Pseudomonas aeruginosa,* gram negative bacilli, etc.

Moxifloxacin

In certain aspects, compositions provided by the invention comprise, e.g., a quinolone antibiotic component of compositions provided by the invention comprise, mostly comprise, generally consist of, substantially consist of, or consist of one or more moxifloxacin compounds (any suitable salt form of moxifloxacin, such as a hydrocholoride form thereof, any suitable derivative of moxifloxacin, or a combination thereof). Moxifloxacin compounds inhibit the bacterial enzymes DNA gyrase (topoisomerase II) and topoisomerase IV, resulting in inhibition of DNA replication and repair and cell death in sensitive bacterial species.

In aspects, the invention provides ophthalmic compositions comprising one or more ophthalmologically suitable compounds which, when delivered to the eye of a subject in sufficient amounts, result in detectable or significant antimicrobial effects, approximately the same or significantly similar to those typically provided by a corresponding amount of moxifloxacin hydrochloride or that provide an improvement on such effects. In aspects, such compositions comprise one or more moxifloxacin compounds. In aspects, one or more of such moxifloxacin compounds also provide therapeutic effects significantly similar to, or that improve upon, therapeutic effects associated with moxifloxacin hydrochloride in similar application and amount. In aspects, moxifloxacin compounds are mostly, generally, or only composed of moxifloxacin, rather than an analog or derivative thereof. In aspects, moxifloxacin compounds comprise, mostly comprise, or only comprise one or more suitable moxifloxacin analogs or derivatives which can vary, for example, by providing different phenol and alkyl halide(s) at the third position of the carboxylic group via an esterification reaction (see, e.g., Akhtar, et. al., in "Moxifloxacin-Ester derivatives: Synthesis, characterization and pharmacological evaluation," Pak J Pharm Sci. 2019 May; 32(3 Special): 301-1306); modifications to the core of moxifloxacin (e.g., 8D derivative described by, e.g., Rocha-Roa, et. al. in "In silico study of Moxifloxacin derivatives with possible antibacterial activity against a resistant form of DNA gyrase from Porphyromonas gingivalis", Archives of Oral Biology, Volume 95, November 2018, Pages 30-39), and, e.g., introduction of alky, acyl, or sulfonyl moieties to the basic secondary amine moiety of moxifloxacin (see, e.g., Kulabas, et. al. in "Design, synthesis and molecular modeling studies on novel moxifloxacin derivatives as potential antibacterial and antituberculosis agents," Bioorg Chem. 2019 July; 88:102965, Epub 2019 May 2), etc.

In aspects, compositions provided by the invention comprises any form of ophthalmologically suitable moxifloxacin compound, such as, e.g., any pharmaceutically acceptable derivative, prodrug, hydrate, salt, solvate, enantiomer, or polymorph thereof. In aspects, moxifloxacin compounds of the compositions provided by the invention comprise any ophthalmologically suitable analog or derivative of moxifloxacin. In aspects, compositions provided by the invention comprise a single type of moxifloxacin compound, while in alternative aspects, compositions comprise two or more types of moxifloxacin compounds e.g., two different derivatives of moxifloxacin, each differing from the other in, e.g., their compound size, level of detectable effect (e.g., microbial inhibition activity), pKa value, etc.

In certain aspects, compositions provided by the invention comprise a salt of moxifloxacin. In aspects, most, generally all, or all of the moxifloxacin compound(s) comprise moxifloxacin in one or more salt forms. In aspects, the moxifloxacin comprises, mostly comprises, generally consists of, consists of, or consists essentially of moxifloxacin hydrochloride. In aspects, a quinolone antibiotic component is composed of ≥2 APIs, of which a moxifloxacin component, such as moxifloxacin HCl, is one component. Moxifloxacin hydrochloride is an 8-methoxy fluoroquinolone anti-infective, with a diazabicyclononyl ring at the C7 position. Moxifloxacin hydrochloride is chemically 1-Cyclopropyl-6-fluoro-1,4-dihydro-8-methoxy-7-[(4aS,7aS)-octahydro-6H-pyrrolo[3,4b] pyridin-6-yl]-4-oxo-3-quinolinecarboxylic acid, monohydrochloride (molecular formula $C_{21}H_{24}FN_3O_4 \cdot HCl$).

Moxifloxacin Amount

According to aspects, the invention provides an ophthalmologically suitable composition comprising an effective amount of moxifloxacin compound(s), such as, e.g., a salt of moxifloxacin, such as, e.g., moxifloxacin HCl, wherein the ophthalmologically suitable moxifloxacin compound is present in the composition in an amount representing between about 0.01-1 wt. % of the composition, such as, e.g., between ~0.01-~0.9 wt. %, ~0.01-~0.8 wt. %, ~0.01-~0.7 wt. %, ~0.01-~0.6 wt. %, ~0.01-~0.5 wt. %, ~0.01-~0.4 wt. %, ~0.01-~0.3 wt. %, ~0.01-~0.2 wt. %, ~0.01-~0.1 wt. %, such as, e.g., between ~0.02-~1 wt. %, ~0.03-~1 wt. %, ~0.04-~1 wt. %, ~0.05-~1 wt. %, ~0.06-~1 wt. %, ~0.07-~1 wt. %, ~0.08-~1 wt. %, ~0.09-~1 wt. %, ~0.1-~1 wt. %, as in, for example, between ~0.02-~0.8 wt. %, ~0.03-~0.7 wt. %, ~0.04-~0.6 wt. %, ~0.05-~0.4 wt. %, ~0.06-~0.3 wt. %, ~0.07-~0.2 wt. %, ~0.08-~0.2 wt. %, ~0.09-~0.2 wt. %, or, e.g., about 0.1 wt. % of the composition.

In aspects, the invention provides an ophthalmologically suitable composition comprises an effective amount of moxifloxacin compound(s), such as, e.g., a salt of moxifloxacin, such as, e.g., moxifloxacin HCl, wherein the composition comprises between about 0.01-about 10 mg/mL, such as, e.g., between ~0.01-~9 mg/mL, ~0.01-~8 mg/mL, ~0.01-~7 mg/mL, ~0.01-~6 mg/mL, ~0.01-~4 mg/mL, ~0.01-~3 mg/mL, ~0.01-~2 mg/mL, ~0.01-~1 mg/mL, such as, e.g., between ~0.05-~10 mg/mL, ~0.1-~10 mg/mL, ~0.15-~10 mg/mL, ~0.20-~10 mg/mL, ~0.25-~10 mg/mL, ~0.30-~10 mg/mL, ~0.35-~10 mg/mL, ~0.40-~10 mg/mL, ~0.45-~10 mg/mL, ~0.50-~10 mg/mL, ~0.55-~10 mg/mL, ~0.60-~10 mg/mL, ~0.65-~10 mg/mL, ~0.70-~mg/mL, ~0.75-~10 mg/mL, ~0.80-~10 mg/mL, ~0.85-~10 mg/mL, ~0.90-~10 mg/mL, ~0.95-~10 mg/mL, ~1-~10 mg/mL, as in, for example, between ~0.1-9 mg/mL, ~0.2-~8 mg/mL, ~0.3-~7 mg/mL, ~0.4-~6 mg/mL, ~0.5-~5 mg/mL, ~0.6-~4 mg/mL, ~0.7-~3 mg/mL, ~0.8-~2 mg/L, ~0.9-~2 mg/mL, ~0.9-~1.9 mg/mL, ~0.9-~1.8 mg/mL, ~0.9-~1.7 mg/mL, ~0.9-~1.6 mg/mL, ~0.9-~1.5 mg/mL, ~0.9-~1.4 mg/mL, ~0.9-~1.3 mg/mL, ~0.9-~1.2 mg/mL, or ~0.9-~1.1 mg/mL, or, e.g., about 1 mg/mL of a moxifloxacin compound such as moxifloxacin hydrochloride.

In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of the component/excipient for such a component's/ingredient's intended purpose.

According to certain aspects, compositions comprise moxifloxacin plus one or more additional antimicrobial compounds, such as, e.g., one or more quinolone antibiotics, or specifically one or more fluoroquinolone antibiotics, including, e.g., one or more of ofloxacin, ciprofloxacin, fleroxacin, lomefloxacin, nadifloxacin, norfloxacin, pefloxacin, rufloxacin, balofloxacin, grepafloxacin, levofloxacin, pazufloxacin, sparfloxacin, temafloxacin, clinafloxacin, gatifloxacin, sitafloxacin, prulifloxacin, besifloxacin, gemifloxacin, and delafloxacin.

Gatifloxacin

In certain aspects, compositions provided by the invention comprise, e.g., a quinolone antibiotic component of compositions provided by the invention comprise, a gatifloxacin compound. Gatifloxacin compounds can exhibit inhibition of DNA gyrase, an enzyme involved in DNA replication, transcription and repair, and inhibition of topoisomerase IV, an enzyme involved in partitioning of chromosomal DNA during bacterial cell division.

In aspects, the invention provides ophthalmic compositions comprising one or more ophthalmologically suitable compounds which, when delivered to the eye of a subject in sufficient amounts, result in detectable or significant antimicrobial properties (that is, provide detectable or significant inhibition of growth of one or more microbes,) approximately the same or significantly similar to those typically provided by a corresponding amount of gatifloxacin or that provide an improvement on such effects. In aspects, such compositions comprise one or more gatifloxacin compounds. In aspects, one or more of such gatifloxacin compounds also provide therapeutic effects significantly similar to, or that improve upon, therapeutic effects associated with gatifloxacin in similar application and amount. In aspects, gatifloxacin compounds are mostly, generally, or only composed of gatifloxacin, rather than an analog or derivative thereof. In aspects, gatifloxacin compounds comprise, mostly comprise, or only comprise one or more suitable gatifloxacin analogs or derivatives such as, e.g., those described by Sriram, et. al., in "Gatifloxacin derivatives: synthesis, antimycobacterial activities, and inhibition of Mycobacterium tuberculosis DNA gyrase," Bioorg Med Chem Lett. 2006 Jun. 1; 16(11):2982-5; by Gomez, et. al., in "Synthesis of gatifloxacin derivatives and their biological activities against Mycobacterium leprae and Mycobacterium tuberculosis," Bioorg Med Chem. 2013 Feb. 15; 21(4):948-56; and, e.g., by de Almeida M V, et. al., in "Synthesis and antitubercular activity of lipophilic moxifloxacin and gatifloxacin derivatives," Bioorg Med Chem letters, 17, 5661-5664(2007).

In aspects, compositions provided by the invention comprise any form of ophthalmologically suitable gatifloxacin compound, such as, e.g., any pharmaceutically acceptable derivative, prodrug, hydrate, salt, solvate, enantiomer, or polymorph thereof. In aspects, gatifloxacin compounds of the compositions provided by the invention comprise any ophthalmologically suitable analog or derivative of gatifloxacin. In aspects, compositions provided by the invention comprise a single type of gatifloxacin compound, while in alternative aspects, compositions provided by the invention comprise ≥2 types of gatifloxacin compounds e.g., two different derivatives of gatifloxacin, each differing from the other in, e.g., their compound size, level of detectable effect (e.g., microbial inhibition activity), pKa value, etc.

In certain aspects, compositions provided by the invention comprise a salt of gatifloxacin. In aspects, most, generally all, or all of the gatifloxacin compound(s) comprise gatifloxacin ((±)-1-cyclopropyl-6-fluoro-1, 4-dihydro-8-methoxy-7-(3-methyl-1-piperazinyl)-4-oxo-3-quinolinecarboxylic acid sesquihydrate), in one or more salt forms.

Gatifloxacin Amount

According to aspects, the invention provides an ophthalmologically suitable composition comprising an effective amount of gatifloxacin compound(s), such as, e.g., gatifloxacin, wherein the ophthalmologically suitable gatifloxacin compound is present in the composition in an amount of between about 0.01-2 wt. % such as, e.g., between ~0.01-~1.9 wt. %, ~0.01-1.8 wt. %, ~0.01-~1.7 wt. %, ~0.01-~1.6 wt. %, ~0.01-~1.5 wt. %, ~0.01-~1.4 wt. %, ~0.01-~1.3 wt. %, ~0.01-~1.2 wt. %, ~0.01-~1.1 wt. %, ~0.01-~1 wt. %, ~0.01-~0.9 wt. %, ~0.01-~0.8 wt. %, ~0.01-~0.7 wt. %, ~0.01-~0.6 wt. %, ~0.01-~0.5 wt. %, ~0.01-~0.4 wt. %, ~0.01-~0.3 wt. %, ~0.01-~0.2 wt. %, ~0.01-~0.1 wt. % such as, e.g., between ~0.02-~2 wt. %, ~0.03-~2 wt. %, ~0.04-~2 wt. %, ~0.05-~2 wt. %, ~0.06-~2 wt. %, ~0.07-~2 wt. %, ~0.08-~2 wt. %, ~0.09-~2 wt. %, ~1-2 wt. %, ~1.1-~2 wt. %, ~1.2-~2 wt. %, ~1.3-~2 wt. %, ~1.4-~2 wt. %, ~1.5-~2 wt. %, ~1.6-~2 wt. %, ~1.7-~2 wt. %, ~1.8-~2 wt. %, ~1.9-~2 wt. %, as in, for example, between ~0.02-~1.9 wt. %, ~0.03-~1.8 wt. %, ~0.04-~1.7 wt. %, ~0.05-~1.6 wt. %, ~0.06-~1.5 wt. %, ~0.07-~1.4 wt. %, ~0.08-~1.3 wt. %, ~0.09-~1.2 wt. %, ~0.1-~1.1 wt. %, ~0.2-~1 wt. %, ~0.3-~0.9 wt. %, ~0.4-~0.8 wt. %, ~0.4-~0.7 wt. %, ~0.4-~0.6 wt. % or, e.g., about 0.5 wt. %.

In aspects, compositions comprise between about 1-10 mg/mL of a gatifloxacin compound, such as, e.g., between ~1-~9.5 mg/mL, ~1-9 mg/mL, ~1-~8.5 mg/mL, ~1-~8 mg/mL, ~1-~7.5 mg/mL, ~1-~7 mg/mL, ~1-~6.5 mg/mL, ~1-~6 mg/mL, ~1-~5.5 mg/mL, ~1-~5 mg/mL, ~1-~4.5 mg/mL, ~1-~4 mg/mL, ~1-~3.5 mg/mL, ~1-~3 mg/mL, ~1-~2.5 mg/mL, ~1-~2 mg/mL, ~1-~1.5 mg/mL, such as, e.g. ~1.5-~10 mg/mL, ~2-~10 mg/mL, ~2.5-~10 mg/mL, ~3-~10 mg/mL, ~3.5-~10 mg/mL, ~4-~10 mg/mL, ~4.5-~10 mg/mL, ~5-~10 mg/mL, ~5.5-~10 mg/mL, ~6-~10 mg/mL, ~6.5-~10 mg/mL, ~7-~10 mg/mL, ~7.5-~10 mg/mL, ~8-~10 mg/mL, ~8.5-~10 mg/mL, ~9-~10 mg/mL, ~9.5-~10 mg/mL as in, for example, between ~1.5-~9.5 mg/mL, ~2-~9 mg/mL, ~2.5-~8.5 mg/mL, ~3-~8 mg/mL, ~3.5-~7.5 mg/mL, ~4-~7 mg/mL, ~4.5-6.5 mg/mL, ~4.5-~6 mg/mL, ~4.5-~5.5 mg/mL, or, e.g., about 5 mg/mL of a gatifloxacin compound.

In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of the component/excipient for such a component's/ingredient's intended purpose.

According to certain aspects, compositions comprise gatifloxacin compound(s) plus one or more additional antimicrobial compounds, such as, e.g., one or more quinolone antibiotics, or specifically one or more fluoroquinolone antibiotics, including, e.g., one or more of moxifloxacin, ofloxacin, ciprofloxacin, fleroxacin, lomefloxacin, nadifloxacin, norfloxacin, pefloxacin, rufloxacin, balofloxacin, grepafloxacin, levofloxacin, pazufloxacin, sparfloxacin, temafloxacin, clinafloxacin, sitafloxacin, prulifloxacin, besifloxacin, gemifloxacin, and delafloxacin.

Anti-Inflammatory Component

In aspects, compositions provided by the invention comprise one or more anti-inflammatory steroid components. In aspects, an anti-inflammatory steroid component comprises a therapeutically effective amount of one or more anti-inflammatory compounds. In aspects the anti-inflammatory compounds are any one or more ophthalmologically suitable anti-inflammatory compounds, such as an anti-inflammatory classified as a steroid, such as, in specific aspects a corticosteroid, or a non-steroid (NSAID). In aspects, an anti-inflammatory compound is any ophthalmologically suitable form of such compounds, such as, e.g., an ophthalmologically suitable salt, hydrate, solvate, ether, ester, acetal, prodrug, polymorph, and ketal thereof. Here, the term anti-inflammatory typically means a compound which DOS counteracts, e.g., suppresses or prevents, inflammation, but, as with all known terms, such a description is only meant to illustrate aspects and not to limit the scope of the term.

Steroids Including Corticosteroids & Glucocorticoids

In aspects, anti-inflammatory steroid components of compositions comprise one or more steroid anti-inflammatory constituents. In aspects, a steroid anti-inflammatory constituent is a corticosteroid anti-inflammatory compound constituent.

In aspects, steroidal anti-inflammatory agent(s)/compound(s) suitable for use in the compositions herein include can include an effective amount of any ophthalmologically suitable steroid anti-inflammatory agent, including, e.g., 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and, e.g., triamcinolone hexacetonide, and pharmaceutically acceptable salts thereof, and suitable mixtures of any or all thereof. Typically, a composition will comprise ≤5, ≤3, or ≤2 anti-inflammatory steroids. In aspects, a composition comprises ≤5, ≤3, or ≤2 anti-inflammatory agents/compounds, overall.

In aspects, the steroid, e.g., corticosteroid anti-inflammatory compound is any ophthalmologically suitable steroid, e.g., corticosteroid anti-inflammatory compounds demonstrating suitable therapeutic efficacy in treating inflammation or one or more conditions related to inflammation such as, e.g., redness, pain, discomfort, or the like. In aspects, a steroidal, e.g., corticosteroidal, compound is any ophthalmologically suitable derivative, salt, hydrate, solvate, ether, ester, acetal, or ketal thereof.

In aspects, a corticosteroid anti-inflammatory for use in the compositions herein include triamcinolone, prednisolone, methylprednisolone, betamethasone, dexamethasone, fluorometholone, fluocinolone, loteprednol, etc.

In aspects, compositions comprise between about 0.01-5 wt. % of a steroid anti-inflammatory compound, such as a corticosteroid compound, such as, e.g., between ~0.01-~4.5 wt. %, ~0.01-~4 wt. %, ~0.01-~3.5 wt. %, ~0.01-~3 wt. %, 0.01-2.5 wt. %, ~0.01-2 wt. %, ~0.01-1.5 wt. %, ~0.01-~1 wt. %, ~0.01-~0.5 wt. % such as, e.g., between ~0.5-~5 wt. %, ~1-~5 wt. %, ~1.5-~5 wt. %, ~2-~5 wt. %, ~2.5-~5 wt. %, ~3-~5 wt. %, ~3.5-~5 wt. %, ~4-~5 wt. %, ~4.5-~5 wt. %, as in, for example, between ~0.02-~4.5 wt. %, ~0.04-~4 wt. %, ~0.6-~3.5 wt. %, ~0.8-~3 wt. %, ~1-~2.5 wt. %, ~1.2-~2 wt. %, ~1.2-~1.8 wt. %, or, e.g., ~1.2-~1.6 wt. %, such as, e.g., about 1.5 wt. % of a steroid anti-inflammatory compound. In aspects, the steroid anti-inflammatory compound is a corticosteroid compound.

In aspects, compositions comprise between about 1-50 mg/mL of a steroid anti-inflammatory compound, such as a corticosteroid compound, e.g., between ~1-~45 mg/mL, ~1-~40 mg/mL, ~1-~35 mg/mL, ~1-~30 mg/mL, ~1-~25 mg/mL, ~1-~20 mg/mL, such as ~1-15 mg/mL, as in, e.g., between ~5-~50 mg/mL, ~10-~50 mg/mL, or ~15-~50 mg/mL, as in, for example, between ~5-~45 mg/mL, ~6-~40 mg/mL, ~7-~35 mg/mL, ~8-~30 mg/mL, ~9-~25 mg/mL, ~10-~20 mg/mL, ~12-~18 mg/mL, ~14-~16 mg/mL, or, e.g., about 15 mg/mL of a steroid anti-inflammatory compound. In aspects, the steroid anti-inflammatory compound is a corticosteroid compound.

Triamcinolone

In certain aspects, compositions provided by the invention comprise, e.g., an anti-inflammatory steroid component of compositions provided by the invention comprise, mostly comprise, generally consist of, or consist of an ophthalmologically suitable derivative of prednisolone. In aspects, the derivative of prednisolone is a triamcinolone compound. In aspects, a triamcinolone compound is one of less than 5, such as one of 2 or 3 anti-inflammatory compounds or anti-inflammatory steroids in a composition.

In aspects, the anti-inflammatory agent is a triamcinolone compound. A triamcinolone compound will comprise triamcinolone or a similar compound that exhibits DOS synthetic similar immunosuppressive and anti-inflammatory activity as to triamcinolone (e.g., activation of the glucocorticoid receptor, preventing the synthesis of prostaglandins and leukotrienes, inhibiting pro-inflamatory cytokines such as interleukin IL-1 and IL-6, inhibiting activation of T-lymphocytes, or a combination of any or all thereof. In aspects, the triamcinolone compound is any ophthalmologically suitable triamcinolone compound such as any ophthalmologically suitable derivative, salt, solvate, hydrate, enantiomer, polymorph, or prodrug thereof. In aspects, the triamcinolone compound is triamcinolone acetonide (9-Fluoro-11β, 16α, 17, 21-tetrahydroxypregna-1, 4-diene-3, 20-dione cyclic 16, 17-acetal with acetone).

Triamcinolone Amount

According to aspects, the invention provides an ophthalmologically suitable composition comprising an effective amount of triamcinolone compound(s), such as, e.g., triamcinolone acetonide, wherein the ophthalmologically suitable triamcinolone compound is present in the composition in an amount of between about 0.01-5 wt. %, such as, e.g., between ~0.01-~4.5 wt. %, ~0.01-~4 wt. %, ~0.01-~3.5 wt. %, ~0.01-~3 wt. %, 0.01-2.5 wt. %, ~0.01-2 wt. %, ~0.01-1.5 wt. %, ~0.01-~1 wt. %, ~0.01-~0.5 wt. % such as, e.g., between ~0.5-~5 wt. %, ~1-~5 wt. %, ~1.5-~5 wt. %, ~2-~5 wt. %, ~2.5-~5 wt. %, ~3-~5 wt. %, ~3.5-~5 wt. %, ~4-~5 wt. %, ~4.5-~5 wt. %, as in, for example, between ~0.02-~4.5 wt. %, ~0.04-~4 wt. %, ~0.6-~3.5 wt. %, ~0.8-~3 wt. %, ~1-~2.5 wt. %, ~1.2-~2 wt. %, ~1.2-~1.8 wt. %, or, e.g. ~1.2-~1.6 wt. %, such as, e.g., about 1.5 wt. %. In aspects, the triamcinolone compound is triamcinolone acetonide.

In aspects, compositions comprise between about 1-50 mg/mL of a triamcinolone compound, such as, e.g., triamcinolone acetonide, such as in an amount between ~1-~45 mg/mL, ~1-~40 mg/mL, ~1-~35 mg/mL, ~1-~30 mg/mL, ~1-~25 mg/mL, ~1-~20 mg/mL, such as ~1-15 mg/mL, as in, e.g., between ~5-~50 mg/mL, ~10-~50 mg/mL, or ~15-~50 mg/mL, as in, for example, between ~5-~45 mg/mL, ~6-~40 mg/mL, ~7-~35 mg/mL, ~8-~30 mg/mL, ~9-~25 mg/mL, ~10-~20 mg/mL, ~12-~18 mg/mL, ~14-~16 mg/mL, or, e.g., about 15 mg/mL of a triamcinolone compound. In aspects, the triamcinolone compound is triamcinolone acetonide.

In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of the component/excipient for such a component's/ingredient's intended purpose.

According to aspects, compositions comprise triamcinolone plus one or more additional anti-inflammatory agents, such as any one or more anti-inflammatory agents described herein, including steroidal or NSAID anti-inflammatory agents.

Prednisolone

In certain aspects, compositions provided by the invention comprise, e.g., an anti-inflammatory steroid component of compositions provided by the invention comprise, mostly comprise, generally consist of, consist essentially of, or consist of a prednisolone compound. In aspects, a prednisolone compound is one of less than 5, such as one of 2 or 3 anti-inflammatory compounds or anti-inflammatory steroids in a composition. In aspects, a prednisolone compound will have at least two times, at least three, or even about five times or more of the anti-inflammatory potency of hydrocortisone. In aspects, a prednisolone compound DOS inhibits edema and fibrin disposition, phagocytic migration, capillary proliferation and deposition of collagen and scar tissue. In aspects, the prednisolone compound is any ophthalmologically suitable prednisolone compound such as any ophthalmologically suitable derivative, salt, solvate, hydrate, enantiomer, polymorph, or prodrug thereof. In aspects, prednisolone derivatives can comprise, e.g., rimexolone, difluprednate, various hydroxylation-related modifications of prednisolone (see, e.g., Mohamed, et. al. in "Biotransformation of prednisolone to hydroxy derivatives by *Penicillium aurantiacum*," Biocat and Biotrans, 23 Apr. 2017, pp 215-222); modifications to prednisolone on the cyclic acetal ring, such as those described in DE4129535; further modifications to such derivatives at the C-21 hydroxy group as is described in, e.g., U.S. Pat. No. 5,733,901 (Gutterer); modifications at the 16- and 17-carbon positions as is described by, e.g., Lee, et. al. in "New steroidal anti-inflammatory agents: prednisolone derivatives with an isooxazoline fusion at the 16- and 17-carbons and an alkyl carboxylate at the 16 alpha-position," Drugs Eps Clin Res. 1998; 24(2):57-66, etc. In aspects, a prednisolone compound does not include triamcinolone or a compound that is more structurally related to triamcinolone than prednisolone. In aspects, the prednisolone compound is prednisolone acetate ([2-[(8S,9S,10R,11S, 13S,14S,17R)-11,17-Dihydroxy-10,13-dimethyl-3-oxo-7,8,9,11,12,14,15,16-octahydro-6H-cyclopenta[a]phenanthren-17-yl]-2-oxoethyl] acetate).

Prednisolone Amount

According to aspects, the invention provides an ophthalmologically suitable composition comprising an effective amount of prednisolone compound(s), such as, e.g., prednisolone acetate, wherein the ophthalmologically suitable prednisolone compound is present in the composition in an amount of between about 0.01-5 wt. %, such as, e.g., between ~0.01-~4.5 wt. %, ~0.01-~4 wt. %, ~0.01-~3.5 wt. %, ~0.01-~3 wt. %, 0.01-2.5 wt. %, ~0.01-2 wt. %, ~0.01-1.5 wt. %, ~0.01-~1 wt. %, ~0.01-~0.5 wt. % such as, e.g., between ~0.5-~5 wt. %, ~1-~5 wt. %, ~1.5-~5 wt. %, ~2-~5 wt. %, ~2.5-~5 wt. %, ~3-~5 wt. %, ~3.5-~5 wt. %, ~4-~5 wt. %, ~4.5-~5 wt. %, as in, for example, between ~0.02-~4.5 wt. %, ~0.04-~4 wt. %, ~0.6-~3.5 wt. %, ~0.8-~3 wt. %, ~1-~2.5 wt. %, ~1.2-~2 wt. %, ~1.2-~1.8 wt. %, or, e.g. ~1.2-~1.6 wt. %, such as, e.g., about 1.5 wt. %. In aspects, the prednisolone compound is prednisolone acetate.

In aspects, compositions comprise between about 1-50 mg/mL of a prednisolone compound, such as, e.g., prednisolone acetate, such as an amount of between ~1-~45 mg/mL, ~1-~40 mg/mL, ~1-~35 mg/mL, ~1-~30 mg/mL, ~1-~25 mg/mL, ~1-~20 mg/mL, such as ~1-15 mg/mL, as in, e.g., between ~5-~50 mg/mL, ~10-~50 mg/mL, or ~15-~50 mg/mL, as in, for example, between ~5-~45 mg/mL, ~6-~40 mg/mL, ~7-~35 mg/mL, ~8-~30 mg/mL, ~9-~25 mg/mL, ~10-~20 mg/mL, ~12-~18 mg/mL, ~14-~16 mg/mL, or, e.g., about 15 mg/mL of a prednisolone compound. In aspects, the prednisolone compound is prednisolone acetate.

In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of the component/excipient for such a component's/ingredient's intended purpose.

According to aspects, compositions comprise prednisolone plus one or more additional anti-inflammatory agents, such as any one or more anti-inflammatory agents described herein, including steroidal or non-steroidal anti-inflammatory agents. In aspects, compositions comprise prednisolone plus one or more additional non-steroidal agents. In aspects, compositions comprise prednisolone plus bromfenac.

Loteprednol

In certain aspects, compositions provided by the invention comprise, e.g., an anti-inflammatory steroid component of compositions provided by the invention comprise, mostly comprise, generally consist of, consist essentially of, or consist of a loteprednol compound. In aspects, a loteprednol compound is one of less than 5, such as one of 2 or 3 anti-inflammatory compounds or anti-inflammatory steroids in a composition. In aspects, a loteprednol compound can be characterized on the basis of being at least 2, at least 3, or all of the following—a 17alpha-hydroxy steroid, an androstanoid, an organochlorine compound, a steroid acid ester, or a 3-oxo-Delta(1), Delta(4)-steroid, and exhibits corticosteroid hormone receptor agonist activity. In aspects, the loteprednol compound is any ophthalmologically suitable loteprednol compound such as any ophthalmologically suitable derivative, salt, solvate, hydrate, enantiomer, polymorph, or prodrug thereof. In aspects, the loteprednol compound is loteprednol etabonate. Loteprednol etabonate is the etabonate salt form of loteprednol.

Loteprednol Amount

According to aspects, the invention provides an ophthalmologically suitable composition comprising an effective amount of loteprednol compound(s), such as, e.g., loteprednol etabonate, wherein the ophthalmologically suitable loteprednol compound is present in the composition in an amount of between about 0.01-5 wt. %, such as, e.g., between ~0.01-~4.5 wt. %, ~0.01-~4 wt. %, ~0.01-~3.5 wt. %, ~0.01-~3 wt. %, 0.01-2.5 wt. %, ~0.01-2 wt. %, ~0.01-1.5 wt. %, ~0.01-~1 wt. %, ~0.01-~0.5 wt. % such as, e.g., between ~0.5-~5 wt. %, ~1-~5 wt. %, ~1.5-~5 wt. %, ~2-~5 wt. %, ~2.5-~5 wt. %, ~3-~5 wt. %, ~3.5-~5 wt. %, ~4-~5 wt. %, ~4.5-~5 wt. %, as in, for example, between ~0.02-~4.5 wt. %, ~0.04-~4 wt. %, ~0.6-~3.5 wt. %, ~0.8-~3 wt. %, ~1-~2.5 wt. %, ~1.2-~2 wt. %, ~1.2-~1.8 wt. %, or, e.g. ~1.2-~1.6 wt. %, such as, e.g., about 1.5 wt. %. In aspects, the loteprednol compound is loteprednol etabonate.

In aspects, compositions comprise between about 1-50 mg/mL of a loteprednol compound, such as, e.g., loteprednol etabonate, such as an amount of between ~1-~45 mg/mL, ~1-~40 mg/mL, ~1-~35 mg/mL, ~1-~30 mg/mL, ~1-~25 mg/mL, ~1-~20 mg/mL, such as ~1-15 mg/mL, as in, e.g., between ~5-~50 mg/mL, ~10-~50 mg/mL, or ~15-~50 mg/mL, as in, for example, between ~5-~45 mg/mL, ~6-~40 mg/mL, ~7-~35 mg/mL, ~8-~30 mg/mL, ~9-~25 mg/mL, ~10-~20 mg/mL, ~12-~18 mg/mL, ~14-~16 mg/mL, or, e.g., about 15 mg/mL of a loteprednol compound. In aspects, the loteprednol compound is loteprednol etabonate.

In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of the component/excipient for such a component's/ingredient's intended purpose.

According to aspects, compositions comprise loteprednol plus one or more additional anti-inflammatory agents, such as any one or more anti-inflammatory agents described herein, including steroidal or non-steroidal anti-inflammatory agents.

Non-Steroid

In aspects, compositions comprise, e.g., an anti-inflammatory steroid component of a composition comprises, e.g., one or more non-steroidal anti-inflammatory constituents (agents, compounds). The term "constituents" is sometimes used in this disclosure to refer to ingredients of a composition. Uncontradicted, it has the same meaning as agent/compound. In some aspects, anti-inflammatory steroid component(s) comprise at least one steroidal anti-inflammatory constituent and at least one non-steroidal anti-inflammatory constituent.

In one aspect, the invention provides compositions comprising one or more pharmaceutically acceptable and ophthalmologically suitable non-steroidal anti-inflammatory compounds, such as, e.g., aspirin, benoxaprofen, benzofenac, bromfenac, bucloxic acid, butibufen, carprofen, cicloprofen, cinmetacin, clidanac, clopirac, diclofenac, difluprednate, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketoprofen, lactorolac, lonazolac, metiazinic, miroprofen, nepafenac, naproxen, norketotifen, oxaprozin, oxepinac, phenacetin, pirprofen, pirazolac, protizinic acid, sulindac, suprofen, tiaprofenic acid, tolmetin, and, e.g., zomepirac, and pharmaceutically acceptable salts thereof, and mixtures thereof.

In aspects, anti-inflammatory steroid components of compositions provided by the invention comprise non-steroidal anti-inflammatory compound(s) in an amount representing between about 0.01-0.2 wt. % of the composition, such as, e.g., between ~0.01-0.1 wt. %, ~0.01-~0.09 wt. %, ~0.01-~0.08 wt. %, ~0.01-~0.07 wt. %, ~0.01-0.06% wt. %, ~0.01-0.05 wt. %, ~0.01-0.04 wt. %, ~0.01-0.03 wt. %, ~0.01-~0.02 wt. %, such as, e.g., between ~0.02-~0.2 wt. %, ~0.03-~0.2 wt. %, ~0.04-~0.2 wt. %, ~0.05-~0.2 wt. %, ~0.06-~0.2 wt. %, ~0.07-~0.2 wt. %, ~0.08-~0.2 wt. %, ~0.09-~0.2 wt. %, ~0.1-~0.2 wt. %, as in, for example, between ~0.02-~0.19 wt. %, ~0.03-~0.18 wt. %, ~0.04-~0.17 wt. %, ~0.05-~0.16 wt. %, ~0.06-~0.15 wt. %, ~0.07-~0.14 wt. %, ~0.08-~0.13 wt. %, ~0.08-~0.12 wt. %, ~0.08-~0.11 wt. %, ~0.08-~0.1 wt. %, or, e.g., about 0.09 wt. % of a non-steroidal anti-inflammatory compound.

In aspects, compositions comprise between about 0.1-2 mg/mL of a non-steroidal anti-inflammatory compound, such as, e.g., between ~0.1-~1.9 mg/mL, ~0.1-~1.8 mg/mL, ~0.1-~1.7 mg/mL, ~0.1-~1.6 mg/mL, ~0.1-~1.5 mg/mL, ~0.1-~1.4 mg/mL, ~0.1-1.3 mg/mL, ~0.1-~1.2 mg/mL, ~0.1-~1.1 mg/mL, ~0.1-~1 mg/mL, ~0.1-~0.9 mg/mL, or, such as, e.g., between ~0.2-~2 mg/mL, ~0.3-~2 mg/mL, ~0.4-~2 mg/mL, ~0.5-~2 mg/mL, ~0.6-~2 mg/mL, ~0.7-~2 mg/mL, ~0.8-~2 mg/mL, ~0.9-~2 mg/mL, as in, for example, between ~0.2-~1.9 mg/mL, ~0.3-~1.8 mg/mL, ~0.4-~1.7 mg/mL, ~0.5-~1.6 mg/mL, ~0.6-1.5 mg/mL, ~0.7-~1.4 mg/mL, ~0.8-~1.3 mg/mL, ~0.8-~1.2 mg/mL, ~0.08-~1.1 mg/mL, ~0.08-~1 mg/mL, or, e.g., about 0.9 mg/mL of a non-steroidal anti-inflammatory compound.

Bromfenac

In aspects, compositions provided by the invention comprise, e.g., an anti-inflammatory steroid component of compositions provided by the invention comprise, a bromfenac compound. In aspects, the bromfenac compound is a non-steroidal anti-inflammatory drug (NSAID) with analgesic and anti-inflammatory activities that binds to and inhibits the activity of cyclooxygenase II (COX II), thereby inhibiting prostaglandin formation. In aspects, an effective amount of a bromfenac compounds DOS prevents vasodilation, leukocytosis, disruption of the blood-aqueous humor barrier, an increase in vascular permeability and an increase in intraocular pressure (IOP). In aspects, the bromfenac compound is any ophthalmologically suitable bromfenac compound such as any ophthalmologically suitable derivative, salt, solvate, hydrate, enantiomer, polymorph, or prodrug thereof. In aspects, the bromfenac compound is bromfenac sodium sesquihydrate. In aspects, the bromfenac compound is bromfenac sodium salt sesquihydrate (the sesquihydrate of the sodium salt of bromfenac) (disodium;2-[2-amino-3-(4-bromobenzoyl)phenyl]acetate;trihydrate).

Bromfenac Amount

In aspects, anti-inflammatory steroid components of compositions provided by the invention comprise a bromfenac compound, such as, e.g., bromfenac sodium sesquihydrate in an amount representing between about 0.01-0.2 wt. % of the composition, such as, e.g., between ~0.01-0.1 wt. %, ~0.01-0.09 wt. %, ~0.01-~0.08 wt. %, ~0.01-~0.07 wt. %, ~0.01-0.06% wt. %, ~0.01-0.05 wt. %, ~0.01-0.04 wt. %, ~0.01-0.03 wt. %, ~0.01-~0.02 wt. %, such as, e.g., between ~0.02-~0.2 wt. %, ~0.03-~0.2 wt. %, ~0.04-~0.2 wt. %, ~0.05-~0.2 wt. %, ~0.06-~0.2 wt. %, ~0.07-~0.2 wt. %, ~0.08-~0.2 wt. %, ~0.09-~0.2 wt. %, ~0.1-~0.2 wt. %, as in, for example, between ~0.02-~0.19 wt. %, ~0.03-~0.18 wt. %, ~0.04-~0.17 wt. %, ~0.05-~0.16 wt. %, ~0.06-~0.15 wt. %, ~0.07-~0.14 wt. %, ~0.08-~0.13 wt. %, ~0.08-~0.12 wt. %, ~0.08-~0.11 wt. %, ~0.08-~0.1 wt. %, or, e.g., about 0.09 wt. % of a bromfenac compound. In aspects, the bromfenac compound is bromfenac sodium sesquihydrate.

In aspects, compositions comprise between about 0.1-2 mg/mL of a bromfenac compound, such as bromfenac sodium sesquihydrate, such as, e.g., between ~0.1-~1.9 mg/mL, ~0.1-~1.8 mg/mL, ~0.1-~1.7 mg/mL, ~0.1-~1.6 mg/mL, ~0.1-~1.5 mg/mL, ~0.1-~1.4 mg/mL, ~0.1-~1.3 mg/mL, ~0.1-~1.2 mg/mL, ~0.1-~1.1 mg/mL, ~0.1-~1 mg/mL, ~0.1-~0.9 mg/mL, or, such as, e.g., between ~0.2-~2 mg/mL, ~0.3-~2 mg/mL, ~0.4-~2 mg/mL, ~0.5-~2 mg/mL, ~0.6-~2 mg/mL, ~0.7-~2 mg/mL, ~0.8-~2 mg/mL, ~0.9-~2 mg/mL, as in, for example, between ~0.2-~1.9 mg/mL, ~0.3-~1.8 mg/mL, ~0.4-~1.7 mg/mL, ~0.5-~1.6 mg/mL, ~0.6-~1.5 mg/mL, ~0.7-~1.4 mg/mL, ~0.8-~1.3 mg/mL, ~0.8-~1.2 mg/mL, ~0.08-~1.1 mg/mL, ~0.08-~1 mg/mL, or, e.g., about 0.9 mg/mL of a bromfenac compound. In aspects, the bromfenac compound is bromfenac sodium sesquihydrate.

In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of the component/excipient for such a component's/ingredient's intended purpose.

According to aspects, compositions comprise bromfenac plus one or more additional anti-inflammatory agents, such as any one or more anti-inflammatory agents described herein, including steroidal or non-steroidal anti-inflammatory agents. In aspects, compositions comprise bromfenac plus one or more additional steroidal agents. In aspects, compositions comprise bromfenac plus prednisolone.

Antimicrobial+Anti-Inflammatory Compounds

In aspects, compositions comprise both a therapeutically effective amount of a quinolone antibiotic component and a therapeutically effective amount of an anti-inflammatory steroid component. In aspects, compositions comprise a therapeutically effective amount of a broad-spectrum quinolone antibiotic component, such as, e.g., in specific aspects a broad-spectrum antibiotic compound, and a therapeutically effective amount of one or more steroidal or non-steroidal agents.

In aspects, compositions comprise therapeutically effective amounts of at least one ophthalmologically suitable fluoroquinolone antibiotic compound and at least on ophthalmologically suitable corticosteroid compound, or ophthalmologically suitable salts, hydrates, solvates, ethers, esters, acetal, and ketals thereof. In aspects, compositions can be characterized by the ratios of one component or compound to another component or compound, such as, e.g., a quinolone antibiotic component constituent(s) to an anti-inflammatory component constituent(s) (such as, for example, a corticosteroid constituent). In aspects, compositions provide a quinolone antibiotic component and an anti-inflammatory component in fixed amounts, such as, e.g., specific ratios. In aspects, compositions are reproducibly produced, and quality screened for the presence of such amounts of such APIs prior to packaging, use, etc.

In aspects, the fluoroquinolone antibiotic compound is a moxifloxacin compound or a gatifloxacin compound. In aspects, the corticosteroid component is a triamcinolone compound, a prednisolone compound, or a loteprednol compound. In aspects, an anti-inflammatory component constituent can be a non-steroidal anti-inflammatory compound, such as, e.g., a bromfenac compound. In aspects, compositions comprise therapeutically effective amounts of moxifloxacin hydrochloride or gatifloxacin, and one or more of triamcinolone acetonide, prednisolone acetate, and bromfenac sodium sesquihydrate.

Table 1 below provides exemplary composition ingredients, exemplary ranges of such ingredients, and exemplary ratios between them. In aspects, compositions comprise exemplified ingredients in such exemplified ratios.

TABLE 1

Exemplary Ingredients & Ratios.

| Description | Name | Exemplary range |
|---|---|---|
| Fluoroquinolone antibiotic | Moxifloxacin | 0.1-5 mg/mL |
| Fluoroquinolone antibiotic | Gatifloxacin | 1-10 mg/mL |
| Steroid anti-inflammatory | Triamcinolone | 1-50 mg/mL |
| Steroid anti-inflammatory | Prednisolone | 1-50 mg/mL |
| Steroid anti-inflammatory | Loteprednol | 1-50 mg/mL |
| Non-steroid anti-inflammatory | Bromfenac | 0.5-1 mg/mL |
| Non-ionic suspension agent | PEG 3350 | 10-100 mg/mL |
| Non-ionic suspension agent | CMC | 2-20 mg/mL |
| Ionic suspension agent | Hyaluronic acid | 2-20 mg/mL |
| Non-ionic suspension agent present with one or more additional suspension agents) | PS-80 | 5-15 mg/mL |
| Total Suspension Agent | — | 7-115 mg/mL |

Exemplary Ratios:

| | |
|---|---|
| Moxifloxacin:Suspension Component | 1:1.4-1:1150 |
| Gatifloxacin:Suspension Component | 1:0.7-1:115 |
| Fluroquinolone:Suspension Component | 1:0.7-1:1150 |
| Fluoroquinolone:Ionic Suspension Component | 1:0.5-1:200 |
| Fluoroquinolone:Non-ionic Suspension Component | 1:0.7-1:1150 |
| Steroid Anti-Inflammatory:Suspension Component | 1:0.14-1:115 |
| Ionic Suspension Agent:Non-Ionic Suspension Agent | 1:0.35-1:57.5 |
| Total API:Suspension Component | 1:0.9-1:105 |

In aspects, compositions comprise a ratio of fluoroquinolone antibiotic compound:suspension component of between about 1.07-about 1:1150, such as, e.g., between about 1:0.7-about 1:115.

In aspects, compositions comprise a ratio of fluoroquinolone antibiotic compound:ionic suspension component of between about 1:0.5-about 1:200, such as, e.g., between about 1:100-about 1:1.

In aspects, compositions comprise a ratio of fluoroquinolone antibiotic compound:non-ionic suspension component of between about 1:0.7-about 1:1150, such as, e.g., 1:1.2-about 1:1100.

In aspects, compositions comprise a ratio of steroid anti-inflammatory compound:suspension component of between about 1:0.14-about 1:115, such as, e.g., between about 1:0.24-about 1:115.

In aspects, compositions comprise a moxifloxacin compound and a suspension component, wherein the ratio of the moxifloxacin to the suspension component, is, e.g., between about 1:40-about 1:1, such as, e.g., between ~1:38-~1:4, ~1:36-~1:8, ~1:34-~1:10, or, e.g., ~1:36-~1:12, such as, e.g., between about 1:30-1:2. In aspects, compositions comprise a moxifloxacin compound an ionic suspension agent, wherein the ratio of the moxifloxacin compound to the ionic suspension agent is between about 1:30-about 1:1, or, e.g., 1:20-~1:2. In aspects, compositions comprise a moxifloxacin compound and a non-ionic suspension agent, wherein the ratio of the moxifloxacin compound to the non-ionic suspension agent is, e.g., between about 1:20-about 1:2, such as, e.g., between about 1:5-about 1:4, such as, e.g., ~1:12-~1:8, such as, e.g., about 1:10. In aspects, compositions comprise a non-ionic suspension agent and an ionic suspension agent, wherein the ratio of the non-ionic suspension agent to the ionic suspension agent is between ~1:10-about 1:0.1, e.g., about 1:9-about 1:0.2 (or, e.g., stated alternatively about 5:1), or, e.g., about 1:8-about 1:0.25 (or, stated alternatively, about 4:1).

In aspects, compositions comprise a gatifloxacin compound and a suspension component, wherein the ratio of the gatifloxacin to the suspension component, is, e.g., between about 1:10-about 1:0.1, e.g., ~1:8-~1:1, ~1:7-~1:2, or, e.g., ~1:6-~1:3. In aspects, compositions comprise a gatifloxacin compound an ionic suspension agent, wherein the ratio of the gatifloxacin compound to the ionic suspension agent is between about 1:6-about 1:0.8, e.g., ~1:5-~1:0.6, or, e.g., ~1:4-~1:0.4. In aspects, compositions comprise a gatifloxacin compound and a non-ionic suspension agent, wherein the ratio of the gatifloxacin compound to the non-ionic suspension agent is, e.g., between about 1:4-about 1:1, e.g., ~1:3-about 1:1, ~1:2.5-~1:1, such as, e.g., ~1:2. In aspects, compositions comprise a non-ionic suspension agent and an ionic suspension agent, wherein the ratio of the non-ionic suspension agent to the ionic suspension agent is between ~1:10-about 1:0.1, e.g., about 1:9-about 1:0.2 (or, e.g., stated alternatively about 5:1), or, e.g., about 1:8-about 1:0.25 (or, stated alternatively, about 4:1).

In aspects, the quinolone antibiotic component present within a composition does not detectably or significantly impact the efficacy, e.g., the anti-inflammatory activity or effect, of the anti-inflammatory steroid component of the composition. In aspects, the anti-inflammatory steroid component present within the composition does not detectably or significantly impact the efficacy, e.g., the antimicrobial inhibition or killing strength or activity of, the quinolone antibiotic component of the composition. In aspects no quinolone antibiotic component constituent(s) in the composition(s) cause(s) a detectable or significant detrimental impact to the recipient, such as, e.g., one or more unintended side effect(s), e.g., due to the copresence of the quinolone antibiotic component and anti-inflammatory steroid component, and anti-inflammatory steroid component constituent(s) present in the composition(s) cause(s) a detectable or significant detrimental impact to the recipient, such as, e.g., one or more unintended side effects), e.g., due to the copresence of quinolone antibiotic component and anti-inflammatory steroid component.

The quinolone antibiotic component or the anti-inflammatory steroid component can enhance the activity of the other or, in aspects, can act synergistically in treating or preventing clinically significant levels of infection, irritation (e.g., pain, redness, swelling, itching, discomfort, discharge, etc.), or both related to an infectious ophthalmic condition. For example, in aspects, administering the two components together provide a detectable or significant increase in the level of inflammation associated with an ocular infection over that of either component administered alone (such as, e.g., by reducing the level of infection causing the inflammation and co-treating existing inflammation).

In aspects, compositions comprise between about 0.01-about 1 wt. %, such as, e.g., about 0.1 wt. % of a moxifloxacin compound, such as, e.g., moxifloxacin hydrochloride, and between about 0.01-about 5 wt. %, e.g., about 1.5 wt. % of a triamcinolone compound, such as, e.g., triamcinolone acetonide.

In aspects, compositions comprise between 0.01-about 1 wt. %, such as, e.g., about 0.1 wt. % of a moxifloxacin compound, such as, e.g., moxifloxacin hydrochloride, and between about 0.01-about 5 wt. %, e.g., about 1.5 wt. % of a prednisolone compound, such as, e.g., prednisolone acetate.

In aspects, compositions comprise between about 0.01-about 1 wt. %, such as, e.g., about 0.1 wt. % of a moxifloxacin compound, such as, e.g., moxifloxacin hydrochloride, and between about 0.01-about 5 wt. %, e.g., about 1.5 wt. % of a loteprednol compound, such as, e.g., loteprednol etabonate.

In aspects, compositions comprise between about 0.01-about 2 wt. %, such as, e.g., about 0.5 wt. % of a gatifloxacin compound, between about 0.01-about 5 wt. %, e.g., about 1.5 wt. % of a prednisolone compound, such as, e.g., prednisolone acetate, and between about 0.01-about 0.2 wt. %, such as, e.g., about 0.09 wt. % of a bromfenac compound, such as, e.g., bromfenac sodium sesquihydrate.

In aspects, compositions comprise between about 0.01-about 1 wt. %, such as, e.g., about 0.1 wt. % of a moxifloxacin compound, such as, e.g., moxifloxacin hydrochloride, between about 0.01-about 5 wt. %, e.g., about 1.5 wt. % of a prednisolone compound, such as, e.g., prednisolone acetate, and between about 0.01-about 0.2 wt. %, such as, e.g., about 0.09 wt. % of a bromfenac compound, such as, e.g., bromfenac sodium sesquihydrate.

In aspects, compositions herein comprise at least one fluoroquinolone antimicrobial compound and at least one steroid anti-inflammatory compound. In aspects, the fluoroquinolone compound is moxifloxacin or gatifloxacin. In aspects, the steroid anti-inflammatory compound is triamcinolone, prednisolone, or loteprednol.

In aspects, compositions comprise an amount of moxifloxacin of between about 0.01-about 1 wt. % (about 0.1-about 5 mg/mL), such as about 0.1 wt. % or about 1 mg/mL, and an amount of triamcinolone of between about 0.01-about 5 wt. % (about 1-about 50 mg/mL), such as about 1.5 wt. % or about 15 mg/mL. In aspects, compositions comprise an amount of moxifloxacin of between about 0.01-about 1 wt. % (about 0.1-about 5 mg/mL), such as about 0.1 wt. % or about 1 mg/mL, and an amount of prednisolone of between about 0.01-about 5 wt. % (about 1-about 50 mg/mL), such as about 1.5 wt. % or about 15 mg/mL. In aspects, compositions comprise an amount of moxifloxacin of between about 0.01-about 1 wt. % (about 0.1-about 5 mg/mL), such as about 0.1 wt. % or about 1 mg/mL, and an amount of loteprednol of between about 0.01-about 5 wt. % (about 1-about 50 mg/mL), such as about 1.5 wt. % or about 15 mg/mL. In aspects, compositions described in this paragraph can further comprise a non-steroid anti-inflammatory compound. In aspects, the non-steroid anti-inflammatory compound is bromfenac. In aspects, compositions here can comprise between about 0.1-about 0.1 wt. % (about 0.1-about 2 mg/mL), such as, e.g., about 0.09 wt. % or about 0.9 mg/L.

In aspects, compositions comprise an amount of gatifloxacin of between about 0.01-about 1 wt. % (about 1-about 10 mg/mL), such as about 0.5 wt. % or about 5 mg/mL, and an amount of triamcinolone of between about 0.01-about 5 wt. % (about 1-about 50 mg/mL), such as about 1.5 wt. % or about 15 mg/mL. In aspects, compositions comprise an amount of moxifloxacin of between about 0.01-about 1 wt. % (about 0.1-about 5 mg/mL), such as about 0.1 wt. % or about 1 mg/mL, and an amount of prednisolone of between about 0.01-about 5 wt. % (about 1-about 50 mg/mL), such as about 1.5 wt. % or about 15 mg/mL. In aspects, compositions comprise an amount of moxifloxacin of between about 0.01-about 1 wt. % (about 0.1-about 5 mg/mL), such as about 0.1 wt. % or about 1 mg/mL, and an amount of loteprednol of between about 0.01-about 5 wt. % (about 1-about 50 mg/mL), such as about 1.5 wt. % or about 15 mg/mL. In aspects, compositions described in this paragraph can further comprise a non-steroid anti-inflammatory compound. In aspects, the non-steroid anti-inflammatory compound is bromfenac. In aspects, compositions here can comprise between about 0.1-about 0.1 wt. % (about 0.1-about 2 mg/mL), such as, e.g., about 0.09 wt. % or about 0.9 mg/L.

Suspension Component

In aspects, compositions comprise one or more ophthalmologically suitable suspension component(s). In alternative aspects, compositions provided by the invention do not comprise any component characterizable as a suspension component. Herein, "suspension component" refers to a substance used in the ophthalmic compositions to DOS maintain the actives in suspension within the composition(s), typically such that the composition(s) remain suitable for ocular administration for a DOS enhanced period of time (as compared to a corresponding formulation lacking the suspension component). In aspects, a suspension component provides one or more functions other than suspension functionality, such as, e.g., providing DOS surfactant activity, DOS preservative activity, etc.

In aspects, a suspension component constituent is a surfactant or exhibits surface activity. E.g., in aspects a suspension component DOS reduces the interfacial tension between solid particles and a vehicle, e.g., between particles of one or more active ingredients (such as, e.g., between one or more anti-microbial component constituents, between one or more anti-inflammatory steroid component constituents, or both) and a vehicle such as water. In aspects, DOS reduction in interfacial tension between such particles and vehicle DOS promotes wetting and deflocculation of such particles. In aspects, a suspension component provides a DOS reduction in contact angle between particle(s) and vehicle which DOS increases dissolution of one or more active agents, such as, e.g., increasing dissolution of one or more active agents by, e.g., at least about 1%, ≥~1.5%, ≥~2%, ≥~2.5, ≥~3%, ≥~3.5%, ≥~4%, ≥~4.5%, ≥~5%, ≥~5.5%, ≥~6%, ≥~6.5%, ≥~7%, ≥~7.5%, ≥~8%, ≥~8.5%, ≥~9%, or, e.g., ≥~9.5%, ≥~10% or more. In aspects, as a result of increased dissolution, a DOS greater amount of active penetrates the eye and imparts DOS therapeutic effect than compositions lacking such a suspension component. In aspects, composition(s) comprising a suspension component such as those described here, e.g., in specific aspects hyaluronic acid, carboxymethyl cellulose (CMC), polysorbate-80, or a polyethoxylated castor oil (e.g., Cremophor® EL) or a related composition (e.g., a hydrogenated polyethoxylated castor oil (e.g., Cremophor® RH-40), or combinations thereof, DOS increase the quantity of one or more active agents (e.g., one or more antimicrobial agents such as a fluoroquinolone antibiotic, one or more anti-inflammatory agents such as a steroid or non-steroid anti-inflammatory agent, or a combination thereof) over compositions lacking such a suspension agent by at least ~1%, ≥~2.5, ≥~3.5%, ≥~4.5%, ≥~5%, ≥~6.5%, ≥~7.5%, ≥~9%, ≥~9.5%, ≥~10%, ≥~12.5%, ≥~15%, ≥~20%, ≥~25%, or ≥~33% (e.g., 5-100%, 5-75%, or 5-50% or 10-300%, 10-200%, 10-150%, 10-100%, 10-70%, 10-50%, or 10-40%).

In aspects, compositions provided by the invention comprise a suspension component comprising suspension agent(s). In aspects, the suspension agent is any ophthalmologically suitable suspension component capable of maintaining the ingredients of the composition in suspension such that the compositions remain suitable for ocular administration for a period of at least about, e.g., 1 month or more, such as, e.g., ≥~5 weeks, ≥~6 weeks, ≥~7 weeks, ≥~2 months (8 weeks), ≥~9 weeks, ≥~10 weeks, ≥~11 weeks, ≥~3 months (12 weeks) or more, such as ≥~4 months, ≥~5 months, ≥~6 months, ≥~7 months, ≥~8 months, ≥~9 months, ≥~10 months, ≥~11 months, or, e.g., ≥~12 months or more, such as ≥~18 months≥~2 years, ≥~32 months, or, e.g., ≥~3 years or more.

In aspects, a suitable suspension component is any suspension component capable of maintaining both the quinolone antibiotic component and anti-inflammatory agent together in suspension without detectable or significant clumping, flocculation, caking (cake formation), undesirable API reactions/degradation, or coagulation for a period of at least about, e.g., 1 month or more, such as, e.g., ≥~5 weeks, ≥~6 weeks, ≥~7 weeks, ≥~2 months (8 weeks), ≥~9 weeks, ≥~10 weeks, ≥~11 weeks, ≥~3 months (12 weeks) or more, such as ≥~4 months, ≥~5 months, ≥~6 months, ≥~7 months, ≥~8 months, ≥~9 months, ≥~10 months, ≥~11 months, or, e.g., ≥~12 months or more, such as ≥~18 months≥~2 years, ≥~32 months, or, e.g., ≥~3 years or more.

In aspects, a suspension component can comprise at least 1, such as, e.g., ≥2, ≥3, ≥4, or, e.g., ≥5 suspension constituents (agents). In aspects, compositions comprise a suspension component which comprises at least 2 suspension constituents (e.g., agents). In aspects, compositions comprise 2 suspension constituents (agents). In aspects, a suspension component comprises an ionic suspension constituent (agent). In aspects, a suspension component comprises a non-ionic suspension constituent (agent). In aspects, a suspension component comprises both an ionic suspension component and a non-ionic suspension component.

In aspects, a suspension component can be any one or more ophthalmologically suitable suspension component constituent, such as, e.g., hyaluronic acid, methylcellulose, carboxymethylcellulose (CMC), hydroxyethylcellulose, hydroxypropyl methylcellulose, gelatin, acacia, povidone, polyvinylpyrrolidone, polysorbates (e.g., polysorbate-80), and polyoxyl-ethylated castor oil (e.g., Cremophor® EL or Cremophor® RH-40), and polyethylene glycols (PEGs), such as, e.g., PEG 400, PEG 3350, etc. or any ophthalmologically suitable derivative, prodrug, hydrate, salt, solvate, enantiomer, or polymorph thereof. In aspects, a suspension component constituent can DOS enhance the suspension of one or more active ingredients (e.g., a quinolone antibiotic component constituent, and anti-inflammatory steroid component constituent, or both). In aspects, a suspension component constituent can DOS increase suspension of a composition when one or more other suspension components are present. For example, higher molecular weight PEGs (such as, e.g., PEG 3350 and the like), or, e.g., acacia, povidone, povidone iodine, or PVP, can provide suspension activity and/or increase the viscosity of the composition, which can, alone or in combination with one or more other suspension component constituents, DOS increase the suspension of one or more active ingredient. In aspects, one or more PEGs can be present with one or more other suspension component constituents. In aspects, a suspension component constituent, e.g., acacia, povidone, povidone-iodine, PVP, or the like, DOS stabilizes a suspension (e.g., maintains a suspension as a suspension for a DOS longer period of time than a similar composition without the constituent). In aspects, a suspension component constituent stabilizes an emulsion, that is, acts as an emulsion stabilizer.

In aspects, a suspension component comprises at least one suspension agent which is not characterizable as a solubilizing compound, such as, e.g., a compound which significantly increases the solubilization of one or more active ingredients, such as, e.g., a fluoroquinolone antibiotic compound a steroid anti-inflammatory compound, a non-steroid anti-inflammatory compound, or a combination thereof. In aspects, compositions lacking such a suspension agent would be capable of solubilizing any active ingredient, such as, e.g., a fluoroquinolone antibiotic compound a steroid anti-inflammatory compound, a non-steroid anti-inflammatory compound, or a combination thereof, to the same extent (e.g., to within ~90%, ~91%, ~92%, ~93%, ~94%, ~95%, ~96%, ~97%, ~98%, ~99%, or, e.g., ~100%) as that accomplished by the same composition comprising the suspension agent.

In aspects, the primary ionic suspension agent in the composition is not a solubilizing agent. In aspects, at least one of the suspension agents is not a solubilizing agent/surfactant. In aspects, most of the suspension component is not composed of solubilizing agent(s)/surfactant(s). In aspects, no part of the suspension component is a surfactant. In aspects, any ionic suspension that is also a surfactant has a molecular weight of less than about 10,000 Da/10 kDA, e.g., less than about 8,000 Da, less than about 7,500 Da, less than about 6,000 Da, less than about 5,000 Da, less than about 3,500 Da, less than about 2,500 Da, or less than about 1,500 Da, such as, e.g., about 1,000 Da-about 10,000 Da, e.g., about 1,250 Da-about 7,750 Da.

In aspects, any suspension agent that is also a surfactant has a molecular weight of at least 1,000 Da/1 kDa, such as at least about 1,250 Da/1.25 kDa.

In aspects, a suspension agent is an FDA approved compound for ophthalmic injections, such as, e.g., CMC, a hyaluronic acid ("HA"). As discussed elsewhere, any reference to hyaluronic acid here includes any suitable form of HA from any organism or synthetic source, derivatized forms of HA, and salts of HA (e.g., sodium hyaluronate).

In aspects, compositions do not comprise a suspension agent which is not approved by the FDA for ophthalmic injections.

In aspects, suspension components comprise at least one constituent having a naturally occurring receptor for the compound on ocular epithelial cells.

In aspects, a suspension agent comprises, mostly comprises, generally consists of, essentially consists of, or consists of a hyaluronic acid component, formed from one or more HA compound(s). In aspects, a "hyaluronic acid component" is synonymous with a "hyaluronic acid composition". In aspects, a "hyaluronic acid component" or "hyaluronic acid composition" can comprise one or more hyaluronic acid compounds.

In aspects, a suspension agent comprises, mostly comprises, generally consists of, consists essentially of, or consists of one or more cellulose compounds, e.g., one or more cellulose derivatives, such as cellulose ester/ether derivatives, such as CMC, hydroxyethylcellulose (HEC), methylcellulose (MC), and the like, such as salts thereof (e.g., sodium CMC).

In aspects, a suspension agent comprises, mostly comprises, generally consists of, or is a polysorbate, such as, e.g., polysorbate-80. In aspects, suspension agent(s) or suspension component or both (whether similar in structure to polysorbate-80 or not) (e.g., some, most, generally all or all suspension agents in a composition) has/have suspension capabilities at least as great as 75% of the suspension capabilities of polysorbate-80, Cremophor RH40, or Cremophor EL. In aspects, suspension agent(s) or suspension component or both (whether similar in structure to polysorbate-80 or not) (e.g., some, most, generally all or all suspension agents in a composition) has/have suspension capabilities at least as great as 75% of the suspension capabilities of polysorbate-80. In aspects, suspension agent or suspension component has suspension capabilities that are at least significantly similar to polysorbate-80 or are DOS improved over polysorbate-80. Examples of suitable suspending agents can, in aspects, include hyaluronic acid, carboxymethyl cellulose (e.g., sodium CMC), hydroxyethyl cellulose, hydroxypropyl methylcellulose, polyvinylpyrrolidone (PVP) (e.g., polyvinylpyrrolidone K90), Pluronic F127, and carbomer. In aspects, the suspension component lacks any effective amount or any detectable amount of Pluronic F127, HPMC, or xanthan gum. In aspects, the suspension component lacks any carbomer-type polymers (acrylic acid polymers). In aspects, the suspension component comprises two or more suspension agents/compounds, which are together in the formulation. In aspects, the suspension component lacks any combination of suspension agents comprising two or more of HA, CMC, HEC, HPMC.

In aspects, a suspension component comprises a polyoxyl-ethylated castor oil, such as a Cremophor® (e.g., Cremophor® EL or Cremophor® RH-40). In aspects, the polyoxyl-ethylated castor oil contributes less than half of the suspension properties of the suspension component. In aspects, a suspension component comprises a polyoxyl-ethylated castor oil in combination with one or more additional suspension agents that exhibit DOS improved suspension effects as compared to the polyoxyl-ethylated castor oil.

In aspects, a suspension component does not comprise any one or more of a co-polymer.

In aspects, a suspension component does not comprise any one or more of a nonionic triblock copolymer. In aspects, a suspension component does not comprise a non-ionic triblock copolymer composed of a central hydrophobic chain of polyoxypropylene (poly(propylene oxide)) flanked by two hydrophilic chains of polyoxyethylene (poly(ethylene oxide)). That is, in aspects, a suspension component does not comprise one or more "poloxamer" agents (or any poloxamer agents), e.g., a Pluronic®, such as Pluronic F127 or an equivalent thereof. In aspects, a suspension component herein does not comprise any one or more of a block co-polymer. In aspects, a suspension component herein does not comprise any one or more of specific block copolymers. In aspects, a suspension component herein does not comprise non-ionic block copolymers. In aspects, a suspension component herein does not comprise a non-ionic polyoxyethylene-polyoxypropylene block copolymer having the chemical structure:

HO—(CH2-CH2-O)x-(C3H6-O)y-(CH2-CH2-O)x-H, wherein x is an integer having the value of at least 8 (such as, e.g., ≥8, ≥9, ≥10, ≥11, ≥12 or more) and y is an integer having the value of at least 38 (such as, e.g., ≥38, ≥39, ≥40, ≥41, ≥42, ≥43, ≥44, ≥45 or more).

In aspects, a suspension component does not comprise a polymer of D-glucose units (e.g., linear linked beta-d-glucose backbone) comprising trisaccharide side chains. In aspects, a suspension component does not comprise a polysaccharide having a trisaccharide side chain comprising mannose units. In aspects, a suspension component does not comprise a polysaccharide having a trisaccharide side chain exhibiting two mannose units separated by guluronic acid. In aspects, a suspension component does not comprise xanthan gum. In aspects, compositions do not comprise a hydrocolloid other than a cellulose derivative hydrocolloid, such as, e.g., in aspects, compositions herein do not comprise a suspension component comprising starch, xanthan, guar gum, locust bean gum, gum karaya, gum tragacanth, or gum Arabic.

In certain aspects, compositions comprise a suspension component which does not represent more than about 10% by mass of the composition. In aspects, compositions comprise a suspension component which represents less than about 9%, such as, e.g., ≤~8%, ≤~7%, ≤~6%, ≤~5%, ≤~4%, or, e.g., ≤~3% by mass of a suspension component. E.g., in aspects, a suspension component makes up about 0.75-10%, e.g., ~1-10%, ~1.5-10%, ~1.5-9%, ~2-8%, ~2.5-7.5%, ~2.5-5%, ~2-6%, ~2-5%, ~2.5-4%, ~2-4.5%, 2-3.5%, or 2.5-3.5% of the composition. In aspects, the suspension component is an ionic suspension component described herein. In aspects, a suspension component is mostly, generally only, or only composed of ionic suspension agent(s). In aspects, the suspension component comprises an ionic and a non-ionic suspension component. In aspects, the ionic suspension component contributes DOS more to the suspension properties of the suspension component than the non-ionic suspending agent/suspension agent. In aspects, the suspension component comprises a mixture of non-ionic suspension components. In aspects, one or more suspension agents of a suspension component can be characterized as a surfactant or a solubilizer/dispersing agent, such as, e.g., polysorbate 80, Solutol HS 15, Pluronic F68, Pluronic F127, Cremophor RH40, Cremophor EL, sodium glycocholate, etc. In aspects, the surfactant component does not comprise an effective amount of a Poloxamer/Pluronic or similar agent (as described elsewhere) or lacks any such component.

Ionic Suspension Component

In aspects, compositions comprise a suspension component comprising one or more ionic suspension agents (constituents), such as, e.g., hyaluronic acid, carboxymethylcellulose, acacia gum, or any combination/mixture thereof.

In aspects, an ionic suspension component comprises a suspension agent having a molecular weight greater than about 2500 kDa, such as, e.g., at least 2600 kDa, ≥~2800 kDa, ≥~3000 kDa, ≥~3200 kDa, ≥~3400 kDa, ≥~3600 kDa, ≥~3800 kDa, ≥~4000 kDa, ≥~4200 kDa, ≥~4400 kDa, ≥~4600 kDa, ≥~4800 kDa, ≥~5000 kDa, or higher. In aspects, an ionic suspension component comprises a suspension agent having an average molecular weight of less than about 3000 kDa. In aspects, an ionic suspension component comprises a suspension agent having an average molecular weight of at least 5000 kDa.

In aspects, the composition lacks any stability agent that exhibits thermosensitivity similar to or more than that of Pluronic F127. In aspects, compositions of the invention are DOS more stable at 20-25 degrees C. than compositions mostly or entirely comprising Pluronic F127 as a suspension agent.

In aspects, compositions comprise an effective amount of hyaluronic acid, carboxymethylcellulose, acacia gum, or any combination/mixture thereof. In general, any compounds described herein by reference include, at least in aspects, any suitable derivatives, prodrugs, hydrates, salts, solvates, enantiomers, or polymorphs thereof, such as, e.g., "hyaluronic acid" or 'hyaluronic acid compound" can comprise "hyaluronate sodium" ("sodium hyaluronate"). In some aspects, compositions comprise only ionic suspension component constituents. In some aspects, compositions comprise a suspension component comprising both ionic and non-ionic suspension component constituents. In aspects, the HA component DOS improves tear film stability, increases conjunctival goblet cell density, protects against corneal epithelial cell damage, or exhibits a combination of some or all thereof. In aspects, a composition comprising HA also comprises an effective amount of trehalose. In aspects, compositions are free of trehalose. In aspects, the HA agent(s) of the composition exhibit DOS mucoadhesive effects (adherence of mucous membranes). In aspects, some, most, or all of the HA agent(s) are crosslinked. In aspects, some, most, or all of the HA agent(s) are not crosslinked. In aspects the HA exhibits DOS hygroscopic/humectant effects. In aspects, the HA can bind at least 10×, at least 20×, at least 50×, at least 100×, at least 200×, at least 500×, or even at least 1000× its weight in water. In aspects HA agent(s) exhibit significant viscoelasticity. In aspects, inclusion of HA agent(s) or similar agent(s) render compositions that can be classified as hydrogels. In aspects, such compositions have increased API residence time, DOS better/more diffusion through layers of the eye, or both.

In aspects, compositions comprise between about 1-40 mg/mL of an ionic suspension component, such as, e.g., between ~1-~38 mg/mL, ~1-~36 mg/mL, ~1-~34 mg/mL, ~1-~32 mg/mL, ~1-~30 mg/mL, ~1-~28 mg/mL, ~1-~26 mg/mL, ~1-~24 mg/mL, ~1-~22 mg/mL, ~1-~24 mg/mL, ~1-~22 mg/mL, ~1-~20 mg/mL, as in, for example, between ~1.1-~40 mg/mL, ~1.2-~40 mg/mL, ~1.3-40 mg/mL, ~1.4-40 mg/mL, ~1.5-~40 mg/mL, ~1.6-~40 mg/mL, ~1.7-~40 mg/mL, ~1.8-~40 mg/mL, or, e.g., ~1.9-~40 mg/mL, as in, for example, between ~1.1-~38 mg/mL, ~1.2-~36 mg/mL, ~1.3-~34 mg/mL, ~1.4-~32 mg/mL, ~1.5-~30 mg/mL, ~1.6-~28 mg/mL, ~1.7-~26 mg/mL, ~1.8-~24 mg/mL, ~1.9-~22 mg/mL, or, e.g., about 2.0-20 mg/mL of a suspension component. In aspects, the ionic suspension component is hyaluronic acid.

In aspects, a suspension component comprises hyaluronic acid. In aspects, a suspension component comprises at least mostly hyaluronic acid. In aspects, compositions provided by the invention comprise a quinolone antibiotic component and an anti-inflammatory steroid component maintained in suspension, the suspension agent being hyaluronic acid having an average molecular weight of between about 200-1800 kDa, such as e.g., between ~200-~1750 kDa, ~200-~1700 kDa, ~200-~1650 kDa, ~200-~1600 kDa, ~200-~1550 kDa, ~200-~1500 kDa, ~200-~1450 kDa, ~200-~1400 kDa, ~200-~1350 kDa, ~200-~1300 kDa, ~200-~1250 kDa, ~200-~1200 kDa, as in, for example, between ~250-~1800 kDa, ~300-~1800 kDa, ~350-~1800 kDa, ~400-~1800 kDa, ~450-~1800 kDa, ~500-~1800 kDa, ~550-~1800 kDa, ~600-~1800 kDa, ~650-~1800 kDa, ~700-~1800 kDa, ~750-~1800 kDa, ~800-~1800 kDa, ~850-~1800 kDa, ~900-~1800 kDa, ~950-~1800 kDa, ~1000-~1800 kDa, ~1050-~1800 kDa, ~1100-~1800 kDa, ~1150-~1800 kDa, ~1200-~1800 kDa, ~1250-~1800 kDa, as in, for example, between ~220-~1750 kDa, ~240-~1700 kDa, ~260-~1650 kDa, ~280-~1600 kDa, ~300-~1550 kDa, ~320-~1500 kDa, ~340-~1450 kDa, ~340-~1400 kDa, ~340-~1350 kDa, ~340-~1300 kDa, ~340-~1250 kDa, or, e.g., between about 360-1200 kDa. In aspects, the average molecular weight of at least some, most, generally all, or all of the hyaluronic acid in the suspension component is between about 360-about 1200 kDa.

In aspects, an ionic suspension component can demonstrate one or more additional functional activities, such as, e.g., an ionic suspension component can provide DOS lubricating activity (e.g., can DOS retain water), DOS increase in the speed of wound healing (e.g., corneal epithelial wound healing), DOS stimulation of epithelial migration, DOS increase the conical contact time of composition(s), DOS increase the viscosity of composition, or any combination thereof.

Non-Ionic Suspension Component

In aspects, compositions comprise a non-ionic suspension component comprising one or more non-ionic suspension agents (constituents). In aspects, compositions comprise only non-ionic suspension component constituents. In aspects, compositions comprise non-ionic and ionic suspension component constituents.

In aspects, a suspension component comprises, mostly comprises, generally consists of, or consists of an ophthalmologically suitable polysorbate, such as, e.g., polysorbate-80. In aspects, a composition comprises a polysorbate suspension component, but the polysorbate suspension component provides less than half of the suspension effects of the suspension component.

In aspects, a suspension component comprises a polyoxyl-ethylated castor oil such as a Cremophor (e.g., Cremophor® EL or Cremophor® RH-40), or, e.g., non-hydroxypropylmethylcellulose cellulose derivatives such as, e.g., methyl cellulose (MC), methyl hydroxyethyl cellulose (MHEC) carboxymethylcellulose (CMC), hydroxyethyl cellulose (HEC), and hydrophobically modified HEC (HMHEC), ethyl hydroxyethyl cellulose (HEC), and hydrophobically modified cellulose ethers (HM-HEC).

While Cremophor® compositions ("compositions" as, e.g., they are often provided as mixtures of compounds) is described in this section as a suspension component or suspension component constituent, in some aspects, a Cremophor® can provide DOS more activity or functionality as an, e.g., emulsifier, solubilizer, or surfactant than a suspending agent.

~85%, ~90%, or at least 95% or more of such compound(s) in suspension. As noted elsewhere, compositions of the invention can be in any suitable form. Suspensions are one such form. Compositions alternatively may be characterized as solutions, colloids, or emulsions depending on ingredients or context. In aspects, compositions are solutions or suspensions. In aspects, compositions of the invention are suspensions.

In some aspects, formulations described herein comprise polyoxyl n castor oils (n=35-40) and polyoxyl hydrogenated castor oils, such as for example polyoxyl 35 castor oil (e.g., Cremophor® EL), polyoxyl 40 castor oil (e.g., Marlowet 40, Emulgin RO 40), a polyoxyethylene hydrogenated castor oil (such as, e.g., polyoxyethylene hydrogenated castor oil 10/polyoxyl 10 hydrogenated castor oil, polyoxyethylene hydrogenated castor oil 40/polyoxyl 40 hydrogenated castor oil (Cremophor® RH 40), polyoxyethylene hydrogenated castor oil 50/polyoxyl 50 hydrogenated castor oil, and polyoxyethylene hydrogenated castor oil 60/polyoxyl 60 hydrogenated castor oil (Cremophor® RH 60)). In aspects, one suitable polyoxyl castor oil is polyoxyl-35-castor oil.

In certain aspects, the suspension component comprises a constituent composed of polyoxyl castor oil compound(s) comprising a number of polyoxyl groups. In one aspect, the polyoxyl castor oil compound(s) is a polyoxyl 40 hydrogenated castor oil composition. For example, in one aspect, the polyoxyl castor oil composition is Cremophor® RH40, a suitable polyoxyl castor oil composition comprising polyoxyl castor oil compound(s) according to the following chemical structure:

General Structure of Cremophor® RH40 (Formula 2)

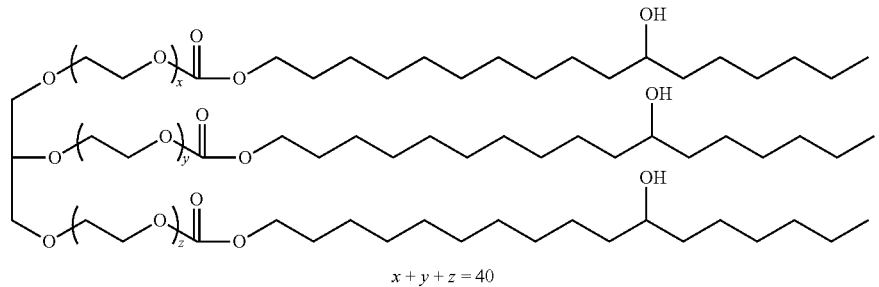

$x + y + z = 40$

In aspects, suspension components comprise a cellulose derivative which does not produce a gel in aqueous solution. In aspects, the cellulose derivative is CMC. In aspects, the non-ionic suspension component does not comprise hydroxypropyl methylcellulose (HPMC).

In aspects, compositions comprising Cremophor® compositions are characterizable as suspensions, as, e.g., the presence of a Cremophor® composition such as, e.g., Cremophor® EL or Cremophor RH-40 does not provide for all ingredients to solubilize so as to form a solution. In aspects, the presence of a polysorbate, such as, e.g., polysorbate-80, or a Cremophor® composition, such as, e.g., Cremophor® EL or Cremophor® RH-40, DOS increases the amount that one or more actives, such as, e.g., one or more fluoroquinolone antibiotic compounds, one or more steroid anti-inflammatory compounds, one or more non-steroid anti-inflammatory compounds, or any combination thereof, is solubilized, however the compositions maintain at least, e.g., ~50%, ~55%, ~60%, ~65%, ~70%, ~75%, ~80%, In certain aspects, suitable compounds of the suspension component used in compositions herein can comprise compound(s) according to Formula 2, wherein x+y+z=a number other than 40, such as e.g., a number other than 40 between 20-60, 30-60, 35-60, 38-60, 38-50, 38-46, 38-44, or 38-42. Also or alternatively, suitable compounds/compositions for use in suspension components herein can comprise compounds wherein x+y+z=~39, ~38, ~37, ~36, ~35, ~34, ~33, ~32, ~31, or ~30 or even lower, or, for example, ~41, ~42, ~43, ~44, ~45, ~46, ~47, ~48, ~49, or ~50 or even higher, e.g. ~52, ~55, or ~58.

In other aspects, polyoxyl castor oil compositions can comprise polyoxyl castor oil compound(s) having any suitable number of polyoxyl groups, regardless of whether such polyoxyl castor oil compound(s) vary from the structure of Formula 2 or not. In aspects, polyoxyl castor oil compound(s) can comprise between ~25-70, ~25-65, ~25-60, ~25-55, ~25-50, ~25-45, or ~25-40, such as for example between ~30-70, ~35-70, ~40-70, ~45-70, ~50-70, ~55-70, ~60-70, or ~65-70 polyoxyl groups, as in between about 30-60, about 30-50, about 30-40, about 40-60, or between about 40-50 polyoxyl groups. In certain aspects, polyoxyl castor oil compound(s) can comprise at least 36 or more polyoxyl groups.

Accordingly, in aspects, one, some, most, generally all, essentially all, or all of the polyoxyl castor oil composition in ophthalmologically suitable compositions comprise a degree of polymerization at least generally equivalent to that of Cremophor® EL (i.e., having a number of polyoxyl groups within about 20% of that of Cremophor® EL, within about 20% of that of Cremophor® RH-40, or both, such as between about 30-45, 32-42, or, e.g., between about 35-40 polyoxyl groups.)

In some respects, the polyoxyl castor oil composition comprises polyoxyl castor oil compounds which are non-hydrogenated. In certain common aspects, the polyoxyl castor oil composition comprises hydrogenated castor oil compounds. In some respects, the polyoxyl castor oil composition mostly comprises, generally only comprises, essentially comprises, or comprises only hydrogenated castor oil compounds (with respect to suspension component polyoxyl castor oil compound(s) in the composition).

In aspects, the ophthalmologically suitable compositions described herein comprise a polyoxyl castor oil composition wherein at least 75% of the polyoxyl castor oil compound(s) in the polyoxyl castor oil composition are hydrogenated. In aspects, at least all detectable or all such compounds are of the polyoxyl castor oil composition are hydrogenated.

In aspects, a polyoxyl castor oil composition of the invention is a pegylated/PEGylated castor oil or a hydrogenated castor oil. In aspects, such an oil can comprise a single compound or molecule or also or alternatively such an oil can be a mixture of molecules.

In aspects, the ophthalmologically suitable compositions herein comprise polyoxyl castor oil composition(s) comprising one or more polyoxyl hydrogenated castor oil compound(s) which make up 65-85% of the polyoxyl hydrogenated castor oil composition.

In aspects, a polyoxyl hydrogenated castor oil composition, such as a pegylated castor oil or hydrogenated castor oil, comprises or is a mixture of hydrophobic and hydrophilic molecules. E.g., in some respects, a polyoxyl castor oil composition of the compositions described herein can be a mixture of hydrophobic and hydrophilic molecules. In aspects for example, about 70-90%, e.g., between ~72-88%, ~74-86%, ~76-~84% of such a polyoxyl castor oil composition is relatively hydrophobic. In aspects, about 75% of a polyoxyl castor oil composition is comprised of relatively hydrophobic molecules. In aspects, at least ~10%, such as at least about 15% or at least about 20%, such as, e.g., between about 10-30% of a polyoxyl castor oil composition is relatively hydrophilic, such as, e.g., between ~12-28, ~14-26, ~16-24, or, e.g., ~16-22, ~16-20, or ~16-18% of the polyoxyl castor oil composition mixture is comprised of relatively hydrophilic components, e.g., is composed of one or more hydrophilic compounds. In aspects, about 25% of the polyoxyl castor oil composition mixture is comprised of relatively hydrophilic components.

In aspects, components of a polyoxyl castor oil composition's relatively hydrophobic portion can comprise or even be mostly comprised of any one or more hydrophobic molecules known in the art to be suitably present in types of such compositions suitable for pharmaceutical uses, including but not limited to glycerol polyethylene glycol ricinoleate, polyethylene glycol 12-oxystearate, glycerol polyethylene glycol hydroxy-stearate, or mixtures thereof. In aspects, such molecules are present together with fatty acid glycerol polyglycol esters to form a hydrophobic part of the polyoxyl castor oil composition.

In aspects, components of a polyoxyl castor oil composition's relatively hydrophilic portion can comprise or even be mostly comprised of any one or more hydrophilic molecules known in the art to be present in such compositions, including but not limited to polyethylene glycols, glycerol ethoxylates, and mixtures thereof. In certain embodiments, compositions herein comprise polyoxyl castor oil compositions wherein some, most, essentially all, or all, such as, e.g., at least about 10%, at least ~20%, at least ~30%, at least ~40%, at least ~50%, at least ~60%, at least ~70% or even more, e.g., at least ~15-35% of the polyoxyl castor oil composition is composed of one or more hydrophilic compounds, such as, e.g., is at least mostly composed of polyethylene glycol, glycerol ethoxylates, or a mixture thereof.

In aspects, a class of castor oils particularly suitable for the compositions herein are referred to as "Cremophors" (because many such products are commercially available previously under the trademarks CREMOPHOR® or currently KOLLIPHOR® (and sold by BASF Corp.). In aspects, such compositions are synthesized by reacting either castor oil or hydrogenated castor oil with varying amounts of ethylene oxide.

In some respects, ophthalmologically suitable compositions described herein can comprise one or more fluoroquinolone antibiotic compounds, one or more steroid anti-inflammatory compounds, one or more non-steroid anti-inflammatory compounds, or a combination thereof, and a polyoxyl castor oil composition comprising hydrogenated compounds, such as, e.g., the polyoxyl castor oil composition can be or can comprise a polyoxyl hydrogenated castor oil. Polyoxyl hydrogenated castor oils suitable for the invention herein can comprise but may not be limited to, e.g., polyoxyl 35 castor oil (e.g., Cremophor® EL), polyoxyl 40 castor oil (e.g., Marlowet 40, Emulgin RO 40), a polyoxyethylene hydrogenated castor oil (such as, e.g., polyoxyethylene hydrogenated castor oil 10/polyoxyl 10 hydrogenated castor oil, polyoxyethylene hydrogenated castor oil 40/polyoxyl 40 hydrogenated castor oil (Cremophor® RH 40/Kolliphor RH40), polyoxyethylene hydrogenated castor oil 50/polyoxyl 50 hydrogenated castor oil, and polyoxyethylene hydrogenated castor oil 60/polyoxyl 60 hydrogenated castor oil (Cremophor® RH 60)). Other suitable polyoxyl castor oil compositions can comprise but may not be limited to Solutol HS 15 or other similar compositions having similar or equivalent properties (e.g., having properties such as HLB, critical micelle concentration, etc.) In aspects, such compositions can further comprise one or more pharmaceutically acceptable excipients. In aspects, such compositions remain stable when stored at room temperature conditions and/or accelerated conditions.

In some aspects, the polyoxyl castor oil composition compounds of the ophthalmologically suitable compositions of the invention can have a critical micelle concentration that lies between about 0.005 and about 0.04% (at about 37 degrees Celsius), such as, e.g., between ~0.008-0.04% or between ~0.009-0.04, such as between ~0.01-0.04%, such as between ~0.012 and ~0.038%, between ~0.014 and ~0.036%, between ~0.016 and ~0.034%, between ~0.018 and ~0.032%, or, e.g., can have a critical micelle concentration of between about 0.02 and about 0.03%. In some respects, the polyoxyl castor oil composition compound(s) has a critical micelle concentration of about 0.03% at 37 degrees Celsius. In certain aspects, the polyoxyl castor oil composition has a critical micelle concentration higher than 0.02%. In certain aspects, the polyoxyl castor oil composition has a critical micelle concentration higher than that of Cremophor® EL.

In aspects, the polyoxyl castor oil composition component in the composition produces emulsions with particle sizes that are detectably or significantly larger than those produced by emulsions emulsified by Cremophor® EL. In aspects, the polyoxyl castor oil composition component in the composition produces emulsions with particle sizes in a detectably or significantly larger range of particles than the range of particle sizes in an emulsion emulsified by Cremophor® EL.

In aspects, the average droplet size formed by a polyoxyl castor oil composition when in an emulsion formulation is between about 60 and about 80 nanometers (nm), such as, e.g., between ~62-80, ~64-80, ~66-80, ~68-80, or between ~70-80 nm, such as for example between ~60-78, ~60-76, ~60-74, ~60-72, ~60-70, or between about ~60-68 nm. In certain aspects, the average droplet size formed by a polyoxyl castor oil composition is between ~65 and ~68 nm. In certain aspects, the average droplet size formed by a polyoxyl castor oil composition is less than 70 nm, such as less than about 69 nm, or less than ~68 nm.

In certain aspects, suitable polyoxyl castor oil compositions of the invention or suitable polyoxyl castor oil compound(s) in polyoxyl castor oil compositions are characterizable by their packing parameter. Packing parameter is a characteristic defined by the formula "v/al", wherein "v" is the hydrophobic volume, "a" is the hydrophilic area, and "l" is the hydrophobic chain length. In aspects, some, most, generally all, or all polyoxyl castor oil compositions used in compositions of the invention have a packing parameter of within about 20% of that of Cremophor® EL, within about 20% of that of Cremophor® RH-40, or both.

In aspects, the polyoxyl castor oil composition or some, most, generally all, or all polyoxyl castor oil compounds of a polyoxyl castor oil composition has a polydispersity index (PDI) of between about 0.1 and about 0.2, such as, e.g., between ~0.1 and ~0.19, between ~0.1 and ~0.18, between ~0.1 and ~0.17, between ~0.1 and ~0.16, or, e.g., between ~0.1 and ~0.15, such as for example between ~0.15 and ~0.2, or between 0.15 and ~0.19. In aspects, a polyoxyl castor oil composition of the ophthalmologically suitable compositions of the invention or the polyoxyl castor oil compounds of the polyoxyl castor oil composition of a composition have a PDI of between about 0.15 and about 0.16. In certain aspects, some, most, generally all, essentially all, or all polyoxyl castor oil compounds of the polyoxyl castor oil composition of an ophthalmologically suitable composition herein have or the polyoxyl castor oil composition of a composition has a PDI of less than 0.17.

In aspects, the polyoxyl castor oil composition in the compositions described herein has a hydrophilic-lipophilic balance (HLB) that lies between ~11 and ~17, such as, e.g., between ~12 and ~17, such as between ~13 and ~17 or between ~14 and ~17, such as, e.g., between ~12 and ~16, between ~12 and ~15, between ~12 and ~14, or between ~13 and ~16, or, e.g., between ~14 to ~16.

In aspects, the average molecular weight of some, most, ≥~75%, ≥~90%, or ≥~95% of the polyoxyl castor oil compound(s) in the polyoxyl castor oil component of the composition is/are greater than about 1700 g/mol-1, such as greater than about 1800 g/mol-1, greater than about 1900 g/mol-1, or greater than about 2000 g/mol-1, such as, e.g., greater than ~2050 g/mol-1, greater than ~2100 g/mol-1, greater than ~2150 g/mol-1, greater than ~2200 g/mol-1, greater than ~2250 g/mol-1, greater than ~2300 g/mol-1, greater than ~2350 g/mol-1, greater than ~2400 g/mol-1, greater than ~2450 g/mol-1, greater than about 2500 g/mol-1, or even higher. In aspects, the average molecular weight of the polyoxyl castor oil compound(s) in the polyoxyl castor oil component of the ophthalmologically suitable compositions is at least about 15%, such as at least ~16%, at least ~17%, at least ~18%, at least ~19%, or at least ~20% greater than the average molecular weight of the polyoxyl castor oil compounds of Cremophor® EL, Cremophor® RH-40, or both.

In certain aspects, the polyoxyl castor oil composition of the compositions herein comprises an amount/degree of ethoxylation within about 20% of that of Cremophor® EL, within about 20% of that of Cremophor® RH-40, or both.

In certain aspects, a polyoxyl castor oil composition of the compositions herein can DOS improve the solubility of one or more components of the compositions. In aspects, the solubility of the active pharmaceutical ingredient in the compositions of the invention, e.g., a fluoroquinolone antibiotic compound, a steroid anti-inflammatory compound, a non-steroid anti-inflammatory compound, or both is at least about 0.5%, ~1%, ~2%, ~3%, ~4%, or at least about 5% or more higher in the composition comprising the polyoxyl castor oil composition than in a composition lacking the polyoxyl castor oil composition.

In certain aspects, a polyoxyl castor oil composition of the compositions herein can DOS improve upon the permeability, bioavailability, or both, of one or more active pharmaceutical ingredients of the composition, e.g., can improve upon the permeability, bioavailability, or both of a fluroquinolone antibiotic compound, a steroid anti-inflammatory compound, a non-steroid anti-inflammatory compound, or combination of any or all thereof. In aspects, the permeability (e.g., of optical tissue) of at least one of a fluroquinolone antibiotic compound, a steroid anti-inflammatory compound, or a non-steroid anti-inflammatory compound in the compositions of the invention is at least about 0.5%, ~1%, ~2%, ~3%, ~4%, or at least about 5% or more higher in the composition comprising the polyoxyl castor oil composition than in a composition lacking the polyoxyl castor oil composition. In aspects, the bioavailability of a fluroquinolone antibiotic compound, a steroid anti-inflammatory compound, a non-steroid anti-inflammatory compound, or combination of any or all thereof in the compositions of the invention is at least about 0.5%, ~1%, ~2%, ~3%, ~4%, or at least about 5% or more higher in the composition comprising the polyoxyl castor oil composition than in a corresponding composition lacking the polyoxyl castor oil composition.

In aspects, ophthalmologically suitable compositions of the invention comprising a polyoxyl castor oil composition are capable of retaining a DOS higher amount (content) of one or more fluroquinolone antibiotic compound(s), a steroid anti-inflammatory compound(s), or non-steroid anti-inflammatory compound(s) in suspension when the composition is stored at about 22° C.-about 25° C. and about 40% relative humidity, or, e.g., at about 40° C. and not more than 25% relative humidity, or both (ophthalmic product), or, e.g., 25° C. and 60% relative humidity or at 40° C. and 75% relative humidity for 3 months (injectable product), for a period of at least about 3 months.

In some respects, the polyoxyl castor oil composition of an inventive composition herein does not impart DOS biological effects in the recipient of the composition. According to aspects, the polyoxyl castor oil composition of a composition is inert. In aspects, the polyoxyl castor oil composition or compound therein present in an ophthalmologically suitable composition herein does not impart an effect having a direct clinical implication; that is, in aspects, the ophthalmologically suitable compositions described herein impart clinical effects related to the one or more fluroquinolone antibiotic compound(s), a steroid anti-inflammatory compound(s), or non-steroid anti-inflammatory compound(s) whereby no additional statistically significant clinical effect is imparted by a polyoxyl castor oil composition of the composition.

In certain aspects, the polyoxyl castor oil compositions in ophthalmologically suitable compositions of the invention are characterizable as non-foaming; e.g., in aspects, suitable polyoxyl castor oil compositions of the composition described herein are characterizable as showing little tendency to form a foam (no detectable foaming or significant amount of foam formation) or are otherwise known in the art not to be likely to form a foam.

In one aspect, a polyoxyl castor oil composition of the compositions herein does not DOS cause severe anaphylactoid hypersensitivity reactions, hyperlipidemia, abnormal lipoprotein patterns, aggregation of erythrocytes, peripheral neuropathy, or any combination thereof.

In one aspect, a polyoxyl castor oil composition does not cause a DOS toxic response/reaction to the composition comprising the polyoxyl castor oil composition.

In a specific aspect, a suitable polyoxyl castor oil composition of the ophthalmic compositions herein is a polyoxyl 35 castor oil formulation, also known as Cremophor® ® EL (BASF, Inc., Ludwigshafen, Germany) or Etocas 35 (Croda, Inc., Parsippany, N.J., USA). In certain alternative aspects, the polyoxyl castor oil composition is not polyoxyl 35 castor oil (e.g., is not Cremophor® EL).

In another specific aspect, a suitable polyoxyl castor oil composition of the composition is an emulsifying agent obtained by reacting hydrogenated castor oil with ethylene oxide. In aspects, such a polyoxyl castor oil composition is a PEG-40 hydrogenated castor oil, e.g., Cremophor® RH40 (also known as Kolliphor® RH40).

In aspects, the polyoxyl castor oil compositions suitable for the compositions herein (e.g., Cremophor® RH40) can be characterizable as soft or flowing pastes at 23 degrees Celsius (° C.). In aspects, suitable polyoxyl castor oil compositions have a very faint or no DOS odor. In aspects, suitable polyoxyl castor oil compositions can form clear solutions in water, are capable of forming clear solutions in ethanol, can form clear solutions in isopropanol, or any combination thereof. In some respects, suitable polyoxyl castor oil compositions can form clear mixtures with fatty acids. In some respects, suitable polyoxyl castor oil compositions can form clear mixtures with fatty alcohols.

In one aspect, suitable polyoxyl castor oil compositions have a sulphated ash content of ≤0.5 g/100 g, such as, e.g., ≤0.4 g/100 g or ≤0.3 g/100 g, such as, e.g., ≤0.29 g/100 g, ≤0.28 g/100 g, ≤0.27 g/100 g, ≤0.26 g/100 g, ≤0.25 g/100 g, ≤0.24 g/100 g, ≤0.23 g/100 g, ≤0.22 g/100 g, ≤0.21 g/100 g, ≤0.20 g/100 g, or even less.

In aspects, suitable polyoxyl castor oil compositions of the compositions herein can have an iodine value of ≤about 2.0/100 g, such as, e.g., ≤about 1.8/100 g, ≤about 1.6/100 g, ≤about 1.4/100 g, ≤about 1.2/100 g, or ≤about 1.0/100 g or even less, such as ≤about 0.8/100 g, ≤0.6/100 g, ≤about 0.4/100 g or even less.

In aspects, suitable polyoxyl castor oil compositions of the compositions herein can have a saponification value of between about 30 and about 80 mg KOH/g, such as, e.g., between ~35-75 mg KOH/g, between ~40-70 mg KOH/g, ~45-65 mg KOH/g, or, e.g., between about 50-60 mg KOH/g.

In aspects, the polyoxyl castor oil compositions detectably or significantly enhance the penetration of fluoroquinolone antibiotic compound(s), steroid anti-inflammatory compound(s), non-steroid anti-inflammatory compounds, or any combination thereof, in eye tissue of subject(s).

In certain aspects, suitable polyoxyl castor oil compositions can have a hydroxyl value of between about 40 and about 95 mg KOH/g, such as, e.g., between ~45-90 mg KOH/g, between ~50-85 mg KOH/g, between ~55-80 mg KOH/g, or, for example, between ~60-75 mg KOH/g.

In certain aspects, suitable polyoxyl castor oil compositions can comprise an amount of 1,4-dioxane which is less than or equal to about 20 mg/Kg, such as ≤about 18 mg/Kg, ≤about 16 mg/Kg, ≤about 14 mg/Kg, ≤about 12 mg/Kg, ≤about 10 mg/Kg, or even less, such as ≤about 8 mg/Kg, ≤about 6 mg/Kg, ≤about 4 mg/Kg, or ≤about 2 mg/Kg.

In certain aspects, suitable polyoxyl castor oil compositions herein can comprise an acid value of less than or equal to about 2.0 mg KOH/g, such as ≤about 1.8 mg KOH/g, ≤about 1.6 mg KOH/g, ≤1.4 mg KOH/g, ≤about 1.2 mg KOH/g, ≤about 1.0 mg/KOH/g, or even less.

In certain aspects, suitable polyoxyl castor oil compositions of the compositions herein can have a pH of between about 5.5-6.6, such as, e.g., between about 5.6-6.4, ~5.7-6.3, ~5.8-6.2, ~5.9-6.1, or between, e.g., ~5-6.

In aspects, suitable polyoxyl castor oil compositions of the compositions described herein can have a water content value (as determined by a Karl Fischer titration method) of, e.g., less than or equal to about 3.0 g/100 g, such as ≤about 2.8 g/100 g, ≤about 2.6 g/100 g, ≤about 2.4 g/100 g, ≤about 2.2 g/100 g, ≤about 2.0 g/100 g, or even less, such as ≤about 1.8 g/100 g or ≤about 1.6 g/100 g or even less.

In aspects, the heavy metal content of suitable polyoxyl castor oil compositions of the invention is less than or equal to about 20 ppm, such as ≤about 18 ppm, ≤about 16 ppm, ≤about 14 ppm, ≤about 12 ppm, or ≤about 10 ppm or less, such as ≤about 8 ppm or ≤about 6 ppm or less.

In aspects, the non-ionic suspension agent is polysorbate, e.g., polysorbate-80. In aspects, the non-ionic suspension agent is a polyoxyl-ethylated castor oil, such as, e.g., Cremophor® EL. In aspects, the non-ionic suspension agent is a polyoxyl-ethylated castor oil, such as, e.g., Cremophor® RH-40.

In aspects, the composition comprises a non-ionic surfactant in an amount of between about 1-20 mg/mL, such as between ~2-~20 mg/mL, ~2-~18 mg/mL, ~2-~16 mg/mL, ~2-~14 mg/mL, ~2-~12 mg/mL, or, e.g., ~2-~10 mg/mL, such as, e.g., between ~4-~20 mg/mL, ~6-~20 mg/mL, ~8-~20 mg/mL, ~10-~20 mg/mL, as in, e.g., between ~2-~18 mg/mL, ~4-~16 mg/mL, ~6-~14 mg/mL, ~8-~12 mg/mL, ~9-~11 mg/mL, or, e.g., about 10 mg/mL. In aspects, the non-ionic surfactant is polysorbate-80, Cremophor® EL, Cremophor® RH-40.

In aspects, a non-ionic suspension component is also a surfactant, e.g., exhibits DOS surfactant (surface-active) activity. In aspects, the non-ionic suspension component is also a non-ionic surfactant. In aspects, the non-ionic suspension and surfactant is, e.g., polysorbate-80, Cremophor® EL, Cremophor® RH-40, or a combination thereof. In specific aspects, the non-ionic suspension and surfactant is polysorbate-80. In aspects a non-ionic suspension and surfactant is a PEG 3350.

Natural/Semi-Synthetic Suspension Component

In aspects, suspension components of the compositions comprise an effective amount of a suspension component which is at least generally all, substantially all, or is/are natural or semi-synthetic suspension agent(s). In aspects, the natural or semi-synthetic suspension agent can be any ophthalmologically suitable natural or semi-natural suspension agent. In aspects, the natural or semi-synthetic suspension agent is not xanthan gum.

In aspects, the suspension component comprises one or more constituent compounds wherein ocular epithelial cells have receptors for the compound. In aspects, for example, the suspension component can comprise hyaluronic acid, and hyaluronic acid can, in aspects, DOS bind to HARE receptors on the surface of ocular epithelial cells. In aspects, the presence of a naturally occurring receptor on the surface of ocular epithelial cells for a constituent compound of a suspension component increases the amount of suspension component endocytosed by such cells, the rate of uptake by such cells of the suspension component, or both, such that the suspension component demonstrates a DOS rate of ocular wound healing when compositions are providing under circumstances where ocular wound(s) are present, such as, e.g., when compositions herein are provided in association with an invasive ophthalmic procedure.

In aspects, suspension component(s) of compositions herein comprise at least one ingredient, such as, e.g., at least 2, at least 3, or at least about 4 ingredients which are naturally occurring compounds found in the eye, such as, e.g., compounds naturally found in, e.g., the vitreous humor aqueous humor). In aspects, suspension component(s) comprise hyaluronic acid. In aspects, compositions comprise 2 or more compounds which are naturally occurring compounds found in the eye. In aspects, compositions comprise, e.g., hyaluronic acid and chondroitin sulfate.

In aspects, one or more suspension components is a natural or semi-synthetic (e.g., semi-natural) suspension agent characterizable as having DOS, such as significant, hygroscopic properties. In aspects, a suspension agent is a natural or semi-synthetic/semi-natural suspension agent having a DOS greater hygroscopicity than that of hydroxypropylmethylcellulose (HPMC), than that of a non-ionic polyoxyethylene-polyoxypropylene block polymer having the chemical structure —HO—(CH2-CH2-O)x-(C3H6-O)y-(CH2-CH2-O)x-H, wherein x is an integer having the value of at least 8 and y is an integer having the value of at least 38, that of xanthan gum, or any combination thereof. In aspect, the suspension agent is a natural or semi-synthetic/semi-natural suspension agent having a hygroscopicity wherein the agent has the ability to absorb a DOS higher amount of water per its mass than that of HPMC, than that of a non-ionic polyoxyethylene-polyoxypropylene block polymer having the chemical structure —HO—(CH2-CH2-O)x-(C3H6-O)y-(CH2-CH2-O)x-H, wherein x is an integer having the value of at least 8 and y is an integer having the value of at least 38, that of xanthan gum, or any combination thereof. In aspects, a suspension agent is a natural or semi-synthetic suspension agent having a DOS faster rate of water absorption than that of hydroxypropylmethylcellulose (HPMC), than that of a non-ionic polyoxyethylene-polyoxypropylene block polymer having the chemical structure —HO—(CH2-CH2-O)x-(C3H6-O)y-(CH2-CH2-O)x-H, wherein x is an integer having the value of at least 8 and y is an integer having the value of at least 38, that of xanthan gum, or any combination thereof.

In aspects, the suspension component can comprise at least one natural or semi-synthetic suspension agent composed of a compound having an average molecular weight of between about 10,000 and about 1,500,000 Daltons (10 kDa-1500 kDa), such as, e.g., between about 100 kDa-about 1400 kDa, ~200 kDa-~1300 kDa, or, e.g., between about 300 kDa-~1200 kDa, such as, e.g., between ~360 kDa-~1200 kDa. In aspects, a natural or semi-synthetic suspension agent is mostly all, generally all, or all hyaluronic acid.

Other Ingredients & APIs

In aspects, compositions of the invention comprise, in addition to the quinolone antibiotic API(s), anti-inflammatory API(s), or both, and other primary ingredients (e.g., suspension agent(s) of a suspension component), one or more additional API(s), additional excipients, or both.

In aspects, an excipient is one or more of a bulking agent, filler, solubilizer, absorption enhancer, chelating agent, antioxidant, tonicity agent, pH-adjusting agent, preservative, thickening agent/viscosity enhancer, carrier, diluent, etc. In aspects, such excipients are suitable for ophthalmological use and present in amounts safe for ophthalmic administration. A pharmaceutically acceptable ingredient can in aspects, be a pharmaceutically acceptable active ingredient which is an ingredient compatible with other ingredient(s) of the composition and not deleterious to the recipient thereof.

In aspects, compositions comprise one or more antifungal (e.g., antimycotic) compounds (constituents/APIs), including, e.g., one or more synthetic antifungal compounds (constituents), classifiable as, e.g., polyenes, azoles, allylamines, and echinocandins, or antiviral compounds (constituents), classifiable as, e.g., attachment or fusion inhibitors, entry inhibitors, uncoating inhibitors, protease inhibitors, polymerase inhibitors, nucleoside and nucleotide reverse transcriptase inhibitors (including nucleoside analogue reverse transcriptase inhibitors (NRTIs)), nonnucleoside reverse-transcriptase inhibitors, and integrase inhibitors, including antiviral compounds which can be described as (which may or may not fit into a previously described group) chemokine coreceptor antagonists. In aspects, in addition to the described quinolone antibiotic API(s) of the composition the composition comprises one or more other antibacterial/antibiotic API(s), such as, e.g., one or more aminoglycosides, carbapenems, cephalosporins, fluoroquinolones, glycopeptides and lipoglycopeptides, macrolides, monobactams, oxazolidones, penicillins, polypeptides, rifamycins, sulfonamides, streptogramins, and tetracyclines. In certain aspects, carbapenems, cephalosporins, monobactams, and penicillins can be grouped together as beta-lactam antibiotics. In aspects, compositions comprise antibiotic compounds which may not fall neatly into one of the above-referenced classes, such as, e.g., chloramphenicol, clindamycin, daptomycin, Fosfomycin, Lefamulin, metronidazole, mupirocin, nitrofurantoin, tigecycline, etc. In aspects, compositions comprise one or more non-quinolone broad-spectrum antibiotics such as, e.g., doxycycline, minocycline, aminoglycosides (except for, e.g., streptomycin), ampicillin, amoxicillin/clavulanic acid, azithromycin, carbapenems, piperacillin/tazobactam, quinolones, tetracycline-class drugs (except, e.g., sarecycline), chloramphenicol, ticarcillin, trimethoprim/sulfamethoxazole, etc. In aspects, compositions comprise API(s) for the treatment of other conditions. In certain aspects, composition(s) do not comprise any API(s) other than any indicated quinolone antibiotic API(s), anti-inflammatory API(s), or both.

Compositions of the invention can, and often will, comprise additional excipients besides the above-described suspension agent and surfactant components of certain compositions.

In aspects, one or more additional excipients is any one or more of a tonicity agent, a preservative, a surfactant, a buffer/buffering agent, a viscoelasticity agent, a vehicle, a chelating agent, an emulsifier, a sequestration agent, a penetration enhancer, a pH adjusting agent, an antioxidant, etc. In general, compositions can include any suitable excipient(s). In aspects, compositions are characterized by inclusion of certain excipients (e.g., a chelating agent, which can be considered a primary ingredient in aspects). A description of select classes of excipients that can be included in compositions of the invention follows.

Chelating Agent(s)

In aspects, compositions provided by the invention comprise one or more ophthalmologically suitable chelating agents. In alternative aspects, compositions provided by the invention do not comprise a chelating agent. In aspects, one or more chelating agents DOS stabilize one or more active ingredients, such as one or more antimicrobial agents (e.g., a fluoroquinolone antibiotic compound), one or more anti-inflammatory compounds (e.g., a steroid or non-steroid anti-inflammatory compound), or both, such as, e.g., by DOS preventing flocculation, DOS preventing premature development of DOS impurities, and the like.

According to aspects, chelating agent(s) are present in composition(s) of the invention which detectably or significantly enhance stability, detectably or significantly enhance preservative effectiveness, or, e.g., detectably or significantly reduce the amount of impurities, such as providing for a composition which is stable under room temperature storage conditions, e.g., retains at least ~90% of the one or more antimicrobial compound constituents and at least ~90% of the one or more anti-inflammatory compound constituents when stored at ordinary/standard storage conditions of about 25° C.+/−2° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product), for at least about one month such as ≥~2 months or such as ≥~3 months, ≥~4 months, ≥~5 months, or, e.g., ≥~6 months.

For example, composition(s) provided by the invention can comprise chelating agent(s) which detectably improve the stability of the one or more quinolone antibiotic component constituents, or one or more anti-inflammatory steroid component constituents, provide a reduced amount of total impurities over that provided by the same composition lacking a chelating agent, enhance preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more (e.g., 3-36 months, 2-24 months, 3-24 months, 4-24 months, 4-36 months, 6-24 months, 6-36 months, 12-36 months, 18-36 months, 18-24 months, 12-60 months, 12-48 months, or ≥12, ≥18, ≥24, ≥30, or ≥36 months).

In aspects, the invention provides composition(s) comprising one or more ophthalmologically suitable chelating agents capable of sequestering divalent or polyvalent metal cations, effective at pH range of between, e.g., ~5.5-~9.5, such as between ~6.0-~9.0, e.g., or, e.g., ~6.5-~8.5. In aspects, a chelating agent of the composition(s) herein do not detectably or significantly negatively impact any other component of the formulation, such as, e.g., they do not detectably or significantly reduce the efficacy of any one or more quinolone antibiotic component constituents, anti-inflammatory steroid component constituents (e.g., reduce microbial growth inhibitory effect or anti-inflammatory effect), or any other API or excipient present or which may be present in the composition.

In aspects any ophthalmologically suitable and pharmaceutically acceptable chelating agent is used. In aspects, exemplary chelating agents present in a composition described herein comprise, e.g., sodium citrate, cromolyn, monomeric polyacids such as an EDTA compound, cyclohexanediamine tetraacetic acid (CDTA), hydroxyethylethylenediaminetriacetic acid (HEDTA), diethylenetriaminepentaacetic acid (DTPA), dimercaptopropane sulfonic acid (DMPS), dimercaptosuccinic acid (DMSA), aminotrimethylene phosphonic acid (ATP A); suitable and effective derivatives or analogs of any thereof, or other related compounds (as exemplified with respect to other variant compounds described above in connection with APIs) (or equivalents thereof); any ophthalmologically acceptable salts thereof, and/or combinations of any two or more such compounds. In other aspects, a chelating agent is a phosphate, such as, e.g., pyrophosphates, tripolyphosphates, and, hexametaphosphates; a chelating antibiotic such as chloroquine and tetracycline; a nitrogen-containing chelating agent containing two or more chelating nitrogen atoms within an imino group or in an aromatic ring (e.g., diimines, 2,2'-bipyridines, etc.); or for example a polyamine such as cyclam (1,4,7,11-tetraazacyclotetradecane), N—($C_1$-$C_{30}$ alkyl)-substituted cyclams (e.g., hexadecyclam, tetramethyl hexadecyl cyclam), diethylenetriamine (DETA), spermine, diethylnorspermine (DENSPM), diethylhomospermine (DEHOP), and deferoxamine (N'-[5-[[4-[[5-(acetylhydroxyamino) pentyl] amino]-1,4-dioxobutyl]hydroxyamino]pentyl]-N'-(5-aminopentyl)-N-hydroxybutanediamide; also known as desferrioxamine B and DFO).

In aspects, composition(s) provided by the invention comprise ≥1 ophthalmologically suitable chelating agents characterizable as a monomeric polyacid. In aspects, a chelating agent comprises an ethylenediaminetetraacetic acid (EDTA) compound or an ophthalmologically suitable EDTA salt such as, e.g., diammonium EDTA, disodium EDTA, dipotassium EDTA, triammonium EDTA, trisodium EDTA, tripotassium EDTA, or disodium edetate/edetate disodium, or also known as edetate calcium disodium. In aspects, compositions comprise a chelating agent that results in a significantly similar (e.g., statistically similar) or measurably improved stability of the active ingredients as compared to disodium edetate. In this sense, compositions also can be described as comprising a "means" for chelation. In such a respect, any known equivalents of such named agents can also be, e.g., are, incorporated into compositions or methods of the invention.

In aspects, one or more chelating agents such as disodium edetate is present in the compositions provided by the invention in an amount representing between about 0.01 mg/mL-about 2 mg/mL, such as e.g., between ~0.01-~1.9 mg/mL, ~0.01-~1.8 mg/mL, ~0.01-~1.7 mg/mL, ~0.01-~1.6 mg/mL, ~0.01-~1.5 mg/mL, ~0.01-~1.4 mg/mL, ~0.01-~1.3 mg/mL, ~0.01-~1.2 mg/mL, ~0.01-~1.1 mg/mL, ~0.01-~1 mg/mL, ~0.01-0.9 mg/mL, ~0.01-~0.8 mg/mL, ~0.1-~0.7 mg/mL, ~0.01-~0.6 mg/mL, ~0.01-~0.5 mg/mL, as in, for example, between ~0.02-~2 mg/mL, ~0.03-~2 mg/mL, ~0.04-~2 mg/mL, ~0.05-~2 mg/mL, ~0.06-~2 mg/mL, ~0.07-~2 mg/mL, ~0.08-~2 mg/mL, ~0.09-~2 mg/mL, ~0.1-~2 mg/mL, as in, for example, between ~0.02-~1.9 mg/mL, ~0.03-~1.8 mg/mL, ~0.04-~1.7 mg/mL, ~0.05-1.6 g/mL, ~0.06-~1.5 mg/mL, ~0.07-~1.4 mg/mL, ~0.08-~1.3 mg/mL, ~0.09-~1.2 mg/mL, ~0.1-~1.1 mg/mL, ~0.1-~1 mg/mL, ~0.1-~0.9 mg/mL, ~0.1-~0.8 mg/mL, ~0.1-~0.7 mg/mL, ~0.1-~0.6 mg/mL, or, e.g., about 0.1-about 0.5 mg/mL. In aspects, the chelating agent is disodium edetate.

In aspects, composition(s) provided by the invention comprise ≥1 pharmaceutically acceptable chelating agents which result in a significantly similar or improved stability of the active ingredients as compared to disodium edetate in a concentration of about 0.1-about 0.5 mg/mL. In aspects, composition(s) provided by the invention comprise ≥1 pharmaceutically acceptable chelating agents which result in a significantly similar or improved stability of the active ingredients as compared to disodium edetate in a concentration of between about 0.01 mg/mL-about 2 mg/mL, such as e.g., between ~0.01-~1.9 mg/mL, ~0.01-~1.8 mg/mL, ~0.01-~1.7 mg/mL, ~0.01-~1.6 mg/mL, ~0.01-~1.5 mg/mL, ~0.01-~1.4 mg/mL, ~0.01-~1.3 mg/mL, ~0.01-~1.2 mg/mL, ~0.01-~1.1 mg/mL, ~0.01-~1 mg/mL, ~0.01-0.9 mg/mL, ~0.01-~0.8 mg/mL, ~0.1-~0.7 mg/mL, ~0.01-~0.6 mg/mL, ~0.01-~0.5 mg/mL, as in, for example, between ~0.02-~2 mg/mL, ~0.03-~2 mg/mL, ~0.04-~2 mg/mL, ~0.05-~2 mg/mL, ~0.06-~2 mg/mL, ~0.07-~2 mg/mL, ~0.08-~2 mg/mL, ~0.09-~2 mg/mL, ~0.1-~2 mg/mL, as in, for example, between ~0.02-~1.9 mg/mL, ~0.03-~1.8 mg/mL, ~0.04-~1.7 mg/mL, ~0.05-~1.6 g/mL, ~0.06-~1.5 mg/mL, ~0.07-~1.4 mg/mL, ~0.08-~1.3 mg/mL, ~0.09-~1.2 mg/mL, ~0.1-~1.1 mg/mL, ~0.1-~1 mg/mL, ~0.1-~0.9 mg/mL, ~0.1-~0.8 mg/mL, ~0.1-~0.7 mg/mL, ~0.1-~0.6 mg/mL, or, e.g., about 0.1-about 0.5 mg/mL.

In aspects, compositions comprise between about 0.1-15 mg/mL of a chelating agent such as sodium citrate, e.g., in an amount between ~0.1-~14.5 mg/mL, ~0.1-~14 mg/mL, ~0.1-~13.5 mg/mL, ~0.1-~13 mg/mL, ~0.1-~12.5 mg/mL, ~0.1-~12 mg/mL, ~0.1-~11.5 mg/mL, ~0.1-~11 mg/mL, ~0.1-~10.5 mg/mL, or, e.g. ~0.1-~10 mg/mL, such as, e.g. ~0.2-~15 mg/mL, ~0.3-~15 mg/mL, ~0.4-~15 mg/mL, ~0.5-~15 mg/mL, ~0.6-~15 mg/mL, ~0.7-~15 mg/mL, ~0.8-~15 mg/mL, ~0.9-~15 mg/mL, ~1-~15 mg/mL, such as, e.g., between ~0.2-~14 mg/mL, ~0.4-~13 mg/mL, ~0.6-~12 mg/mL, ~0.8-~11 mg/mL, or, e.g., between about 1-about 10 mg/mL of a chelating agent such as, e.g., sodium citrate.

Preservative(s)

In aspects, compositions provided by the invention comprise one or more ophthalmologically suitable preservation agent(s) ("preservatives"). In alternative aspects, compositions provided by the invention do not comprise a preservative, such that the composition(s) provided by the invention are characterizable as "preservative free." In aspects, compositions lack any significant amount of any agent that is solely/mostly characterizable as a preservative or that is at all characterized as a preservative.

Uncontradicted, any aspect described herein as being "free" of a component/element simultaneously implicitly provides such "low" amount compositions of the ingredient/component in question (a low amount meaning less than 5%, less than 2%, less than 1%, less than 0.5%, less than 0.2%, less than 0.1%, less than 0.05%, less than 0.02%, or less than 0.01% of the composition on a weight basis, volume basis, or compound number basis). Alternatively a low amount can mean an amount that is less than 50%, such as less than 20%, less than 10%, less than 5%, or less than 1% of the typical amount of the element/composition in corresponding compositions, methods, etc.

In aspects, one or more compounds of a composition providing a DOS preservative effect can also provide one or more additional DOS effects, such as chelation effect, buffering effect, penetration enhancement effect, etc.

In aspects, a "preservative" is a compound which detectably or significantly enhance stability of the composition(s), such as the stability of the one or more quinolone antibiotic component constituents, one or more anti-inflammatory compound constituents, or both, reduces the number(s)/amount(s) of detectable/significant impurities over the course of a storage under room temperature or accelerated storage conditions, detectably or significantly reduce antimicrobial activity (e.g., within the composition), or any combination of any or all thereof. In aspects, one or more preservative(s) are present in composition(s) of the invention which detectably or significantly enhance stability of the composition(s), such as the stability of the one or more antimicrobial compounds, one or more anti-inflammatory compounds, reduces the amount of impurities, or any combination of any or all thereof, such as providing for a composition which is stable under room temperature storage conditions, e.g., providing for compositions which retain at least 90% of the one or more quinolone antibiotic component constituents and at least 90% of the one or more anti-inflammatory steroid component constituents when stored at about 25° C.+/−2° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product), for at least about one month such as ≥~2 months or such as ≥~3 months or more. In aspects, compositions provided by the invention comprises one or more preservatives in anti-microbially effective amount(s) which can detectably or significantly inhibit microbial growth.

In aspects, an "antimicrobial effective amount" of a preservative is determined by performing preservative efficacy tests or antimicrobial effectiveness tests known in the art. In aspects, such tests are described in, e.g., chapter 51 of the United States Pharmacopoeia 29-National Formulary 24 (USP 29-NF 24). In aspects, composition(s) provided by the invention comprise one or more preservatives in an amount within the concentration ranges described in one or more standard reference books such as the most recent edition of Remington's Pharmaceutical Sciences, Handbook of Pharmaceutical Excipients $5^{th}$ ed. or $6^{th}$ ed., or Handbook of Pharmaceutical Excipients ($9^{th}$ ed.), Sheskey et al. (ISBN 9780 85711 375 7) (2020).

For example, composition(s) provided by the invention comprise one or more preservatives which detectably or significantly improve the stability of the one or more quinolone antibiotic component constituents or one or more anti-inflammatory compound constituents, enhances quinolone antibiotic component or anti-inflammatory effectiveness, prevent detectable or significant anti-microbial growth within the composition(s), or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more (e.g., about 3-36 months, about 6-36 months, about 4-36 months, about 18-36 months, about 12-24 months, about 6-24 months, or about 12-36 months).

In aspects, the invention provides composition(s) comprising ophthalmologically suitable preservative(s) effective (e.g., agents capable of demonstrating one or more of the characteristics of a preservative described above in the context of a composition of the invention) at pH range of between, e.g., ~5.5-~9.5, such as between ~6.0-~9.0, e.g., or, e.g., ~6.5-~8.5. In aspects, a preservative of the composition(s) herein does not detectably or significantly negatively impact any other component of the formulation, such as, e.g., they do not detectably or significantly reduce the efficacy or functionality of any one or more quinolone antibiotic component constituents, anti-inflammatory compound constituents (e.g., reduce infection-reducing/treating effect or reduce anti-inflammatory effect), or any other API or excipient present or which may be present in the composition.

In aspects any ophthalmologically suitable and pharmaceutically acceptable preservative is used. In aspects, exemplary preservative(s) present in a composition described herein comprise effective amount(s) of, e.g., benzoic acid; hydrogen peroxide; sorbic acid; biguanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal (e.g., stabilized thimerosal, and other such as, e.g., benzoic acid, benzyl alcohol, benzyl paraben, bronopol, butyl paraben, cetrimide, cetyl-pryidinium chloride, chlorohexidine, chlorocresol, chloroxylenol, cresol, ethyl alcohol, ethyl paraben, ethylparaben, glycerin, hexetidine, imidurea, isobutyl paraben, meta-cresol, phenol, phenoxyethanol, phenylethyl alcohol, phenylmucuric nitrate, p-hydroxybenzoic acid esters, polyhexamethylene biguanide, potassium sorbate, propyl paraben, propylene glycol, sodium benzoate, sodium perborate, sodium propionate, sorbic acid, sodium citrate, benzalkonium chloride, benzethonium chloride, benzoic acid, benzyl alcohol, benzyl paraben, bronopol, butyl paraben, cetrimide, cetylpyridinium chloride, chlorobutanol, chlorhexidine, chlorocresol, chloroxylenol, cresol, ethyl alcohol, ethyl paraben, ethylparaben, glycerin, hexetidine, imidurea, isobutyl paraben, meta-cresol, methyl paraben, methylparaben, phenol, phenoxyethanol, phenylethyl alcohol, phenylmercuric nitrate, p-hydroxybenzoic acid esters, polyhexamethylene biguanide, potassium sorbate, propyl paraben, propylene glycol, sodium benzoate, sodium perborate, sodium propionate, sorbic acid, stabilized thimerosal, and/or thimerosal etc., or any ophthalmologically acceptable salts thereof, or combinations of any ≥2 of such compounds, or equivalents thereof.

In aspects, compositions comprise sodium citrate. In aspects, sodium citrate can provide one or more activities in addition to acting as a preservative, such as, e.g., providing buffering activity, emulsification activity, sequestration activity, or any combination thereof.

In aspects, composition(s) provided by the invention comprise one or more quaternary ammonium compounds, such as, e.g., benzalkonium chlorides (abbreviated herein as BKC, and which is often abbreviated in the art as BAC, BAK, or BZK). Benzalkonium chlorides may also be referred to as alkyl dimethyl benzyl ammonium chlorides (ADBAC), alkyl dimethyl (phenylmethyl) chlorides, or ammonium alkyl dimethyl benzyl chlorides. In aspects, BKC can serve as a penetration enhancer, preservative, solubilizer, or any combination thereof. That is, in aspects, BKC can provide a detectable or significant increase in the penetration, e.g., the bioavailability, of one or more ingredients of the composition(s) or both, can provide preservation qualities such as those described in this section or in the art, or, e.g., can detectably or significantly improve upon the solubilization of any one or more APIs, such as any one or more quinolone antibiotic component constituents, one or more anti-inflammatory steroid component constituents, or a combination thereof.

In this and any other excipient aspect of the invention, the invention also can be characterized as comprising a "means" for preserving composition(s) of the invention. In such a respect, any known equivalents of such named agents can also be, e.g., are, incorporated into compositions or methods of the invention. As with other sections similar described herein any of the components of the invention can be, where suitable, described as means (e.g., the above-described suspension agents/components can be described as API suspension means or means for suspending the active pharmaceutical ingredient(s) of the composition.

In aspects, compositions comprise between about 0.1-15 mg/mL of a preservative, such as, e.g., sodium citrate, such as e.g., between ~0.1-~14.5 mg/mL, ~0.1-~14 mg/mL, ~0.1-~13.5 mg/mL, ~0.1-~13 mg/mL, ~0.1-~12.5 mg/mL, ~0.1-~12 mg/mL, ~0.1-~11.5 mg/mL, ~0.1-~11 mg/mL, ~0.1-~10.5 mg/mL, or, e.g. ~0.1-~10 mg/mL, such as, e.g. ~0.2-~15 mg/mL, ~0.3-~15 mg/mL, ~0.4-~15 mg/mL, ~0.5-~15 mg/mL, ~0.6-~15 mg/mL, ~0.7-~15 mg/mL, ~0.8-~15 mg/mL, ~0.9-~15 mg/mL, ~1-~15 mg/mL, such as, e.g., between ~0.2-~14 mg/mL, ~0.4-~13 mg/mL, ~0.6-~12 mg/mL, ~0.8-~11 mg/mL, or, e.g., between about 1-about 10 mg/mL of a preservative, such as, e.g., sodium citrate.

In aspects, one or more preservatives, such as, e.g., benzalkonium chloride, are present in compositions in an amount of between about 0.01-0.1 mg/mL, such as, e.g., between ~0.02-~0.1 mg/mL, ~0.03-~0.1 mg/mL, ~0.04-~0.1 mg/mL, or, e.g. ~0.05-~0.1 mg/mL, such as, e.g., between ~0.01-~0.09 mg/mL, ~0.01-~0.08 mg/mL, ~0.01-~0.07 mg/mL, ~0.01-~0.06 mg/mL, or, e.g. ~0.01-~0.05 mg/mL, as in between about ~0.02-~0.09 mg/mL, ~0.03-~0.08 mg/mL, ~0.04-~0.07 mg/mL, ~0.04-~0.06 mg/mL, or, e.g., about 0.05 mg/mL benzalkonium chloride.

In aspects, the total amount of preservative in the compositions is between about 0.1-about 15 mg/mL, such as, e.g. between ~0.1-~14.5 mg/mL, ~0.1-~14 mg/mL, ~0.1-~13.5 mg/mL, ~0.1-~13 mg/mL, ~0.1-~12.5 mg/mL, ~0.1-~12 mg/mL, ~0.1-~11.5 mg/mL, ~0.1-~11 mg/mL, ~0.1-~10.5 mg/mL, or, e.g. ~0.1-~10 mg/mL, such as, e.g. ~0.2-~15 mg/mL, ~0.3-~15 mg/mL, ~0.4-~15 mg/mL, ~0.5-~15 mg/mL, ~0.6-~15 mg/mL, ~0.7-~15 mg/mL, ~0.8-~15 mg/mL, ~0.9-~15 mg/mL, ~1-~15 mg/mL, such as, e.g., between ~0.2-~14 mg/mL, ~0.4-~13 mg/mL, ~0.6-~12 mg/mL, ~0.8-~11 mg/mL, or, e.g., between about 1-about 10 mg/mL of preservative(s).

Tonicity Agent(s)

In aspects, compositions comprise one or more ophthalmologically suitable tonicity agents. In alternative aspects, compositions provided by the invention do not comprise any component characterizable as a tonicity agent. Herein, "tonicity agent" refers to a substance used in the ophthalmic compositions to effectively adjust the composition of the formulation to be within a desired isotonic range, e.g., be characterizable as being having an osmolality within a defined range, e.g., a range as provided below.

According to aspects, one or more tonicity agents are present in composition(s) of the invention which detectably or significantly reduce irritability or increase tolerability of the ophthalmic composition(s) over the same composition lacking such a tonicity agent or having a significantly different osmolality. In aspects, inclusion of a tonicity agent can provide a tonicity of the composition rendering a composition tolerable (e.g., lacking clinically significant irritation or damage) by a recipient/recipient eye.

In aspects, tonicity agent(s) of the composition(s) herein do not detectably or significantly negatively impact any other component of the formulation, such as, e.g., they do not detectably or significantly reduce the efficacy of any one or more quinolone antibiotic components, any one or more anti-inflammatory steroid components, or any other API or excipient present or which may be present in the composition.

In facets, any ophthalmologically suitable and pharmaceutically acceptable tonicity agent(s) is used in compositions. Examples thereof include ionic isotonic agents, non-ionic isotonic agents, and the like. Examples of the ionic isotonic agents include inorganic salts, organic salts, electrolytes, etc. Examples of the inorganic salts include sodium chloride, disodium phosphate, sodium dihydrogen phosphate, potassium dihydrogen phosphate, sodium hydrogen sulfite, sodium sulfite, sodium thiosulfate, magnesium sulfate, potassium chloride, calcium chloride, magnesium chloride, boric acid, borax, and the like. Examples of the organic salts include potassium acetate, sodium acetate, sodium hydrogen carbonate, sodium carbonate, and the like. Examples of the non-ionic isotonic agents include polyhydric alcohols having two or more alcoholic hydroxy groups in single molecules, and the like. Specific examples of the polyhydric alcohols include, for example, glycerol, propylene glycol, polyethylene glycol, glucose, trehalose, mannitol, dextrose, sucrose, xylitol, sorbitol, etc., or combinations of any two or more of such compounds.

In this and any other excipient aspect of the invention, the invention also can be characterized as comprising a "means" for performing the function(s) associated with a type of excipient (e.g., such agents can be classified as "means for controlling tonicity" or "means for providing tonicity" and the like). In such a respect, any known equivalents of such named agents can also be incorporated into compositions or methods of the invention. This principle applies generally to any excipients and other components of compositions and steps of methods described herein.

In aspects, one or more tonicity agent(s) can be present in the compositions provided by the invention in an amount representing between about 0.001 w/v. %-about 1.4 w/v. % of the composition, such as, e.g., ~0.08 w/v. %-~1.2 w/v. %, ~0.06 w/v. %-~1 w/v. %, ~0.04 w/v. %-~0.9 w/v. %, or, e.g., between ~0.01 w/v. %-~0.8 w/v. % of the composition.

Buffer(s)/Buffering Agent(s)

In aspects, compositions provided by the invention comprise one or more buffering agents. In aspects, buffering agents are used to adjust the pH of a composition to a desirable range, such as, e.g., to a pH of between about 5.5-about 9.5, such as between ~6.0-~9.0, e.g., or, e.g., ~6.5-~8.5.

In aspects, a buffering agent is any ophthalmologically suitable buffering agent including, e.g., acetate, borate, carbonate, citrate, tris, succinate, maleate, histidine, and phosphate buffering agents, or any ophthalmologically suitable derivatives, e.g., salts thereof, or combinations of any two or more such compounds, or equivalents thereof. In aspects, a buffering agent is sodium citrate.

In certain aspects, compositions comprise sodium citrate. In aspects, sodium citrate can provide one or more activities in addition to acting as a buffering agent, such as, e.g., providing preservative activity, emulsification activity, sequestration activity, or any combination thereof.

In this and any other excipient aspect of the invention, the invention also can be characterized as comprising a "means" for buffering composition(s). In such a respect, any known equivalents of such named agents can also be, e.g., are, incorporated into compositions or methods of the invention.

In aspects, one or more buffering agents, such as, e.g., sodium citrate, is present in compositions in an amount of between about 0.5-20 mg/mL, such as, e.g., between ~0.6-~20 mg/mL, ~0.7-~20 mg/mL, ~0.8-~20 mg/mL, ~0.9-~20 mg/mL, or, e.g., ~1-~20 mg/mL, such as, e.g. ~0.5-~19 mg/mL, ~0.5-~18 mg/mL, ~0.5-~17 mg/mL, ~0.5-~16 mg/mL, ~0.5-~15 mg/mL, ~0.5-~14 mg/mL, ~0.5-~13 mg/mL, ~0.5-~12 mg/mL, ~0.5-~11 mg/mL, or ~0.5-~10 mg/mL, such as, e.g., between ~0.6-~18 mg/mL, ~0.7-~16 mg/mL, ~0.8-~14 mg/mL, ~0.9-~12 mg/mL, or, e.g., between about 1-about 10 mg/mL.

pH Adjusting Agent(s)

In aspects, the pH of the composition(s) provided by the invention is adjusted using one or more ophthalmologically suitable pH adjusting agent(s). In aspects, the composition(s) provided by the invention comprise such one or more pH adjusting agent(s). In alternative aspects, compositions provided by the invention do not comprise any component that is a pH adjusting agent.

Herein, a "pH adjusting agent" is an acidifying or alkalizing agent used to significantly lower or raise the pH (potential hydrogen) of the composition to a target value. In aspects, a pH adjusting agent is an agent which, alone, is incapable of providing a buffering capacity of the composition. In aspects, a pH adjusting agent is not accompanied by a corresponding acid or base to provide a buffering capacity to the composition. In aspects, an acidifying pH adjusting agent is present to lower the pH, while an alkalizing agent is present to raise the pH to a target level. In aspects, an acidifying agent is characterizable as a strong acid. In aspects, an alkalizing agent is characterizable as a strong base. In aspects, a pH adjusting agent is added during the manufacturing process of the composition(s) to adjust the pH of the composition prior to final packaging.

According to aspects, one or more pH adjusting agents are present in composition(s) of the invention in an amount and of a nature of which provide the resulting composition with a pH of between about 5.5-9.5, such as, e.g., between ~5-~9.4, ~5-~9.3, ~5-~9.2, ~5-~9.1, ~5-~9, ~5-~8.9, ~5-~8.8, ~5-~8.7, ~5-~8.6, or, e.g. ~5-~8.5, or, e.g. ~5.1-~9.5, or ~5.2-~9.5, ~5.4-~9.5, ~5.5-~9.5, ~5.6-~9.5, ~5.7-~9.5, ~5.8-~9.5, ~5.9-~9.5, ~6-~9.5, ~6.1-~9.5, ~6.2-~9.5, ~6.3-~9.5, ~6.4-~9.5, or, e.g. ~6.5-~9.5, such as, e.g. ~5.7-~9.2, ~6-~8.9, ~6.1-~8.8, ~6.2-~8.7, ~6.3-~8.6, ~6.4-~8.6, or, e.g., ~6.5-~8.5.

In aspects, pH adjusting agent(s) of the composition(s) herein do not detectably or significantly negatively impact any other component of the formulation, such as, e.g., they do not detectably or significantly reduce the efficacy of any one or more quinolone antibiotic components, anti-inflammatory steroid components (e.g., reduce microbial inhibition effect or reduce anti-inflammatory effect), or any other API or excipient present in a composition.

In aspects any ophthalmologically suitable and pharmaceutically acceptable pH adjusting agent is used. In aspects, exemplary pH adjusting agent(s) in a composition comprise any suitable pH adjusting agents commonly used and known in the art, such as, e.g., an acid such as a strong acid or, e.g., a base such as a strong base. In aspects, a pH adjusting agent is, e.g., a mineral acid such as sodium hydroxide hydrochloric acid (HCl) or sodium hydroxide (NaOH), such as, for example, ~1N HCl or ~1N NaOH (1N being the concentration of the agent added to the composition(s) to adjust the pH of the composition(s)).

In this and any other excipient aspect of the invention, the invention also can be characterized as comprising a "means" for adjusting pH of composition(s) of the invention. In such a respect, any known equivalents of such named agents can also be, e.g., are, incorporated into compositions or methods of the invention.

In aspects, one or more pH adjusting agent(s) can be present in the compositions provided by the invention in an amount effective in providing the target pH. In aspects, such an amount can be considered a "trace amount," e.g., less than ~0.005 w/v. %, <0.004 w/v. %, <~0.003 w/v. %, <0.002 w/v. %, e.g., <~0.001 w/v. %. In aspects, such an amount can be an amount representing between about 0-about 0.01 w/v. %. In aspects, one or more pH adjusting agent(s) can be present in the compositions provided by the invent ion in an amount effective in providing the target pH, such amounts representing between about 0-about 0.1%, such as, e.g., about 0.01%, ~0.02%, ~0.03%, ~0.04%, ~0.05%, ~0.06%, ~0.07%, ~0.08%, or, e.g., ~0.09%.

Surfactant(s)

In aspects, compositions comprise one or more ophthalmologically suitable surfactants. Such aspects also are somewhat described above in connection with surfactants that also can be characterized as suspension agents (e.g., polysorbate 80). In alternative aspects, compositions provided by the invention do not comprise any component characterizable as a surfactant.

The term "surfactant" typically refers to a substance used in the ophthalmic compositions to DOS reduce surface tension of the composition(s), DOS increase surface spreading (e.g., wetting) or both. In aspects, a surfactant DOS improves dispersion of suspended particles within compositions herein over the dispersion of suspended particles in compositions lacking a surfactant. As noted, such agents are often characterized as or are closely related to agents described as solubilizers, dispersing agents, or both. Any agent exhibiting one or more of such characteristics can be present where desired/suitable.

According to aspects, one or more surfactants are present in composition(s) of the invention which detectably or significantly increase the spreading/wetting of the ophthalmic composition(s) over the same composition lacking such a surfactant or having a significantly different surface tension-related property.

In aspects, surfactant(s) of the composition(s) herein do not DOS negatively impact any other component of the formulation, such as, e.g., they do not DOS reduce the efficacy of any one or more quinolone antibiotic components, any one or more anti-inflammatory steroid components, or any other API or excipient present or which may be present in the composition.

In facets, any ophthalmologically suitable and pharmaceutically acceptable surfactant(s) are used in compositions. Exemplary surfactants(s) include, e.g., lecithin and lecithin derivatives including pure phospholipids such as, e.g., soya phosphatidyl choline) and mixed phospholipids, sodium cholate, and hydroxylated phospholipids/hydroxylated lecithin; glycerol fatty acid esters including polyglycerol fatty acid esters, polyglycerol polyricinoleate, hydrogenated castor oils and propylene glycol fatty acid esters (such as, e.g., polyoxyethyleneglycerol triricinoleate, Cremophor® EL (macrogol-1500-glyceroltriricinoleate), Cremophor® RH-40, and monobutyl glycerol); polysorbates such as polysorbate-80; sorbitan fatty acid esters including sorbitan monolaurate and sorbitan monoleate; polyoxyethylene sorbitan fatty acid esters including polyethylene glycol sorbitan monolaurate and polyethylene glycol sorbitan monooleate; etc., including propylene glycol, PEGs (e.g., PEG 200, PEG 400, PEG 3350, etc.), and cosurfactants such as alkanols (e.g., ethanol, propanol, butanol, etc.), alkane-diols (e.g., 1,2-propane diol, 1,2-butane diol, etc.), and alkane-polyols (glycerol, glucitol, polyethylene glycol, etc.), or derivatives thereof or combinations of any two or more of such compounds.

In aspects, compositions comprise one or more non-ionic surfactants. In aspects, a non-ionic surfactant can be, e.g., any ophthalmologically suitable non-ionic surfactant. In aspects, the non-ionic surfactant is, e.g., a polysorbate, a polyoxyl-ethylated castor oil (such as, e.g., Cremophor® EL, or e.g., Cremophor® RH-40), or, e.g., is a component comprising a combination thereof.

In aspects, compositions comprise one or more ionic surfactants. In aspects, compositions comprise one or more non-ionic surfactants and one or more ionic surfactants. In aspects, a non-ionic surfactant can provide one or more other DOS functions. In aspects, a non-ionic surfactant can exhibit, suspension-related properties. In aspects, a non-ionic surfactant is also a non-ionic suspension agent. In aspects, the non-ionic surfactant, non-ionic suspension agent is a polysorbate compound. In aspects, the polysorbate compound is polysorbate-80. In aspects, a non-ionic surfactant, non-ionic suspension agent is a polyoxyl-ethylated castor oil. In aspects, a polyoxyl-ethylated castor oil is a Cremophor® EL or Cremophor® RH-40.

In aspects, compositions comprise 2 or more surfactants, such as, e.g., 2 or more ionic surfactants, 2 or more non-ionic surfactants, or, e.g., at least one ionic surfactant and at least one non-ionic surfactant. In aspects, compositions can comprise ~2, ~3, or ~4 or more ionic surfactants. In aspects, compositions can comprise ~2, ~3, or ~4 or more ionic surfactants. In aspects, compositions can comprise a single ionic surfactant in addition to 2 or more non-ionic surfactants. In aspects, compositions can comprise a single non-ionic surfactant in addition to 2 or more ionic surfactants. For example, in aspects compositions comprise a polysorbate compound (such as, e.g., polysorbate-80), a polyoxyl-ethylated castor oil (such as, e.g., a Cremophor® such as Cremophor® EL or Cremophor® RH-40 or their equivalents), or both a polysorbate and a polyoxyl-ethylated castor oil.

In aspects, one or more surfactant(s), which as stated, in aspects can also provide DOS suspension properties, e.g., polysorbate-80, is present in the compositions provided by the invention in an amount representing between about 1-20 mg/mL, such as between ~2-~20 mg/mL, ~2-~18 mg/mL, ~2-~16 mg/mL, ~2-~14 mg/mL, ~2-~12 mg/mL, or, e.g., ~2-~10 mg/mL, such as, e.g., between ~4-~20 mg/mL, ~6-~20 mg/mL, ~8-~20 mg/mL, ~10-~20 mg/mL, as in, e.g., between ~2-~18 mg/mL, ~4-~16 mg/mL, ~6-~14 mg/mL, ~8-~12 mg/mL, ~9-~11 mg/mL, or, e.g., about 10 mg/mL. In aspects, the surfactant is polysorbate-80.

In aspects, one or more non-ionic surfactant(s), which, as stated, in aspects can also provide DOS suspension properties, is an effective amount of polyoxyl-ethylated castor oil, wherein the polyoxyl-ethylated castor oil is present in an amount of between about 0.05-about 1.5 wt. %, such as, e.g., between ~0.05-~1.4 wt. %, ~0.05-~1.5 wt. %, ~0.05-~1.3 wt. % ~0.05-~1.2 wt. % ~0.05-~1.1 wt. %, or ~0.05-~1 wt. %, such as, e.g., between about ~0.06-~1.5 wt. %, ~0.07-~1.5 wt. %, ~0.08-~1.5 wt. %, ~0.09-~1.5 wt. %, ~0.1-~1.5 wt. %, such as, e.g., between about ~0.02-~1.4 wt. %, ~0.04-~1.3 wt. %, ~0.06-~1.2 wt. %, or, e.g., ~0.08-~1.1 wt. %, such as, e.g., ~0.1-~1 wt. %.

In this and any other excipient aspect of the invention, the invention also can be characterized as comprising a "means" for performing the function(s) associated with a type of excipient (e.g., such agents can be classified as "means for controlling surface tension", "means for improving spreadability", "means for increasing wettability", or "surfactant means" and the like). In such a respect, any known equivalents of such named agents can also be, e.g., are, incorporated into compositions or methods of the invention.

In aspects, one or more surfactants, such as, e.g., sodium citrate, is present in compositions in an amount of between about 0.5-20 mg/mL, such as, e.g., between ~0.6-~20 mg/mL, ~0.7-~20 mg/mL, ~0.8-~20 mg/mL, ~0.9-~20 mg/mL, or, e.g., ~1-~20 mg/mL, such as, e.g., ~0.5-~19 mg/mL, ~0.5-~18 mg/mL, ~0.5-~17 mg/mL, ~0.5-~16 mg/mL, ~0.5-~15 mg/mL, ~0.5-~14 mg/mL, ~0.5-~13 mg/mL, ~0.5-~12 mg/mL, ~0.5-~11 mg/mL, or ~0.5-~10 mg/mL, such as, e.g., between ~0.6-~18 mg/mL, ~0.7-~16 mg/mL, ~0.8-~14 mg/mL, ~0.9-~12 mg/mL, or, e.g., between about 1-about 10 mg/mL.

Viscoelasticity Agent(s)

In aspects, compositions comprise one or more compounds which exhibit DOS viscoelastic behavior or impart DOS viscoelastic characteristics to a composition in which they are present. Viscoelastic behavior is a combination of a compound providing elasticity behavior, e.g., returning to an original shape, size, or both after having been altered due to exposure to a sufficient force (e.g., a polymer returning to an original shape, size, or both after having been stretched), and viscous behavior, e.g., providing a DOS resistance to flow or motion. In aspects, a viscoelasticity agent can be any pharmaceutically acceptable or ophthalmologically suitable viscoelasticity agent, such as, e.g., chondroitin sulfate, hyaluronic acid, derivatives of cellulose including methylcellulose, polyacrylamide, polyvinyl alcohol, polyvinyl pyrrolidone (PVP), carbomers (weakly crosslinked polyacrylic acids), collagen, and the like, or any ophthalmologically suitable derivatives, e.g., salts thereof (e.g., sodium hyaluronate), or combinations of any two or more such compounds, or equivalents thereof.

In aspects, a viscoelasticity agent demonstrates ≥1 additional DOS functions within a composition, such as, e.g., demonstrating DOS suspension activity. For example, hyaluronic acid is characterizable as both a viscoelasticity agent and a suspension agent.

In aspects, viscoelasticity agent(s) acts synergistically with one or more other viscoelasticity agents. That is, for example, a viscosity of the composition can be established which is DOS, such as, e.g., substantially, higher than would be expected mathematically when defined amounts of two or more viscoelasticity agents are provided. For example, in aspects, compositions comprise hyaluronic acid and chondroitin sulfate. In such aspects, compositions can be formulated such that the viscosity of the composition is measurably higher than would be expected mathematically based on the individual quantities of each agent, such as, e.g., as much as about 10, ~11, ~12, ~13, ~14, ~15, ~16, ~17, ~18, ~19, or ~20× higher than what would be expected mathematically based on the individual quantities of each agent.

In this and any other excipient aspect of the invention, the invention also can be characterized as comprising a "means" for providing viscoelastic property(ies) of the invention. In such a respect, any known equivalents of such named agents can also be, e.g., are, incorporated into compositions or methods of the invention.

In aspects, one or more viscoelasticity agents, such as, e.g., chondroitin sulfate, is present in compositions in an amount representing between about 1-100 mg/mL, such as, e.g., between ~1-~90 mg/mL, ~1-~80 mg/mL, ~1-~70 mg/mL, ~1-~60 mg/mL, or, e.g., ~1-~50 mg/mL, such as, e.g., between ~2-~100 mg/mL, ~3-~100 mg/mL, ~4-~100 mg/mL, ~5-~100 mg/mL, as in, e.g., between ~1.5-~90 mg/mL, ~2-~80 mg/mL, ~2.5-~70 mg/mL, ~3-~60 mg/mL, ~3.5-~50 mg/mL, ~4-~50 mg/mL, ~4.5-~50 mg/mL, or, e.g., between ~5-~50 mg/mL of chondroitin sulfate.

In aspects, compositions comprise between about 1-40 mg/mL of a viscoelastic agent, such as, e.g., hyaluronic acid, such as, e.g., comprising between about between ~1-~38 mg/mL, ~1-~36 mg/mL, ~1-~34 mg/mL, ~1-~32 mg/mL, ~1-~30 mg/mL, ~1-~28 mg/mL, ~1-~26 mg/mL, ~1-~24 mg/mL, ~1-~22 mg/mL, ~1-~24 mg/mL, ~1-~22 mg/mL, ~1-~20 mg/mL, as in, for example, ~1.1 to ~40 mg/mL, ~1.2-~40 mg/mL, ~1.3-40 mg/mL, ~1.4-40 mg/mL, ~1.5-~40 mg/mL, ~1.6-~40 mg/mL, ~1.7-~40 mg/mL, ~1.8-~40 mg/mL, or, e.g., ~1.9-~40 mg/mL, as in, for example, between ~1.1-~38 mg/mL, ~1.2-~36 mg/mL, ~1.3-~34 mg/mL, ~1.4-~32 mg/mL, ~1.5-~30 mg/mL, ~1.6-~28 mg/mL, ~1.7-~26 mg/mL, ~1.8-~24 mg/mL, ~1.9-~22 mg/mL, or, e.g., ~2.0-20 mg/mL of hyaluronic acid.

In aspects, compositions comprise between about 2-about 150 mg/mL of one or more viscoelasticity agents, such as, e.g., chondroitin sulfate and hyaluronic acid, such as, e.g., between ~2-~150 mg/mL, ~3-~150 mg/mL, ~4-~150 mg/mL, ~5-~150 mg/mL, ~6-~150 mg/mL, or, e.g., ~7-~150 mg/mL, such as, e.g., between ~2-~140 mg/mL, ~2-~130 mg/mL, ~2-~120 mg/mL, ~2-~100 mg/mL, ~2-~100 mg/mL, ~2-~90 mg/mL, ~2-~80 mg/mL, or, e.g., ~2-~70 mg/mL, such as, e.g., ~3-~130 mg/mL, ~4-~110 mg/mL, ~5-~100 mg/mL, ~6-~80 mg/mL, or, e.g., between ~7-~70 mg/mL of one or more viscoelasticity agents.

Sequestering Agent(s)

In aspects, compositions provided by the invention comprise one or more ophthalmologically suitable sequestration agents (e.g., sequestering compounds). In alternative aspects, compositions provided by the invention do not comprise any component characterizable as a sequestering compound. Terms such as "sequestration agent" or "sequestering compound" generally refer to a substance used in the ophthalmic compositions to link metal ions or molecules together to form chelates (however, such different terminology can be used to describe compounds differing from chelating compounds in their ability to bind together two or more metal ions).

In aspects, a sequestration agent can be any ophthalmologically suitable sequestration agent, such as, e.g., aminocarboxylic acid-based products, phosphates and phosphonates, hydroxy carboxylates, polyacrylates, sugar acrylates, acetic acid, oxalic acid, gluconic acid, citric acid, sodium citrate, etc., or any ophthalmologically acceptable derivative, e.g., salts thereof, or combinations of any two or more such compounds, or equivalents thereof.

In certain aspects, compositions comprise sodium citrate. In aspects, sodium citrate can provide one or more activities in addition to acting as a sequestration agent, such as, e.g., providing buffering activity, emulsification activity, preservative activity, or any combination thereof.

In this and any other excipient aspect of the invention, the invention also can be characterized as comprising a "means" for sequestration of ingredients of composition(s) of the invention. In such a respect, any known equivalents of such named agents can also be, e.g., are, incorporated into compositions or methods of the invention.

In aspects, one or more sequestration agents, such as, e.g., sodium citrate, is present in compositions in an amount of between about 0.5-20 mg/mL, such as, e.g., between ~0.6-~20 mg/mL, ~0.7-~20 mg/mL, ~0.8-~20 mg/mL, ~0.9-~20 mg/mL, or, e.g., ~1-~20 mg/mL, such as, e.g., ~0.5-~19 mg/mL, ~0.5-~18 mg/mL, ~0.5-~17 mg/mL, ~0.5-~16 mg/mL, ~0.5-~15 mg/mL, ~0.5-~14 mg/mL, ~0.5-~13 mg/mL, ~0.5-~12 mg/mL, ~0.5-~11 mg/mL, or ~0.5-~10 mg/mL, such as, e.g., between ~0.6-~18 mg/mL, ~0.7-~16 mg/mL, ~0.8-~14 mg/mL, ~0.9-~12 mg/mL, or, e.g., between about 1-about 10 mg/mL.

Vehicle Component(s)

In aspects, compositions provided by the invention comprise an ophthalmologically suitable vehicle/carrier component, the vehicle component, in aspects, comprising one or more ophthalmologically suitable vehicle constituents/agents.

In certain aspects, a composition comprising a vehicle can be administered directly to the eye, as, in aspects, a vehicle provides the ingredients in a form and at a concentration wherein their application to the eye is safe and suitable for suitable for ocular administration. In aspects, composition(s) provided by the invention are typically provided with a vehicle component.

According to aspects, one or more vehicle constituents are present in a vehicle component of a composition in a sufficient amount to deliver the effective amounts of API(s) and, if present, one or more excipients.

In aspects, the invention provides for a vehicle component wherein the vehicle does not detectably or significantly adversely affect the stability of the composition, efficacy of the composition, or compatibility of ingredients of the composition, etc., at a period of at least about 2 weeks, e.g., at a period of ≥~1 month, ≥~6 weeks, ≥~2 months, ≥~10 weeks, ≥~3 months, ≥~14 weeks, ≥~4 months, ≥~18 weeks, ≥~5 months, ≥~22 months, ≥~6 months, or even longer (e.g., 2-36 months, 6-36 months, 12-24 months, or similar ranges provided with respect to other ingredients/compositions described herein, etc.).

In aspects, a vehicle component in a composition provided by the invention is an ophthalmologically suitable vehicle capable of serving as a vehicle of a composition having a pH of, e.g., between about ~5.0-~9.0, such as between ~5.5-~8.8, e.g., ~6-~8.6, or, e.g., between about ~5.5-~8.5. In aspects, the vehicle, does not have a pH lower than about 5.0. In aspects, a vehicle of the composition(s) herein does not detectably or significantly negatively impact any other component of the formulation, such as, e.g., a vehicle does not detectably or significantly reduce the efficacy of any one or more quinolone antibiotic components, any one or more anti-inflammatory steroid components, or both (e.g., reduce microbial inhibitory effect or reduce anti-inflammatory effect), or any other API or excipient present in the composition.

In aspects any ophthalmologically suitable and pharmaceutically acceptable vehicle is used in a composition provided by the invention. In aspects, exemplary vehicles used in a composition described herein comprise, e.g., a lipid vehicle, a gel vehicle, an oil-based vehicle, an emulsion vehicle, an emulsifier-containing vehicle that forms an emulsion when mixed with other components, or, a solution vehicle, e.g., an aqueous solution vehicle. In aspects, the carrier is an aqueous carrier. In aspects, the carrier is mostly, generally only, essentially only, substantially only, or only composed of water, e.g., water for injection (WFI) (a sterile, solute-free preparation of distilled water). In alternative aspects, other ophthalmologically suitable aqueous carriers which do not adversely affect the stability of the composition(s) may be used, such as, e.g., deionized water.

In aspects, a vehicle is an aqueous or a non-aqueous vehicle; in aspects, the vehicle is a combination vehicle, comprised of a combination two or more vehicles described above, such as a combination of an aqueous and a non-aqueous vehicle.

In aspects, a composition can be characterized as comprising "vehicle means" comprising such types of vehicles or known equivalents thereof, or combinations of any thereof.

According to aspects, the vehicle does not comprise any detectable, significant, or intentionally added amount of any deuterated vehicle or, in aspects, any deuteration, e.g., the vehicle can mostly, generally, or only comprise non-deuterated water or otherwise lack any deuterated vehicles, other excipients, or components in general. In alternative aspects, a composition comprises one or more components/ingredients, such as, e.g., a vehicle ingredient, which comprises deuteration (e.g., comprises the intentional replacement of one or more hydrogen atoms on a vehicle compound with one or more deuterium atoms), such as, e.g., deuterated water.

In this and any other excipient aspect of the invention, the invention also can be characterized as comprising a vehicle "means" of the invention (e.g., means of carrying and delivering ingredients of the composition(s). In such a respect, any known equivalents of such named agents can also be, e.g., are, incorporated into compositions or methods of the invention.

In aspects, a vehicle can be present in the compositions provided by the invention in an amount representing at least about 50 w/v %, ≥~55 w/v %, ≥~60 w/v %, ≥~65 w/v %, ≥~70 w/v %, ≥~75 w/v %, ≥~80 w/v %, ≥~85 w/v %, ≥~90 w/v %, ≥~95 w/v %, ≥~97 w/v %, ≥~98 w/v %, ≥~99 w/v % of the composition. In aspects, the vehicle is mostly, is generally, is essentially, or is entirely composed of water.

Penetration Enhancer(s)

In aspects, compositions provided by the invention comprise ophthalmologically suitable penetration enhancer(s). In alternative aspects, compositions provided by the invention do not comprise any component characterizable as a penetration enhancer. In general, a "penetration enhancer" refers to a substance used in the ophthalmic compositions to penetration of one or more compounds of the compositions, e.g., increasing the access of one or more compounds of the composition to deeper layers or regions of ocular tissue in an amount more than, or at a rate faster than, the compound would otherwise be able to penetrate ocular tissue.

In aspects, a penetration enhancer can be any ophthalmologically suitable penetration enhancer, such as, e.g., quaternary ammonium compounds polyoxyethylene sorbitan fatty acid esters, tocopherol polyethylene glycol succinate (TPGS), poly-arginine, polyserine, tromethamine (tris), sesame seed oil or oils having similar compositions and functional characteristics suitable for ophthalmic use, or any ophthalmologically suitable derivatives, e.g., salts thereof, or combinations of any two or more such compounds, or equivalents thereof. Polyoxyethylene sorbitan fatty acid esters can include but may not be limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In respects, polyoxyethylene sorbitan fatty acid ester ingredients can be a polyoxyethylene sorbitan oleate/polyoxyethylene sorbitan mono-oleate ester (e.g., polysorbate 80). This exemplifies how certain ingredients can perform >2 or even more than >3 functions or fulfill >2 or >3 categories of agents in a composition (e.g., polysorbate 80 can be characterized as a surfactant, a suspension agent, and a penetration enhancer).

In aspects, composition(s) provided by the invention comprise one or more quaternary ammonium compounds, such as, e.g., benzalkonium chlorides (abbreviated herein as BKC, and which is often abbreviated in the art as BAC, BAK, or BZK). Benzalkonium chlorides may also be referred to as alkyl dimethyl benzyl ammonium chlorides (ADBAC), alkyl dimethyl (phenylmethyl) chlorides, or ammonium alkyl dimethyl benzyl chlorides. In aspects, BKC can serve as a penetration enhancer, preservative, solubilizer, or any combination thereof. That is, in aspects, BKC can provide a detectable or significant increase in the penetration, e.g., the bioavailability, of one or more ingredients of the composition(s) or both, can provide preservation qualities such as those described in this section or in the art, or, e.g., can detectably or significantly improve upon the solubilization of any one or more APIs, such as any one or more quinolone antibiotic component constituents, one or more anti-inflammatory steroid component constituents, or a combination thereof.

In this and any other excipient aspect of the invention, the invention also can be characterized as comprising a "means" for increasing one or more constituents of the composition(s) of the invention. In such a respect, any known equivalents of such named agents can also be, e.g., are, incorporated into compositions or methods of the invention.

In aspects, one or more penetration enhancers, such as, e.g., benzalkonium chloride, are present in compositions in an amount of between about 0.01-0.1 mg/mL, such as, e.g., between ~0.02-~0.1 mg/mL, ~0.03-~0.1 mg/mL, ~0.04-~0.1 mg/mL, or, e.g., ~0.05-~0.1 mg/mL, such as, e.g., between ~0.01-~0.09 mg/mL, ~0.01-~0.08 mg/mL, ~0.01-~0.07 mg/mL, ~0.01-~0.06 mg/mL, or, e.g., ~0.01-~0.05 mg/mL, as in between about ~0.02-~0.09 mg/mL, ~0.03-~0.08 mg/mL, ~0.04-~0.07 mg/mL, ~0.04-~0.06 mg/mL, or, e.g., about 0.05 mg/mL benzalkonium chloride.

In aspects, one or more penetration enhancers, such as, e.g., polysorbate-80 or a polyoxy-ethylated castor oil, is present in the compositions provided by the invention in an amount representing between about 1-20 mg/mL, such as between ~2-~20 mg/mL, ~2-~18 mg/mL, ~2-~16 mg/mL, ~2-~14 mg/mL, ~2-~12 mg/mL, or, e.g., ~2-~10 mg/mL, such as, e.g., between ~4-~20 mg/mL, ~6-~20 mg/mL, ~8-~20 mg/mL, ~10-~20 mg/mL, as in, e.g., between ~2-~18 mg/mL, ~4-~16 mg/mL, ~6-~14 mg/mL, ~8-~12 mg/mL, ~9-~11 mg/mL, or, e.g., about 10 mg/mL. In aspects, the penetration enhancer is polysorbate-80.

In aspects, the total concentration of penetration enhancer(s) in compositions provided by the invention is between about 1-20 mg/mL, such as between ~2-~20 mg/mL, ~2-~18 mg/mL, ~2-~16 mg/mL, ~2-~14 mg/mL, ~2-~12 mg/mL, or, e.g., ~2-~10 mg/mL, such as, e.g., between ~4-~20 mg/mL, ~6-~20 mg/mL, ~8-~20 mg/mL, ~10-~20 mg/mL, as in, e.g., between ~2-~18 mg/mL, ~4-~16 mg/mL, ~6-~14 mg/mL, ~8-~12 mg/mL, ~9-~11 mg/mL, or, e.g., about 10-about 11 mg/mL.

Antioxidant(s)

In aspects, compositions provided by the invention comprise one or more ophthalmologically suitable antioxidants. In alternative aspects, compositions provided by the invention do not comprise any component characterizable as an antioxidant.

An "antioxidant" is typically understood as referring to a substance that preferentially reacts with oxygen, thereby detectably or significantly protecting other components of a composition to which it is added from premature degradation due to oxidation (e.g., protecting APIs that is known to be detectably/significantly susceptible to oxidation).

According to aspects, one or more antioxidant compounds are present in composition(s) of the invention which detectably or significantly improve API stability or reduce the amount of impurities, such as, e.g., providing for a composition which is stable under room temperature storage conditions, e.g., retains ≥90% of the one or more quinolone antibiotic component constituents and >90% of the one or more anti-inflammatory compounds when stored at about 25° C.+/−2° C. and about 40% relative humidity, at about 40° C. and not more than 25% relative humidity, or both, (ophthalmic product), or, e.g., 25° C. and 60% relative humidity or at 40° C. and 75% relative humidity for 3 months (injectable product), for at least about one month such as ≥~2 months or such as ≥~3 months, ≥~4 months, ≥~5 months, or, e.g., ≥~6 months.

For example, composition(s) provided by the invention can comprise one or more antioxidant agents which detectably improve the stability of the one or more quinolone antibiotic component constituents, one or more anti-inflammatory steroid component constituents, reduces the amount of impurities, enhances preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or for even longer periods (e.g., 3-24, 3-18, 3-12, 3-36, 4-12, 4-24, 4-36, 6-12, 6-18, 6-24, or 6-36 months).

In aspects, the invention provides composition(s) comprising one or more ophthalmologically suitable antioxidant agents effective at pH range of between ~5.5-~9.5, such as between ~6.0-~9.0, e.g., or, e.g., ~6.5-~8.5. In aspects, antioxidant compound(s) of the composition(s) herein do not detectably or significantly negatively impact any other component of the formulation, such as, e.g., they do not detectably or significantly reduce the efficacy of any one or more antimicrobial compound constituents, anti-inflammatory steroid component constituents (e.g., reduce microbial inhibitory effect or anti-inflammatory effect), or any other API or excipient present or which may be present in the composition.

In aspects any ophthalmologically suitable and pharmaceutically acceptable antioxidant is used in methods of the invention/incorporated in compositions of the invention, in any suitably effective amount(s). In aspects, exemplary antioxidant(s) in a composition described herein comprise, e.g., sodium ascorbate, ascorbic acid, thiamine, pyridoxine, histidine, cysteine, glutathione, sodium bisulphite, sodium sulphite, sodium metabisulphite, sodium thiosulphite, sodium formaldehyde sulphoxylate, acetylcysteine, cysteine, thioglycerol, thioglycollic acid, thiolactic acid, thieurea, dihithreitol, propyl gallate, butylated hydroxyanisole, butylated hydroxytoluene, tertiary butyl hydroquinone, ascorbyl palmitate, nordihydroguaiaretic acid and alpha-tocopherol, any ophthalmologically acceptable derivative, e.g., salts thereof, or combinations of any two or more such compounds.

In this and any other excipient aspect of the invention, the invention also can be characterized as comprising a "means" for providing antioxidant activity to composition(s) of the invention. In such a respect, any known equivalents of such named agents can also be, e.g., are, incorporated into compositions or methods of the invention.

In aspects, one or more antioxidant compound(s)/agent(s) can be present in the compositions provided by the invention in an amount representing between about 0.001 w/v. %-about 2 w/v. % of the composition, such as, e.g., ~0.001 w/v. %-~1.8 w/v. %, ~0.001 w/v. %-~1.6 w/v. %, ~0.001 w/v. %-~1.4 w/v. %, ~0.001 w/v. %-~1.2 w/v. %, ~0.08 w/v. %-~1 w/v. %, or. e.g., ~0.05-~1 w/v. % of the composition.

Additional APIs (or Lack Thereof)

As noted above, in aspects, compositions provided by the invention comprise quinolone antibiotic component(s), anti-inflammatory steroid component(s), suspension component(s), and no detectable or significant amounts of any additional active pharmaceutical ingredients.

In certain aspects, compositions provided by the invention comprise quinolone antibiotic component(s), anti-inflammatory steroid component(s), suspension component(s), and an effective and suitable amount of at least one additional API.

According to aspects, compositions of the invention can comprise one or more additional ophthalmologically suitable APIs in addition to the quinolone antibiotic component(s), anti-inflammatory steroid component(s), and suspension component(s) in any effective amount which provides for the API to affect the desired effect. In aspects, an additional API can be present in an amount effective in detectably or significantly increasing the efficacy of the quinolone antibiotic component, detectably or significantly increasing the efficacy of the anti-inflammatory steroid component, or detectably or significantly increasing the therapeutic usefulness or clinical efficacy of the composition, e.g., demonstrating a detectable or significant beneficial effect in the recipient of the composition. In aspects, the one or more additional active pharmaceutical ingredients can provide a detectable or significant increase in anti-inflammatory strength or activity of the composition. In aspects, the one or more additional APIs can provide a detectable or significant increase in the microbial inhibition or killing strength or activity of the composition. In aspects, the one or more additional APIs can provide a detectable or significant, e.g., clinically significant effect, different from antimicrobial or anti-inflammatory activity.

In aspects, composition(s) provided by the invention can comprise one or more additional APIs in addition to quinolone antibiotic component(s), anti-inflammatory steroid component(s), and suspension component(s), wherein the one or more additional APIs are stable within the composition(s) at a pH of between, e.g., ~5.0-~9.0, such as between ~6.0-~9.0, e.g., ~6.5-~8.5, for a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more.

In aspects, any one or more additional APIs of the composition(s) provided by the invention do not detectably or significantly negatively impact any other component of the formulation, such as, e.g., they do not detectably or significantly reduce the efficacy of any one or more quinolone antibiotic component constituent(s), anti-inflammatory constituent(s), (e.g., reduce microbial inhibition or killing effect, or reduce anti-inflammatory effect) or any other API or excipient present in the composition.

In aspects any ophthalmologically suitable and pharmaceutically acceptable API can be used. In aspects, APIs present in a composition provided by the invention in addition to one constituents of the quinolone antibiotic component, or anti-inflammatory steroid component, can be any one or more of, e.g., antineoplastic agent, anti-allergic agent, glaucoma-treating agent, intraocular pressure reducing agent, etc., such as any ophthalmologically suitable compound which imparts a benefit to the eye of the recipient other than anti-microbial or anti-inflammatory effect. In aspects, compositions provided by the invention can comprise one or more pharmaceutically acceptable and ophthalmological anti-microbial agents, e.g., an antibacterial, a synthetic antibacterial, an antifungal, a synthetic antifungal, wherein the anti-microbial agent is present in an amount effective in detectably or significantly treating, preventing, or inhibiting development of or progression of a microbial growth, e.g., a bacterial growth or a fungal growth.

In one aspect, the invention provides compositions comprising one or more antimicrobials, e.g., one or more antibiotics, other than the above-described quinolone antibiotic API(s). In certain aspects, suitable antibacterial/antibiotics can be any ophthalmologically suitable antibacterial/antibiotic. In aspects, suitable antibacterial/antibiotics for combination therapy are, for example, aminoglycosides for example amikacin, apramycin, arbekacin, bambermycins, butirosin, dibekacin, dihydrostreptomycin, fortimicin(s), gentamicin, tobramycin, isepamicin, kanamycin, micronomicin, neomycin, neomycin undecylenate, netilmicin, paromomycin, ribostamycin, sisomicin, spectinomycin, streptomycin, trospectomycin; amphenicois for example azidamfenicol, chloramphenicol, florfenicol, thiamphenicol), ansamycins (e.g., rifamide, rifampin, rifamycin sv, rifapentine, rifaximin; beta-lactams for example carbacephems include loracarbef; carbapenems for example biapenem, imipenem, meropenem, panipenem; cephalosporins for example cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, cefloranide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, ceifuzonam, cephacetrile sodium, cephalexin, cephaloglycin, cephaloridine, cephalosporin, cephalothin, cephapirin sodium, cephradine, pivcefalexin; cephamycins for example cefbuperazone, cefmetazole, cefininox, cefotetan, cefoxitin; monobactams for example aztreonam, carumonam, tigemonam), oxacephems, flomoxef, moxalactam; penicillins for example amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin and other like ritipenem; lincosamides for example clindamycin and lincomycin; macrolides for example azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin; polypeptides for example amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin and zinc bacitracin; tetracyclines for example apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline and, e.g., tetracycline, and pharmaceutically acceptable salts thereof, and mixtures thereof. In aspects, suitable synthetic antibacterials suitable for combination therapy are, for example, 2,4-diaminopyrimidines for example brodimoprim, tetroxoprim, trimethoprim; nitrofurans for example furaltadone, furazolium chloride, nifuradene, nifuratel, nifurfoline, nifurpirinol, nifurprazine, nifurtoinol, nitrofurantoin; quinolones and analogs for example cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin; sulfonamides for example acetyl sulfamethoxypyrazine, benzylsulfamide, chloramine-b, chloramine-t, dichloramine-t, N2-Formylsulfisomidine, N4-β-d-Glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole; sulfones for example acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone; and others like clofoctol, hexedine, methenamine, methenamine anhydromethylene-citrate, methenamine hippurate, methenamine mandelate, methenamine sulfosalicylate, nitroxoline, taurolidine, and, e.g., xibornol, and pharmaceutically acceptable salts thereof, and mixtures thereof. In general, any description of an additional API herein with respect to compositions implicitly provides support for the use of such additional API(s) in combination therapy methods, wherein such agents are administered/delivered separately to a subject, such as a patient, in combination with composition(s) of the invention (and vice versa). In aspects, antifungal agents suitable for combination compositions or combination therapy with compositions of the invention are, for example, polyenes e.g., amphotericin b, candicidin, dennostatin, filipin, fungichromin, hachimycin, hamycin, lucensomycin, mepartricin, natamycin, nystatin, pecilocin, perimycin, azaserine, griseofulvin, oligomycins, neomycin undecylenate, pyrrolnitrin, siccanin, tubercidin, and, e.g., viridin, and pharmaceutically acceptable salts thereof, and mixtures thereof. Examples of suitable synthetic antifungals include, e.g., allylamines for example butenafine, naftifine, terbinafine, imidazoles for example bifonazole, butoconazole, chlordantoin, chlormidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole; thiocarbamates for example tolciclate, tolindate, tolnaftate; triazoles for example fluconazole, itraconazole, saperconazole, terconazole and others like acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and, e.g., zinc propionate, and pharmaceutically acceptable salts thereof, and mixtures thereof. In aspects, antineoplastic agents suitable for combination therapy are, for example, ophthalmologically suitable forms of mitomycin C or fluorouracil (5FU), or Intron A, or ophthalmologically suitable forms of methotrexate, cytarabine (Ara-C), thiotepa, chlorambucil, dacarbazine, or temozolamide, etc. In aspects, anti-allergic agents suitable for combination therapy or combination compositions are, for example, ophthalmologically suitable antihistamines (e.g., levocabastine, emedastine, bilastine, cetirizine, etc.), ophthalmologically suitable mast-cell stabilizers (e.g., cromolyn, nedocromil, etc.), ophthalmologically suitable dual-activity agents (providing both antihistamine and mast-cell inhibition activity, such as, e.g., olopatadine, bepotastine, alcaftadine, etc.), ophthalmologically suitable corticosteroids (e.g., lotepredol etabonate, loteprednol, mapracorat, prednisolone acetate, prednisolone phosphate, dexamethasone, etc.), ophthalmologically suitable non-steroidal anti-inflammatory drugs (such as, e.g., those disclosed above, or, e.g., specifically be, e.g., diclofenac sodium, nepafenac, etc.), ophthalmologically suitable decongestants (e.g., brimonidine, etc.), ophthalmologically suitable immunomodulators (e.g., cyclosporine A, tacrolimus, etc.) and others such as ophthalmologically suitable cannabis preparations, immunobiologicals, etc. In certain aspects, intraocular pressure-treating agents or glaucoma-treating agents suitable for combination therapy are, for example, beta blockers (e.g., nonselective beta blockers such as, e.g., timolol maleate, levobunolol, carteolol, metipranolol, etc. or, e.g., selective beta blockers such as, e.g., betaxolol, etc.), mimotics (e.g., pilocarpine, etc.), carbonic anhydrase inhibitors (e.g., dorzolamide, brinzolamide, etc.), sympathomimetics (e.g., epinephrine-like sympathomimetics such as, e.g., dipivefrin, etc. or, e.g., clonidine-like sympathomimetics such as, e.g., brimonidine, apraclonidine, etc.), prostaglandin analogs (e.g., latanoprost, travoprost, tafluprost, bimatoprost, latanoprosten bunod, etc.), etc. In certain aspects, antiviral agents suitable for combination therapy are, for example, idoxuridine (IDU), iododesoxycytidine (IDC), vidarabine (Ara-A), trifluridine (TFT), aciclovir, ganciclovir, trifluridine, idoxuridine, ophthalmologically suitable formulations of valganciclovir, foscarnet, etc. In aspects, anti-mycotic agents suitable for combination therapy are, for example, ophthalmologically suitable polyenes (e.g., amphotericin B (AMB), nystatin, nytamycin (NTM), etc.), ophthalmologically suitable azoles (e.g., imidazoles or triazoles, including, e.g., miconazole (MCZ), econazole (ECZ), ketoconazole (KCZ), itraconazole (ICZ), fluconazole), voriconazole, posaconazole (PCZ), etc.), ophthalmologically suitable pyrimidines (e.g., 5-fluorocystine (5-FC), flucytosine, etc.), ophthalmologically suitable echinocandins (e.g., caspofungin (CFG), micafungin (MFG), etc.), etc.

Optionally Excluded Ingredients

In aspects, compositions provided by the invention can be described by ingredients which are not present. In aspects, compositions herein do not comprise any one or more of a co-polymer. In aspects, compositions herein do not comprise any one or more of a block copolymer. In aspects, compositions exclude block copolymers of poly(ethylene oxide) and poly(propylene oxide). In aspects, compositions herein do not comprise any one or more of specific block copolymers. In aspects, compositions herein do not comprise non-ionic block copolymers. In aspects, compositions herein do not comprise a non-ionic polyoxyethylene-polyoxypropylene block copolymer having the chemical structure:

HO—(CH2-CH2-O)$x$-(C3H6-O)$y$-(CH2-CH2-O)$x$-H, wherein x is an integer having the value of at least 8 (such as, e.g., ≥8, ≥9, ≥10, ≥11, ≥12 or more) and y is an integer having the value of at least 38 (such as, e.g., ≥38, ≥39, ≥40, ≥41, ≥42, ≥43, ≥44, ≥45 or more). In specific aspects, compositions exclude Poloxamer-407 (BASF), the difunctional block copolymer terminating in primary hydroxy groups marketed as Pluronic® F-127 (BASF Corporation), and the non-ionic di-hydroxyfunctional block copolymer (poly alkylene oxide block copolymer) marketed as Synperonic™ PE/F 127 (Croda Healthcare).

In aspects, compositions herein do no comprise xanthan gum. In aspects, compositions do not comprise hydroxypropyl methyl cellulose.

Means/Steps for Performing Functions

In aspects, compositions provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, compositions provided by the invention comprise means for chelation, such means for chelation detectably or significantly improving the stability of the one or more quinolone antibiotic component constituents, detectably or significantly improving the stability of one or more anti-inflammatory steroid component constituents, detectably enhancing the effectiveness of one or more preservatives, or any combination thereof ("chelation means"). Support for chelation means can be found in, e.g., the section entitled "Chelating Agent(s)."

In one aspect, compositions comprise means for preserving the composition(s), e.g., detectably or significantly inhibit microbial growth, detectably or significantly reducing the number of impurities or detectably or significantly improving the stability of the compositions such that compositions remain safe and suitable for administration after storage of at least about 1 month, e.g., ~2 months, or e.g., ~3 months or more after manufacturing at room temperature (25° C. and about 40% relative humidity, about 40° C. and no more than 25% relative humidity, or both (ophthalmic product), or, e.g., 25° C. and 60% relative humidity or at 40° C. and 75% relative humidity for 3 months (injectable product)) ("preservation means"). Support for preservation means can be found in, e.g., the section entitled "Preservative(s)."

In one aspect, compositions provided by the invention comprise means for providing a suitable tonicity of the composition(s), providing a suitable osmolality of the composition(s), e.g., means for providing composition(s) which do not cause detectable or significant ocular irritation due to tonicity when provided according to instructions ("tonicity means"). Support for tonicity means can be found in, e.g., the section entitled "Tonicity Agent(s)."

In aspects, compositions provided by the invention comprise means for buffering the addition of, or buffering the presence of (if/when such compositions are placed into an environment having or compositions develop or are exposed to), elements or compositions of a different pH or which are capable of otherwise detectably or significantly modifying the pH of the compositions ("buffering means"). Exemplary buffering means are described in, e.g., the section entitled "Buffer(s)/Buffering Agent(s)."

In one aspect, compositions provided by the invention comprise means for adjusting the pH of the composition(s), providing a suitable or target pH of the composition(s) of between about, e.g., ~6-~9, such as, e.g., ~6.2-~8.8, or, e.g., between about 6.5-about 8.5, such as, between about 6.8-about 7.2 (e.g., 7.0±0.2) ("pH adjusting means"). Support for pH adjusting means can be found in, e.g., the section entitled "pH Adjusting Agent(s)."

In one aspect, compositions provided by the invention comprise means for modifying the surface tension of the compositions which in aspects provides means for increasing the spreading, e.g., the wetting, of the ophthalmic compositions ("surfactant means"). Support for surfactant means can be found in, e.g., the section entitled "Surfactant(s)."

In one aspect, compositions provided by the invention comprise means for modifying the viscoelasticity of the composition(s), providing viscoelastic protection of the eye or ocular features ("viscoelasticity means"). Support for viscoelasticity means can be found in, e.g., the section entitled "Viscoelasticity Agent(s)."

In one aspect, compositions provided by the invention comprise means for linking metal ions or molecules together to form chelates (complex ring-like structures which tend to be stable and resist decomposition), doing so by binding to multiple metal ions at a time, limiting their ability to react with other compounds ("sequestration means"). "Sequestration means" are distinct from "chelation means" in that "sequestration means" bind multiple metal ions at once while "chelation means" bind a single metal ion at a time. Support for "sequestration means" can be found in, e.g., the section entitled "Sequestering Agent(s)."

In one aspect, compositions provided by the invention comprise means for providing compositions of the invention, e.g., delivering APIs and other ingredients of the composition, as, e.g., liquid compositions; e.g., providing a carrier or vehicle for the API's and any one or more other excipients of the composition(s) ("vehicle means"). Support for vehicle means can be found in, e.g., the section entitled "Vehicle Component(s)."

In one aspect, compositions provided by the invention comprise means for increasing the penetration of one or more compounds of the compositions, e.g., increasing the access of one or more compounds of the composition to deeper layers or regions of ocular tissue ("penetration means"). Support for penetration means can be found in, e.g., the section entitled "Penetration Enhancer(s)."

In one aspect, compositions provided by the invention comprise means for protecting APIs from oxidation, e.g., means for providing antioxidant protection of API(s), such means for antioxidant protection of API(s) detectably or significantly improving the stability of the one or more quinolone antibiotic component constituents, detectably or significantly improving the stability of one or more anti-inflammatory steroid component constituents, detectably or significantly reducing impurities detected at time points 2 weeks, 1 months, 2 months, or 3 months or more after manufacturing, or any combination thereof ("antioxidant means"). Support for antioxidant means can be found in, e.g., the section entitled "Antioxidant(s)."

In one aspect, compositions provided by the invention comprise means for providing compositions of the invention with detectable or significant increases in clinically relevant anti-inflammatory effect over that provided by the quinolone antibiotic component alone ("anti-inflammatory means"). Support for anti-inflammatory means can be found in, e.g., the section entitled "Anti-inflammatory Component."

In one aspect, compositions provided by the invention comprise means for detectably or significantly treating, preventing, or inhibiting development of, or progression of, microbial growth, e.g., bacterial growth, such as that present in an ocular infection ("antimicrobial means"). In aspects, such antimicrobial means for inhibiting microbial growth can be present in the composition in addition to (e.g., separately from) any one or more other preservation means (e.g., means for detectably or significantly reducing impurities or detectably or significantly extending stability over a storage period) which may be present in the composition. Support for antimicrobial means can be found in, e.g., the section entitled "Quinolone Antibiotic Component."

General Characteristics of Compositions

Suspension

In aspects, compositions provided by the invention are characterizable as suspensions. In general, a "suspension" is intended to take on its standard meaning in the art, that is a heterogeneous mixture of a fluid comprising solid particles which are not dissolved but are rather maintained dispersed throughout the fluid. Particles of suspensions are generally capable of settling out of the fluid given enough time or when placed under certain conditions. In aspects, compositions herein comprise a suspension component which aids in extending the length of time particles of the composition remain in suspension without DOS settling or flocculating. Suspension components and compounds/agents/constituents thereof are discussed in detail elsewhere herein.

In aspects, compositions provided by the invention are capable of maintaining particles therein, e.g., particles of one or more steroidal anti-inflammatory compound(s), for a period of at least about 5 minutes, e.g., ≥~10 minutes, ≥~20 minutes, ≥~30 minutes, ≥~45 minutes, ≥~1 hour, ≥~3 hours, ≥~6 hours, ≥~12 hours, ≥~18 hours, ≥~24 hours, ≥~2 days, ≥~3 days, ≥~4 days, ≥~5 days, ≥~6 days, ≥~7 days, ≥~2 weeks, ≥~3 weeks, ≥~4 weeks, ≥~2 months, ≥~3 months, ≥~4 months, ≥~5 months, or, e.g., ≥~6 months or longer.

In aspects, compositions herein effectively maintain ≥1 non-dissolved compounds in suspension such that they are unable to negatively interfere with one or more other compounds of the composition, such that they are unable to DOS negatively impact the uniformity of the composition, e.g., they are unable to detectably or significantly agglomerate/flocculate (here, the two terms are used synonymously), or both. In aspects, an exemplary defining characteristic of the inventive compositions herein is their ability to maintain both one or more fluoroquinolone compound(s) and one or more anti-inflammatory compound(s) (e.g., steroidal, non-steroidal, or both steroidal and non-steroidal anti-inflammatory compounds) effectively in suspension such that the composition maintains sufficient deflocculation to make the compositions suitable for intraocular use for a period of at least about 3 months when stored under standard storage conditions (e.g., at about 25° C. and about 40% relative humidity, or, e.g., at about 40° C. and no more than 25% relative humidity, or both (ophthalmic product), or, e.g., 25° C. and 60% relative humidity or at 40° C. and 75% relative humidity for 3 months (injectable product)).

In aspects, compositions are characterized as not exhibiting sustained physical stability, in terms of, for example, detectable or significant flocculation, coagulation, or clumping, which cannot be overcome through moderate agitation, such as manual agitation for times described elsewhere herein. In other words, in aspects, compositions do not exhibit detectable or significant sustained coagulation, clumping, or flocculation.

Particle Size

In aspects, compositions provided by the invention comprise particles in suspension. In aspects, the particles in suspension have an average diameter in any direction of less than 5 µm, such as, e.g., <~4.5 µm, <~4 µm, <~3.5 µm, <~3 µm, <~2.5 µm, <~2 µm, <~1.5 µm, <~1 µm, or even less, such as <~0.5 µm, e.g., between about 0.5 µm-about 3 µm, as in between ~0.5-~2.5 µm, ~0.5-~2 µm, ~1.5-~2.5 µm, or ~0.5-~1 µm, such as, e.g., ~1-~3 µm, ~0.5-~1.5 µm, or, e.g. ~2-~2.5 µm.

In aspects, compositions designed for delivery by injection, e.g., by intracameral injection, comprise a particle size of less than about 2 µm, e.g., <~1.75 µm, <~1.5 µm, <~1.25 µm, <~1 µm, <~0.75 µm, or, e.g., <~0.5 µm, as in between about 0.5-about 1.5 µm.

In aspects, compositions designed for delivery as drops (e.g., via standard eye-drop administration methods known in the art) comprise a particle size of less than about 5 µm, such as, e.g., <~4.5 µm, <~4 µm, <~3.5 µm, <~3 µm, <~2.5 µm, or, e.g., <~2 µm, such as between about 2-about 3 µm.

In aspects, compositions comprising particles with an average size less than 5 µm, mostly comprising particles of less than 5 µm perform DOS better in terms of maintaining uniform size and/or shape characteristics, e.g., in the case of relatively uniform sized and sufficiently small particle compositions, over periods of time, such as those described elsewhere (e.g., >1 month, >2 months, >3 months, >6 months, >1 year, >18 months, or >2 years when maintained under typical FDA stability testing conditions, as described elsewhere or known in the art). In aspects, particles can be defined by an absolute, typical, or average size or shape.

In one aspect, the particle size of particles in suspension in compositions herein cannot DOS block trabecular meshwork of the eye, e.g., cannot DOS restrict flow of aqueous humor out of the eye. That is, in aspects, particle size of particles, and particle size of any two or more agglomerated particles, is sufficiently small so as to allow at least about 80%, ~~82%, ~~84%, ~~86%, ~~88%, ~~90%, ~90%, ~~92%, ~~94%, ~~96%, ~~98%, ~~99%, ~~99.5%, ~~99.75%, or, e.g. ~100% of unrestricted aqueous humor flow through the trabecular meshwork of the eye.

In aspects, most, generally all, substantially all, or all agglomeration of particles, e.g., any flocculation of particles, is resolved by shaking the compositions for a minimum of about 10 seconds, such as, e.g., at least about ~12 seconds, ~14 seconds, ~16 seconds, ~18 seconds, ~20 seconds, ~22 seconds, ~24 seconds, ~26 seconds, ~28 seconds, ~30 seconds, such as, e.g., at least about ~35 seconds, ~40 seconds, ~45 seconds, ~50 seconds, ~55 seconds, or, e.g., ~60 seconds. In aspects, most, generally all, substantially all, or all flocculation is resolved by shaking for less than about 60 seconds, such as by shaking for <~55 seconds, <~50 seconds, <~45 seconds, <~40 seconds, <~35 seconds, <~30 seconds, <~25 seconds, <~20 seconds, <~15 seconds, <~10 seconds, or, e.g., by shaking for less than about 5 seconds. In aspects, shaking for such period(s) of time results in less than about 40%, <~35%, <~30%, <~25%, <~20%, <~15%, <~10%, or, e.g., <~5% of the particles of the composition being flocculated, or, e.g., results in no DOS particle flocculation.

In one aspect, particles of composition(s) herein can be characterized as being mostly, generally, or substantially uniform in size, shape, or both, for example having mostly, generally, or substantially the same maximum diameter in any single direction, or for example being mostly, generally, or substantially spherical or other shape.

Average Diameter or Maximum Dimension Size of Particles

One possible way to characterize compositions of the invention is the average maximum size of the particles in any one dimension or the maximum average diameter in the case of particles that are spheroid or spherical in shape. It is to be understood that these concepts can be interchanged herein such that the description of any aspect with respect to a maximum average diameter, as applied to a spheroid particle for example, is to be understood as providing corresponding support for a non-spheroid particle having an average maximum size in any one dimension of a corresponding size.

In one aspect, at least about 50%, at least about 70%, at least about 80%, at least about 90%, at least about 95%, at least about 99%, or about 100% of the particles in the composition have a maximum diameter (or average maximum dimension) of less than about 5 μm, such as, e.g., ≤~4.5 μm, ≤~4 μm, ≤~3.5 μm, ≤~3 μm, ≤~2.5 μm, ≤~2 μm, ≤~1.5 μm, ≤~1 μm, or, e.g., even ≤~0.5 μm. In one aspect, the size of at least about 75%, at least about 85%, at least about 92.5%, or at least about 97.5% of the particles of the composition, or more, such as about 100% of the particles of the composition, are between about 0.5-about 1.5 μm in compositions provided by injection and between about 2-about 3 μm in compositions provided by drops.

Size Distribution of Particles and Methods of Production

Compositions of the invention also can be characterized on the basis of the size distribution of particles in the composition. In this respect it is worth noting that many compositions of the invention will comprise particles that vary in size due to differences that arise in the manufacturing process, handling, or for similar reasons. In aspects, compositions with relatively uniform sizes can offer advantageous properties including in aiding in injectability of the composition, aiding in the suspension characteristics of the compositions, etc.

In aspects, particles of the compositions provided by the invention are relatively uniform in size. The relative uniformity in particle size of the suspended particles of the compositions herein can be characterized by describing the coefficient of variation in particle size in the composition. E.g., in aspects, the maximum particle diameter coefficient of variation (CV) of particles of the composition is less than about 75%, <~70%, <~65%, <~60%, <~55%, <~50%, <~45%, <~40%, <~35%, <~30%, <~25%, <~20%, <~15%, <~12.5%, <~10%, or less than about 7.5%, e.g., <~7%, <~6%, or <~5%.

In aspects, particles of the compositions described herein can have a size distribution such that ≥~20%, such as ≥~22%, ≥~24%, ≥~26%, ≥~28%, ≥~30%, ≥~32%, ≥~34%, ≥~36%, ≥~38%, ≥~40%, ≥~42%, ≥~44%, ≥~46% ≥~48% or ≥~50%, such as ≥~52%, ≥~54%, ≥~56%, ≥~58%, ≥~60%, ≥~62%, ≥~64%, ≥~66%, ≥~68%, ≥~70%, ≥~72%, ≥~74%, ≥~76%, ≥~78%, or ≥~80% of the particles of the composition have a maximum particle diameter that is within about 75%, ~70%, ~65%, ~60%, ~65%, ~50%, ~48%, ~46%, ~44%, ~42%, ~40%, ~38%, ~36%, ~34%, ~32%, ~30%, ~28%, ~26%, ~24%, ~22%, ~20%, ~18%, ~16%, ~14%, ~12%, or, e.g., within ~10% of the average particle diameter of the particles in the composition. According to specific embodiments, at least about 65% of the particles of the composition have a maximum particle diameter that is within 35% of the average particle diameter of the particles in the composition. According to alternative specific embodiments, at least about 70% of the particles of the composition have a maximum particle diameter that is within about 33% of the average particle diameter of the particles in the composition. According to yet further embodiments, at least 33% of the particles have a maximum diameter that is within about 15% of the average particle diameter of particles in the composition. In yet another embodiment, at least about 40% of the particles have a maximum diameter that is within about 20% of the average particle diameter of the particles in the composition.

According to certain embodiments, less than about 50%, such as, <~40%, <~30%, <~20%, <~10%, or, e.g., <~5% of the particles of compositions herein have an average maximum dimension/diameter that is above 5 μm. According to certain embodiments, less than about 50%, such as, <~40%, <~30%, <~20%, <~10%, or, e.g., <~5% of the particles of compositions herein have an average maximum dimension/diameter that is below 0.1 μm. According to certain embodiments, compositions designed for injection comprise less than about 50%, such as, <~40%, <~30%, <~20%, <~10%, or, e.g., <~5% of the particles having have an average maximum dimension/diameter that is above 2 μm or below 0.1 μm. According to certain embodiments, compositions designed for administration by drops comprise less than about 50%, such as, <~40%, <~30%, <~20%, <~10%, or, e.g., <~5% of the particles having have an average maximum dimension/diameter that is above 4 μm or below 1 μm.

In some aspects, the particles of the inventive compositions can alternatively be described by their size relative to one another. According to certain embodiments, the particles in suspension within compositions herein have an average maximum diameter which is less than about 5 μm and greater than about 0.1 μm, and at least about 85%, ≥~90%, ≥~95%, or more (e.g., ≥~97.5% or ≥~99%) of the particles in suspension have an average maximum diameter that is within about 75%, ~80%, ~85%, ~90%, or within about ~95% or more of the average maximum diameter of at least about 75%, ~80%, ~85%, ~90%, or ~95% or more of the other particles in suspension.

In aspects, suspended particles of the compositions provided herein can also or alternatively be characterizable based on the shape of some, most, largely all, substantially all, or all of the particles in the composition. In aspects, particles of the invention can have any suitable shape. For example, the particles can have a "pollen" shape, a squircle shape, a disc shape, or other shape. In a typical aspect the particles have a relatively spherical or spheroid shape. The uniformity of shape of particles can be determined by comparison of the dimensions of the particles. In one aspect, the composition materially comprises, predominately comprises, largely consists of, substantially consists of, consists essentially of, or consists of particles having a relatively similar proportion in most dimensions, in at least 65% of dimensions, at least 75% of dimensions, at least 90% of dimensions, or in all dimensions. Dimensions in this respect means dimensions in all planes of the particles' three-dimensional shapes. E.g., at least about 50%, at least about 70%, at least about 85%, at least about 95%, or at least about 100% of the particles in aspects can be characterizable as having the same shape.

In aspects, particles will also have the same size, such that the proportions described above can be 1:1 or about 1:1. For example, where most, largely all, nearly all, or all of the particles in the composition are spherical/spheroid less than about 10% of particles can typically have a maximum diameter that is more than 40% greater than the average diameter of particles in the composition or less than about 40% of the average diameter of particles in the composition. For example, <~10%, <~9%, <~8%, <~7%, <~6%, <~5%, <~4%, <~3%, <~2%, or <~1%, such as <~0.9%, <~0.8%, <~0.7%, <~0.6%, <~0.5%, <~0.4%, <~0.3%, <~0.2%, <~0.1%, <~0.05%, or less than about 0.01% of particles have a maximum diameter that is more than about 40%, such as more about 42%, >~44%, >~46%, >~48%, >~50%, >~52%, >~54%, >~56%, >~58%, or >~60%, for example >~62%, >~64%, >~66%, >~68%, >~70%, >~72%, >~74%, >~76%, >~78%, >~80%, >~82%, >~84%, >~86%, >~88%, or more than about 90%, for example >~92%, >~94%, >~96%, >~98%, or more than approximately 99% larger or smaller than the average diameter of particles in the composition. According to one embodiment, less than 1% of particles have a maximum diameter that is more than 66% greater than the average diameter of particles in the composition or less than about 66% of the average diameter of particles in the composition. According to one embodiment, less than about 10% of the particles have a maximum diameter more than 50% greater or less than about 50% less than the average diameter of particles in the composition.

In one exemplary aspect, the invention provides compositions in which the diameter of at least about 80% of the particles of the composition can vary by no more than about 5% in any direction. That is, for example, >~80%, for example >~82%, >~84%, >~86%, >~88%, or for example >~90%, >~92%, >~94%, >~94%, >~96%, >~98%, >~99% or at least approximately 99.5% of the particles of the present invention vary by no more than about 15%, for example vary by <~14%, <~13%, <~12%, <~11%, <~10%, <~9%, <~8%, <~7%, <~6%, <~5%, <~4%, or even less, for example <~3%, <~2% or vary by no more than 1% in any direction, conferring a mostly spherical shape to the particles. According to specific embodiments, at least about 80% of the particles of the composition vary by no more than 15% in any direction. According to more specific embodiments, at least about 90% of the particles of the composition vary by no more than about 5% in any direction. According to one embodiment, at least about 80% of the particles of the composition vary by no more than about 2% in any direction, and according to yet further specific embodiments, at least about 85% of the particles of the present invention vary by no more than about 1% in any direction.

In another aspect, the invention provides particles wherein the diameter (or average maximum dimension, average dimension, and/or average minimum dimension) of at least 80% of the particles of the composition (e.g., at least about 90% of the particles or at least about 95% of the particles) varies by no more than 15% in any direction. In more particular aspects at least about 85%, at least about 85%, or at least about 99% of the particles have diameters that vary by 5% or less with respect to the average diameter of the particles in the composition. In still more precise aspects, at least about 50%, at least about 60%, at least about 70%, at least about 85%, or at least about 95% of the particles can have diameters that are within about 2% of the average particle diameter or even within ~1% of the average particle diameter.

Corneal Contact Time

In aspects, compositions provided by the invention comprise one or more ingredients which DOS increase corneal contact time of the composition over compositions lacking such a component. In aspects, such an ingredient is characterizable as any one or more of a suspension component or constituent of a suspension component, a viscoelasticity agent, or, e.g., a surfactant. In aspects, such a component DOS demonstrates two or more such functions, such as, e.g., a component which DOS increases corneal contact time of the compositions is characterizable both as a suspension component or constituent of a suspension component, a surfactant, or both. For example, in aspects, compositions comprise a suspension component wherein the suspension component DOS increases corneal contact time over compositions lacking such a suspension component. In aspects, the suspension component comprises hyaluronic acid, methylcellulose, carboxymethylcellulose (CMC), hydroxyethylcellulose, hydroxypropyl methylcellulose, gelatin, acacia, povidone, polyvinylpyrrolidone, polysorbates (e.g., polysorbate-80), polyoxyl-ethylated castor oil (e.g., Cremophor® EL or Cremophor® RH-40), and polyethylene glycols (PEGs), such as, e.g., PEG 400, PEG 3350, etc. or any ophthalmologically suitable derivative, prodrug, hydrate, salt, solvate, enantiomer, or polymorph thereof. In aspects, such compounds increase corneal contact time.

In aspects, compositions comprise a surfactant, wherein the surfactant DOS increases corneal contact time over compositions lacking such a surfactant. In aspects, the surfactant comprises lecithin and lecithin derivatives including pure phospholipids such as, e.g., soya phosphatidyl choline) and mixed phospholipids, sodium cholate, and hydroxylated phospholipids/hydroxylated lecithin; glycerol fatty acid esters including polyglycerol fatty acid esters, polyglycerol polyricinoleate, hydrogenated castor oils and propylene glycol fatty acid esters (such as, e.g., polyoxyethyleneglycerol triricinoleate, Cremophor® EL (macrogol-1500-glyceroltriricinoleate), Cremophor® RH-40, and monobutyl glycerol); polysorbates such as polysorbate-80; sorbitan fatty acid esters including sorbitan monolaurate and sorbitan monoleate; polyoxyethylene sorbitan fatty acid esters including polyethylene glycol sorbitan monolaurate and polyethylene glycol sorbitan monooleate; etc., including propylene glycol, PEGs (e.g., PEG 200), and cosurfactants such as alkanols (e.g., ethanol, propanol, butanol, etc.), alkane-diols (e.g., 1,2-propane diol, 1,2-butane diol, etc.), and alkane-polyols (glycerol, glucitol, polyethylene glycol, etc.), or derivatives thereof or combinations of any two or more of such compounds.

Non-Irritating Nature

In aspects, compositions provided by the invention are characterized as non-irritating. In aspects, compositions provided by the invention do not cause detectable or significant irritation in the majority of users of the composition. In aspects, irritation is not reported as a composition-associated adverse event in a population of test subjects or, in aspects, a detectable or significant amount of irritation is reported by no more than about 10%, e.g., by no more than ≤~9%, ≤~8%, ≤~7%, ≤~6%, ≤~5%, ≤~4%, ≤~3%, ≤~2%, ≤~1%, ≤~0.5%, or, e.g., ≤~0.1%, of a population of subjects in an appropriately conducted and controlled clinical trial. In aspects, compositions provided by the invention provide detectably or significantly less irritation (e.g., the level of irritation reported by a user is detectably or significantly less), less frequent irritation, or both using composition(s) herein compared to compositions comprising one or more non-ionic polyoxyethylene-polyoxypropylene block copolymers. In aspects, compositions provided by the invention provide detectably or significantly less irritation (e.g., the level of irritation reported by a user is detectably or significantly less), less frequent irritation, or both using composition(s) herein compared to similar compositions comprising one or more non-ionic polyoxyethylene-polyoxypropylene block copolymers wherein the non-ionic polyoxyethylene-polyoxypropylene block copolymer has the chemical structure HO—(CH2-CH2-O)x-(C3H6-O)y-(CH2-CH2-O)x-H, wherein x is an integer having the value of at least 8 and y is an integer having the value of at least 38 as the suspension agent.

Viscosity

In aspects, compositions provided by the invention have a viscosity suitable for via injection, such as, e.g., via intracameral injection. In aspects, compositions comprise viscosity and suspension characteristics such that the composition can be effectively administered through a needle having a gauge size of about 25 or higher, such as a needle having a gauge size of ~26, ~27, ~28, ~29, ~30, ~31, ~32, ~33, or, e.g. ~34. In aspects, compositions herein can be administered without failure (such as, e.g., by clogging of the needle due to particulate agglomeration) at least 90%, ≥~92%, ≥~94%, ≥~96%, ≥~98%, ≥~99%, or, e.g., even 100% of the time through a needle having a gauge size of 27. In aspects, compositions herein can be administered without failure (such as, e.g., by clogging of the needle due to particulate agglomeration) at least 90%, ≥~92%, ≥~94%, ≥~96%, ≥~98%, ≥~99%, or, e.g., even 100% of the time without failure through a needle having a gauge size of 28. In aspects, compositions herein can be administered without failure (such as, e.g., by clogging of the needle due to particulate agglomeration) at least 90%, ≥~92%, ≥~94%, ≥~96%, ≥~98%, ≥~99%, or, e.g., even 100% of the time through a needle having a gauge size of 29. In aspects, administration of the compositions comprises shaking the compositions prior to use, such as, e.g., shaking by hand for at least about 5 seconds, such as, at least ~6, ~7, ~8, ~9, or, e.g., ~10 seconds. In aspects, any significant flocculation which has occurred during shipping, storage, or at any period after manufacturing and prior to administration is resolved, and compositions can be administered without failure (such as, e.g., by clogging of the needle due to particulate agglomeration) at least 90%, ≥~92%, ≥~94%, ≥~96%, ≥~98%, ≥~99%, or, e.g., even 100% of the time through a needle having a gauge size of 27, 28, or 29.

In aspects, compositions provided by the invention have a viscosity which DOS negatively impact the intraocular pressure of the eye upon administration by injection, such as, e.g., composition(s) do not have a viscosity which, when administered by injection into aqueous humor or intravitreal injection, DOS increases the intraocular pressure such that a negative side effect of intraocular pressure increase manifests, such as, e.g., headache, eye pain, nausea, vomiting, blurred vision, halo formation around lights, eye redness, etc.

In aspects, compositions have a viscosity of from about 1-30 mPas, such as, e.g., between ~1.2-~30, mPas, ~1.4-~30, mPas, ~1.6-~30, mPas, ~1.8-~30, mPas, ~2-~30, mPas, ~2.2-~30, mPas, ~2.4-~30, mPas, ~2.6-~30, mPas, ~2.8-~30, mPas, ~3-~30, mPas, ~3.2-~30, mPas, ~3.4-~30, mPas, or, e.g., ~3.6-~30, mPas, such as, e.g., ~1-~28.5 mPas, ~1-~28 mPas, ~1-~27.5 mPas, ~1-~27 mPas, ~1-~26.5 mPas, ~1-~26 mPas, ~1-~25.5 mPas, ~1-~25 mPas, or, e.g., ~1-~24.5 mPas, as in, e.g., ~1.5 to ~28.5 mPas, ~2-~27.5 mPas, ~2.5-~26.5 mPas, ~3-~25.5 mPas, ~3.5-~25 mPas, or, e.g., about 3.7-24.2 mPas.

pH

In aspects, compositions provided by the invention have a pH within a range of between about 5-about 9, such as, e.g., between ~5-~9.4, ~5-~9.3, ~5-~9.2, ~5-~9.1, ~5-~9, ~5-~8.9, ~5-~8.8, ~5-~5-~8.6, or, e.g., ~5-~8.5, or, e.g., ~5.1-~9.5, or ~5.2-~9.5, ~5.4-~9.5, ~5.5-~9.5, ~5.6-~9.5, ~5.7-~9.5, ~5.8-~9.5, ~5.9-~9.5, ~6-~9.5, —6.1-~9.5, ~6.2-~9.5, ~6.3-~9.5, ~6.4-~9.5, or, e.g., ~6.5-~9.5, such as, e.g., ~5.7-~9.2, —6-~8.9, ~6.1-~8.8, ~6.2-~8.7, ~6.3-~8.6, ~6.4-~8.6, or, e.g., ~6.5-~8.5, such as between about 6.6-about 8.2, ~6.7-~8, ~6.8-~7.8, ~6.8-~7.6, ~6.8-~7.4, ~6.8-~7.2, or, e.g., about 7. In aspects, compositions provided by the invention are capable of maintaining a pH of between about 6.5-8.5 over the course of a period of at least about 2 months, ≥~3 months, ≥~4 months, ≥~5 months, ≥~6 months, ≥~7 months, ≥~8 months, ≥~9 months, ≥~10 months, ≥~11 months, ≥~12 months, ≥~18 months, or, e.g., ≥~24 months after manufacturing (e.g., while in shelf storage under directed conditions, prior to use, or, e.g., while stored at about 25° C. and about 40% relative humidity, about 40° C. and no more than about 25% relative humidity, or both (ophthalmic product), or, e.g., 25° C. and 60% relative humidity or at 40° C. and 75% relative humidity for 3 months (injectable product)).

Osmolality

In aspects, compositions provided by the invention have an osmolality of between about 150-400 mOsm/Kg, such as, e.g., 160-~400 mOsm/Kg, 170-~400 mOsm/Kg, 180-~400 mOsm/Kg, 190-~400 mOsm/Kg, 200-~400 mOsm/Kg, such as, e.g., ~150-~390 mOsm/Kg, ~150-~380 mOsm/Kg, ~150-~360 mOsm/Kg, or, e.g., ~150-~350 mOsm/Kg, as in between ~210-~380 mOsm/Kg, ~220-~360 mOsm/Kg, ~230-~340 mOsm/Kg, ~240-~320 mOsm/Kg, ~250-~310 mOsm/Kg, ~260-~300 mOsm/Kg, ~270-~290 mOsm/Kg, or, e.g., between ~280-~290 mOsm/Kg.

Stability

Compositions of the invention can be, in aspects, characterized on the basis of physical stability, chemical stability, or both. In aspects, compositions exhibit sufficient physical and chemical integrity to maintain at least ~98% of the amount of any included API(s) and to maintain total impurities below 0.5% (e.g., below pharmaceutically acceptable level) to allow storage at a convenient temperature, such as between about 2° C. and about 50° C., for a commercially reasonable period of time, such as, e.g., at least about 1 month, such as at least about 2 months, or at least about 3 months or more, e.g. typically for at least about 4, ~5, ~6, ~7, —8, ~9, ~10, ~11, ~12, ~18, ~24, ~30, or, e.g., ~36 months, when stored in its original packaging. The term "physical stability" typically refers to maintenance of color, dissolved oxygen level, head space oxygen level, particulate matter, etc. Relevant to suspensions, physical stability can refer to no DOS increase in coagulation, flocculation, caking, clumping, etc. In aspects, physical stability for suspensions means no DOS flocculation, coagulation, or clumping, etc., or at least no sustained flocculation, coagulation, clumping, etc. (e.g., flocculation, coagulation, clumping, etc., that is not reduced to below visual detection levels upon routine agitation such as about 0.5-5, 0.3-3, 0.25-2, 0.25-1.5, 0.25-1, 0.5-1, or 0.25-2.5 minutes of manual shaking). Related aspects are described elsewhere herein. The term "chemical stability" typically refers to formation of drug-related impurities in terms of total impurity, single maximum individual impurity, and maximum individual unknown impurity, or to the reduction in API due to undesired reactions. For the purpose of the compositions provided by the invention described here. In aspects, chemical stability also includes maintenance of pH of the finished formulation.

The terms "impurity" or "impurities" refer to undesired substance(s) in a composition which may be present in a composition immediately following manufacturing (e.g., at initial quality control testing composition following manufacturing, prior to storage) or which may be formed after a certain period of shelf life of a composition. Impurities may be formed via degradation of one or more components of the composition. Sources of degradation can include, e.g., oxidation, light, ultraviolet light, moisture, heat, changes in pH, and composition component interactions.

In aspects, compositions provided by the invention are stable compositions such that quinolone antibiotic component constituent(s) of the compositions, the anti-inflammatory steroid component constituents(s) of the compositions, or both the quinolone antibiotic and anti-inflammatory API(s) are present in an amount of at least 98%, such as ≥~98.2%, ≥~98.4%, ≥~98.6%, ≥~98.8%, ≥~99%, ≥~99.2%, ≥~99.4%, ≥~99.6%, ≥~99.8%, or even ~100% for a period of at least about 1 month (e.g., ~2, ~3, ~4, ~5, ~6 months or more such as ≥12, ≥18, or ≥24 months) when stored at relevant conditions, such as, e.g., at about 25° C. and about 40% relative humidity, at about 40° C. and not more than 25% relative humidity, or both (e.g., for an ophthalmic topical/drop product), or, e.g., 25° C. and 60% relative humidity or at 40° C. and 75% relative humidity for 3 months (e.g., for an ophthalmological injectable product).

In aspects, compositions provided by the invention are capable of maintaining a level of total impurities of less than about 0.5%, such as less than ~0.4%, <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months or more when stored at relevant conditions, such as FDA stability testing conditions, such as, e.g., at about 25° C. and about 40% relative humidity, at about 40° C. and not more than 25% relative humidity, or both (e.g., for an ophthalmic applied product, such as an eye drop product), or, e.g., 25° C. and 60% relative humidity or at 40° C. and 75% relative humidity for 3 months (for an injectable product).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of any quinolone antibiotic component, one or more quinolone antibiotic component constituents, e.g., an antibacterial compound constituent, any anti-inflammatory steroid component, one or more anti-inflammatory steroid component constituents, any combination of any or all thereof including all of such ingredients for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more (under relevant conditions, such as those described above or elsewhere herein).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of the labeled concentration of moxifloxacin for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more under storage conditions provided by the label (e.g., under typical storage conditions).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of the labeled concentration of gatifloxacin for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more under storage conditions provided by the label (e.g., under typical storage conditions).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of the labeled concentration of triamcinolone acetonide for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more under storage conditions provided by the label (e.g., under typical storage conditions).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of the labeled concentration of loteprednol etabonate for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more under storage conditions provided by the label (e.g., under typical storage conditions).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of the labeled concentration of prednisolone acetate for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more under storage conditions provided by the label (e.g., under typical storage conditions).

In aspects, compositions herein retain at least about 85 w/w. % of the potency, e.g., ≥~85 w/w. %, ≥~85 w/w. %, ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of the labeled concentration of bromfenac for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more under storage conditions provided by the label (e.g., under typical storage conditions).

In aspects, the characterization of "stable" can be used to describe the ability of compositions to effectively maintain both a quinolone antibiotic component and an anti-inflammatory steroid component in suspension, such that the consistency of the composition is at least generally, substantially, or effectively uniform, e.g., at least about 90%, e.g., ≥~91%, ≥~92%, ≥~93%, ≥~94%, ≥~95%, ≥~96%, ≥~97%, ≥~98%, ≥~99%, or, e.g., even about 100% of the composition has a relative ratio of any single component to any other single component of no more than 1.1:1, such as no more than ~1.09:1, 1.08:1, 1.07:1, 1.06:1, 1.05:1, 1.04:1, 1.03:1, 1.02:1, 1.01:1 or, e.g., about 1:1.

In aspects, compositions of the invention can be characterized on the basis of having uniformity, maintaining uniformity over time, or both. In general, composition uniformity can be described by a uniformity of content equation:

$$\text{Uniformity of content} = \frac{\text{Detected content}}{\text{Theoretical content}} \times 100$$

In the provided equation, "detected content" is the amount or concentration of compound detected in a sample; "theoretical content" is the amount or concentration of compound which should be present in a completely uniform composition. In aspects, when at least 10 samples of a well-mixed (e.g., well-shaken, such as, e.g., shaken by hand for at least about 5 seconds) are tested for any given active ingredient (e.g., a fluoroquinolone antibiotic compound, a steroid anti-inflammatory compound, or, e.g., a non-steroid anti-inflammatory compound) at least 90% of all samples result in a uniformity of content between 85%-115%. In aspects, when at least about 90%, ~92%, ~94%, ~96%, ~98%, or more samples tested have a uniformity of content between about 90% and 120%, 90% and 115%, or, e.g., between about 90% and 110%.

In aspects, conducting the above content uniformity analysis on 10 or more samples each having been stored for, e.g., 1 month (e.g. ~2, ~3, ~4, ~5, ~6 months or more such as ≥12, ≥18, or ≥24 months) when at about 25° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product) results in at least about 90% of such samples having a content uniformity meeting USP acceptability criteria for ophthalmic suspensions.

In aspects, when 10 or more samples, such as, e.g., ≥~12, ≥~14, ≥~16, ≥~18, or, e.g., ≥~20 or more samples of a single manufactured batch of ophthalmic composition are tested using the above method, at least about 85%, ~90%, ~95%, or more, such as 100% of samples have a content uniformity meeting USP acceptability criterion for ophthalmic suspensions. In aspects, when ~3, ~4, ~5, ~6, ~7, ~8, ~9, or, e.g. ~10 or more samples, such as, e.g., ≥~12, ≥~14, ≥~16, ≥~18, or, e.g., ≥~20 or more doses of a treatment regimen of ophthalmic composition are tested using the above method, at least about 85%, ~90%, ~95%, or more, such as 100% of such samples have a content uniformity meeting USP acceptability criteria for ophthalmic suspensions.

In aspects, content uniformity can be described by comparing the amount of any given active ingredient received in one dose with the amount of the same active ingredient received in any subsequent dose. In aspects, across a treatment period (of, e.g., about 1 day, ~2 days, ~3 days, ~4, days, ~5 days, ~6 days, ~7 days, ~8 days, ~9 days, or, e.g., ~10 days), the amount of any given active ingredient received in one dose is not less than 85% of, and not more than 120% more than, the amount of the same active ingredient received in any other dose of the treatment period.

Route of Administration

In aspects, the invention provides compositions which are administered by injection. In aspects, compositions provided by the invention are administered by intracameral injection. In aspects, the invention provides compositions which are administered topically, such as, e.g., as drops. In aspects, compositions are provided in ready-to-use form, such as, e.g., prepackaged in injection device(s) or prepackaged in dropper bottle(s) as is described elsewhere herein.

Method of Making/Manufacturing Compositions

In aspects, the invention provides methods of manufacturing a composition described herein. In aspects, the invention provides methods of manufacturing a composition comprising ophthalmologically suitable amounts of (1) one or more quinolone antibiotic components (e.g., one or more antibacterial compounds), (2) one or more anti-inflammatory steroid components (e.g., one or more steroid compounds such as a corticosteroid compounds, one or more non-steroid compounds, or a combination thereof), (3) one or more suspension agents (such as, e.g., hyaluronic acid), and optionally (4) one or more excipients or additional APIs, such as, e.g., an effective amount of chelating agent(s) such as an EDTA compound, an effective amount of surfactant(s), an effective amount of viscoelasticity agent(s), an effective amount of preservative(s), buffer(s), emulsifier(s), or sequestration agent(s), including any derivative thereof, or combination of any or all thereof). In aspects, such a composition has pH of between about 6.5-about 8.5, is stable for at least 1 month when stored at ~25° C. and ~40% relative humidity or at about 40° C. and no more than about 25% relative humidity (ophthalmic product), or, e.g., 25° C. and 60% relative humidity or at 40° C. and 75% relative humidity for 3 months (injectable product), and maintains a total level of impurities of less than ~0.5% for a period of at least about 1 month (e.g., ≥3, ≥6, ≥12, ≥18, or ≥24 months) when stored at about 25° C. and about 40% relative humidity, at about 40° C. and not more than 25% relative humidity, or both (ophthalmic product) or 25° C. and 60% relative humidity or at 40° C. and 75% relative humidity for 3 months (injectable product).

In aspects, compositions provided by the invention are prepared (e.g., are manufactured) according to any suitable technique, many of which are known to those skilled in the art. In aspects, steps of a method of manufacturing can be performed in different orders.

In exemplary aspects, the manufacturing of compositions can be broken down into 3 main parts. Part I involves forming a solution of the anti-inflammatory steroid component, Part II involves forming a solution of all other ingredients, and Part III involves combining Parts I and II into a final solution.

Part I.

In aspects, the method of manufacturing comprises adding the total quantity of anti-inflammatory agent and, in a suitable container, to total a volume of water (e.g., water for injection (WFI) which is less than the ultimate final total volume of the composition batch, such as, e.g., a total volume representing about 20, ~25%, ~30%, ~35%, or ~40% of the total volume. In aspects, a suspension is created. In aspects, the anti-inflammatory agent is, e.g., triamcinolone, prednisolone, or, e.g., loteprednol.

In such aspects, the suspension is treated to form a suspension wherein particles of the suspension have a targeted particle size. In aspects, the suspension is treated by any method known in the art for forming particular particle sizes, such as homogenization. In aspects, the suspension is then passed through a homogenizer. In aspects, the resulting suspension, after homogenization, comprises particles having a $D_{50}$ of greater than about 0.25 µm but less than about 3.75 µm, such as between ~0.25-~3.5 µm, ~0.25-~3.25 µm, ~0.25-~3 µm, ~0.25-~2.75 µm, ~0.25-~2.5 µm, ~0.25-~2 µm, ~0.25-~1.75 µm, or, e.g., ~0.25-~1.5 µm, such as, e.g., ~0.5-~3.75, ~0.75-~3.75 µm, ~1-~3.75 µm, ~1.25-~3.75 µm, ~1.5-~3.75 µm, ~1.75-~3.75 µm, or, e.g., between ~2-~3.75 µm, such as, e.g., between about 0.5-1.5 µm, ~2-~3 µm, or, e.g., between ~0.5-3 µm.

In such aspects, upon completion of homogenization, the composition is sterilized. In aspects, any sterilization method known in the art can be used for sterilizing the suspension. In aspects, the suspension is sterilized using an autoclave. In aspects, the suspension is autoclaved at between about 115° C.-135° C. for up to 1 hour. For example, the suspension is autoclaved at 121° C. for about 20-about 40 minutes, such as, e.g., ~25 minutes, ~30 minutes, ~35 minutes, or, e.g., ~40 minutes. In aspects, the suspension is autoclaved for a sufficient amount of time and at a sufficient temperature to sterilize the composition by thermal lethalization without negatively impacting any one or more ingredients, such as e.g., causing DOS degradation of any one or more ingredients including a reduction in a DOS amount of any one or more ingredients or a DOS in an amount of activity which an ingredient can impart either to the composition or therapeutically upon administration. In aspects, the sterilization step detectably or significantly reduces the amount(s) of related compound(s) and impurities associated with the ophthalmic composition upon storage of the composition at about 25° C. and about 40% relative humidity, at about 40° C. and not more than 25% relative humidity (ophthalmic product), or, e.g., 25° C. and 60% relative humidity or at 40° C. and 75% relative humidity for 3 months (injectable product), or both for a period of at least about 1 month, e.g., at least ~2, ~3, ~4, ~5, or, e.g., ~6 months or more (e.g., ≥12, ≥18, or ≥~24 months).

In such aspects, after autoclaving, the suspension is stirred while allowed to cool to about room temperature (e.g., about 25° C.±2° C.). This suspension is referred to as "Part I." The performance of such steps also can be referred to as Part I.

Part II

In aspects, a separate volume of water, e.g., WFI, is collected for preparing the quinolone antibiotic component of the composition which comprises one or more additional ingredients, including the suspension component. In aspects, the separate volume represents less than all of the remaining total volume of the composition, such as a volume which represents between about 45-60% of the total volume of the composition, such as, e.g., ~40%, ~45%, ~50%, ~55%, or, e.g., about 60% of the total composition volume. In aspects, one or more ingredients representing a preservative, buffer, emulsifier, or sequestering agent, e.g., sodium citrate monohydrate, is completely dissolved in the water.

In aspects, upon complete dissolution of the preservative, buffer, emulsifier, or sequestering agent (e.g., sodium citrate monohydrate) ingredient(s), surfactant ingredient(s) (e.g., polysorbate-80) are completely dissolved in the same solution.

In aspects, upon complete dissolution of the surfactant ingredient(s), e.g., polysorbate-80, chelating agent(s) (e.g., disodium edetate dihydrate) are added to the same solution and completely dissolved. In aspects, upon complete dissolution of the chelating agent(s), e.g., disodium edetate dihydrate), a preservative agent(s) (e.g., benzalkonium chloride) is added. In aspects, preservative agent(s) are added later.

At this stage of Part II, steps can vary, depending on the ingredients used in a particular formulation.

In aspects, the suspension component is added at this stage, followed by the addition of viscoelasticity agent(s), at which time the resulting solution is sterilized, e.g., by autoclaving, and, following, sterilization the quinolone antibiotic component is added, with or followed by the addition of a preservative agent, the solution is brought to a volume by QS, the pH is adjusted, and the suspension of Part I and the solution of Part II of the process are combined. Here, this process is referred to as Part IIA.

In aspects, the quinolone antibiotic component is added at this stage, followed by the addition of the suspension component, at which time the resulting solution is pH adjusted, the solution is brought to a volume by QS, and the suspension of Part I and the solution of part II of the process are combined. Here, this process is referred to as Part IIB.

In aspects, the quinolone antibiotic component is added at this stage, followed by the addition of the suspension component, optionally followed by the addition of a viscoelasticity agent(s), whereafter the resulting solution is pH adjusted, brought to volume by QS, and the suspension of Part I and the solution of part II of the process are combined. Herein, this process is referred to as Part JIG.

Part IIA

In aspects, upon formation of a completely dissolved solution of the preservative, buffer, emulsifier, or sequestering agent ingredient(s), surfactant ingredient(s), and chelating agent(s), the total quantity of the suspension component(s) (e.g., hyaluronic acid) is added. In certain aspects, the suspension component(s) are added after the addition of the quinolone antibiotic component(s). In aspects, upon addition, the mixture is stirred or otherwise agitated (e.g., stirred at moderate speed) until the suspension agent(s) is completely dissolved, such as for a period of about 15 minutes, ~30 minutes, ~45 minutes, ~1 hour, ~1.25 hours, ~1.5 hours, ~1.75 hours, ~2 hours, ~2.25 hours, ~2.5 hours, ~2.75 hours, or, e.g., about 3 hours or more. In aspects, a completely dissolved solution is formed within 2 hours.

In aspects, upon the complete dissolution of the suspension component (e.g., hyaluronic acid), viscoelasticity agent(s), e.g., chondroitin sulfate, is added and allowed to completely dissolve. In aspects, this step is absent.

In aspects, the resulting solution is sterilized using an autoclave. In aspects, the suspension is autoclaved at between about 115° C.-135° C. for up to 1 hour. For example, the suspension is autoclaved at 121° C. for about 20-about 40 minutes, such as, e.g., ~25 minutes, ~30 minutes, ~35 minutes, or, e.g., ~40 minutes. In aspects, the suspension is autoclaved for a sufficient amount of time and at a sufficient temperature to sterilize the composition by thermal lethalization without negatively impacting any one or more ingredients, such as e.g., causing DOS degradation of any one or more ingredients including a reduction in a DOS amount of any one or more ingredients or a DOS in an amount of activity which an ingredient can impart either to the composition or therapeutically upon administration. In aspects, the sterilization step detectably or significantly reduces the amount(s) of related compound(s) and impurities associated with the ophthalmic composition upon storage of the composition at about 25° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product), for a period of at least about 1 month, e.g., at least ~2, ~3, ~4, ~5, or, e.g., ~6 months or more (e.g., ≥12, ≥18, or ≥~24 months).

In aspects, upon completion of sterilization, e.g., autoclaving, the solution is allowed to cool to about room temperature (e.g., about 25° C.±2° C.).

In aspects, upon reaching about room temperature after autoclaving, the total quantity of quinolone antibiotic component is added. In aspects, the total quantity of quinolone antibiotic component is allowed to completely dissolve, e.g., by stirring.

In aspects, upon reaching about room temperature after autoclaving, the total quantity of quinolone antibiotic component is added in addition to one or more preservative ingredients, e.g., benzalkonium chloride, both of which are allowed to completely dissolve, e.g., by stirring.

In aspects, the completely dissolved solution is brought to a final volume of (e.g., is "QSd" to a final volume) representing between about 50-about 80% of the final total volume of the composition batch, such as, e.g., to a final volume representing about ~50%, ~52%, ~54%, ~56%, ~58%, ~60%, ~62%, ~64%, ~66%, ~68%, ~70%, ~72%, ~74%, ~76%, ~78%, or, e.g., ~80%, of the total volume of the composition batch. In aspects, the solution is QS to about 65% of the final total volume.

In aspects, the pH of the solution is adjusted to between about 6.5-about 8.5, such as, e.g., to ~6.6, ~6.7, ~6.8, ~6.9, ~7, ~7.1, ~7.2, ~7.3, ~7.4, ~7.5, ~7.6, ~7.7, ~7.8, ~7.9, —8, ~8.1, ~8.2, ~8.3, ~8.4, or, e.g., ~8.5, such as, e.g., to about 7.0±0.2 using pH adjusting agents. In aspects, any appropriate pH adjusting agent is used. In aspects, the pH adjusting agent is hydrochloric acid or sodium hydroxide.

In aspects, the Part HA composition (above) is then sterile filtered using a filter no bigger than 0.2 μm, e.g., using a 0.2 μm filter, into the Part I composition (above) (Part III). In aspects, the sterilization step detectably or significantly reduces the amount(s) of related compound(s) and impurities associated with the ophthalmic composition upon storage of the composition at about 25° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product), for a period of at least about 1 month, e.g., at least ~2, ~3, ~4, ~5, or, e.g., ~6 months or more (e.g., ≥12, ≥18, or ≥~24 months).

An amount of water representing part or all of the remaining total volume of the solution is used to rinse the container of Part HA and is then passed through the same sterilizing filter as the previous step.

The final product is then QS to the final total batch volume by sterile filtered water (WFI) as needed.

Part IIB

In aspects, upon formation of a completely dissolved solution of the preservative, buffer, emulsifier, or sequestering agent ingredient(s), surfactant ingredient(s), and chelating agent(s), the total amount of quinolone antibiotic component is added to the solution and allowed to completely dissolve.

In aspects, following the complete dissolution of the antimicrobial agent, the total quantity of the suspension agent(s), e.g., PEG 3350 or CMC, is added. In aspects, upon addition, the mixture is stirred or otherwise agitated (e.g., stirred at moderate speed) until the suspension agent(s) is completely dissolved, such as for a period of about 15 minutes, ~30 minutes, ~45 minutes, ~1 hour, ~1.25 hours, ~1.5 hours, ~1.75 hours, ~2 hours, ~2.25 hours, ~2.5 hours, ~2.75 hours, or, e.g., about 3 hours or more. In aspects, a completely dissolved solution is formed within 2 hours.

In aspects, the pH of the solution is adjusted to between about 6.5-about 8.5, such as, e.g., to ~6.6, ~6.7, ~6.8, ~6.9, ~7, ~7.1, ~7.2, ~7.3, ~7.4, ~7.5, ~7.6, ~7.7, ~7.8, ~7.9, —8, ~8.1, ~8.2, ~8.3, ~8.4, or, e.g., ~8.5, such as, e.g., to about 7.0±0.2 using pH adjusting agents. In aspects, any appropriate pH adjusting agent is used. In aspects, the pH adjusting agent is hydrochloric acid or sodium hydroxide.

In aspects, the completely dissolved solution is brought to a final volume of (e.g., is "QSd" to a final volume) representing between about 50-about 80% of the final total volume of the composition batch, such as, e.g., to a final volume representing about ~50%, ~52%, ~54%, ~56%, ~58%, ~60%, ~62%, ~64%, ~66%, ~68%, ~70%, ~72%, ~74%, ~76%, ~78%, or, e.g., ~80%, of the total volume of the composition batch. In aspects, the solution is QS to about 65% of the final total volume.

In aspects, Part IIB (above) is then sterile filtered using a filter no bigger than 0.2 µm, e.g., using a 0.2 µm filter, into Part I (above) (Part III). In aspects, the sterilization step detectably or significantly reduces the amount(s) of related compound(s) and impurities associated with the ophthalmic composition upon storage of the composition at about 25° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product), for a period of at least about 1 month, e.g., at least ~2, ~3, ~4, ~5, or, e.g., ~6 months or more (e.g., >12, >18, or ≥~24 months).

An amount of water representing part or all of the remaining total volume of the solution is used to rinse the container of Part JIB and is then passed through the same sterilizing filter as the previous step.

The final product is then QS to the final total batch volume by sterile filtered water (WFI) as needed.

The manufacturing process for various formulations is further exemplified in the Examples section herein.

In aspects, the resulting compositions are used to fill final product containers, e.g., vials, dropper bottles, and the like, in preparation for shipment, storage, or final use. In aspects, final product containers are containers accessible by a needle, such that a needle can be used to extract compositions from the container for use in intracameral injection techniques, such containers and such withdrawal techniques being known in the art.

Part IIC

In aspects, upon formation of a completely dissolved solution of the preservative, buffer, emulsifier, or sequestering agent ingredient(s), surfactant ingredient(s), and chelating agent(s), and, optionally, preservative(s), the total amount of quinolone antibiotic component is added to the solution and allowed to completely dissolve.

In aspects, following the complete dissolution of the antimicrobial agent, the total quantity of the suspension component, e.g., PEG 3350, CMC, or HA is added. In aspects, upon addition, the mixture is stirred or otherwise agitated (e.g., stirred at moderate speed) until the suspension agent(s) is completely dissolved, such as for a period of about 15 minutes, ~30 minutes, ~45 minutes, ~1 hour, ~1.25 hours, ~1.5 hours, ~1.75 hours, ~2 hours, ~2.25 hours, ~2.5 hours, ~2.75 hours, or, e.g., about 3 hours or more. In aspects, a completely dissolved solution is formed within 2 hours.

In aspects, upon dissolution of the suspension component, a viscoelasticity agent, e.g., chondroitin sulfate, is added and allowed to completely dissolve.

In aspects, the pH of the solution is adjusted to between about 6.5-about 8.5, such as, e.g., to ~6.6, ~6.7, ~6.8, ~6.9, ~7, ~7.1, ~7.2, ~7.3, ~7.4, ~7.5, ~7.6, ~7.7, ~7.8, ~7.9, —8, ~8.1, ~8.2, ~8.3, ~8.4, or, e.g., ~8.5, such as, e.g., to about 7.0±0.2 using pH adjusting agents. In aspects, any appropriate pH adjusting agent is used. In aspects, the pH adjusting agent is hydrochloric acid or sodium hydroxide.

In aspects, the completely dissolved solution is brought to a final volume of (e.g., is "QSd" to a final volume representing between about 50-about 80% of the final total volume of the composition batch, such as, e.g., to a final volume representing about ~50%, ~52%, ~54%, ~56%, ~58%, ~60%, ~62%, ~64%, ~66%, ~68%, ~70%, ~72%, ~74%, ~76%, ~78%, or, e.g., ~80%, of the total volume of the composition batch. In aspects, the solution is QS to about 65% of the final total volume.

In aspects, the composition of Part IIC (above) is then sterile filtered using a filter no bigger than 0.2 µm, e.g., using a 0.2 µm filter, into Part I (above) (Part III). In aspects, the sterilization step detectably or significantly reduces the amount(s) of related compound(s) and impurities associated with the ophthalmic composition upon storage of the composition at about 25° C. and about 40% relative humidity, at about 40° C. and not more than 25% relative humidity, or both (ophthalmic product), or, e.g., 25° C. and 60% relative humidity or at 40° C. and 75% relative humidity for 3 months (injectable product), for a period of at least about 1 month, e.g., at least ~2, ~3, ~4, ~5, or, e.g., ~6 months or more (e.g., >12, >18, or ≥~24 months).

An amount of water representing part or all of the remaining total volume of the solution is used to rinse the container of Part IIC and is then passed through the same sterilizing filter as the previous step.

The final product is then QS to the final total batch volume by sterile filtered water (WFI) as needed.

The manufacturing process for various formulations is further exemplified in the Examples section herein.

In aspects, the resulting compositions are used to fill final product containers, e.g., vials, dropper bottles, and the like, in preparation for shipment, storage, or final use.

Product by Process Aspects

According to aspects, the invention provides an ophthalmologically suitable composition such as any one or more of the compositions described in this disclosure, wherein the composition is made by any process of manufacturing described herein or any suitable combination of step(s) described in connection with such methods. The properties of such compositions imparted by such steps can comprise the characteristics described above in connection with characteristics of compositions, such as physical stability of the composition.

Packaging

According to certain embodiments, ophthalmologically suitable compositions of the invention can be packaged in any suitable packaging, such suitability being at least in part defined by protecting the compositions held therein from degradation, contamination, or both. In certain aspects, suitable packaging materials are materials which exhibit less than about 20%, such as <~18%, <~16%, <~14%, <~12%, <~10%, <~8%, <~6%, <~4%, <~2% or even less sorption of an antibiotic component constituent, such as, e.g., a quinolone antibiotic, or more specifically a fluoroquinolone antibiotic, such as, e.g., moxifloxacin or gatifloxacin, or an anti-inflammatory steroid component constituent, such as, e.g., a steroid or non-steroid anti-inflammatory compound. In some respects, suitable materials include but may not be limited to packaging material made of select polyolefins, such as, e.g., DuPont® 20 LDPE, Chevron 5502 HDPE, Atofina 3020 PP, polypropylene homopolymers, low ethylene content (<8%) polypropylenes, and polymers (HDPE, PP) with low content of additives (<5%) and with low flexural modulus (<200 kpsi). In some respects, a suitable material is an EP-quality LDPE which, in further aspects, may contain no additives. In aspects, suitable packaging can comprise a polypropylene container provided that that polypropylene container is not packaged in a bag/container containing an iron oxide oxygen scavenger.

In certain aspects, the packaging can comprise or can be mostly comprised of (e.g., comprise in an amount ≥~10%, ≥~20%, ≥~30%, ≥~40%, or ≥~50%, such as, e.g., comprise in an amount ≥~60%, ≥~70%, ≥~80%, ≥~90% or more) an ultraviolet-light blocking agent or material. In aspects, such a material can be capable of blocking ≥~1%, ≥~5%, ≥~10%, ≥~20%, ≥~30%, ≥~40%, or ≥~50%, such as, e.g., ≥~60%, ≥~70%, ≥~80%, ≥~90% or more of the ultraviolet light in the environment from entering the container. In aspects, compositions described herein can be packaged in, stored, in, or both packaged and stored in a container wherein the container significantly reduces exposure of the composition to UV B radiation, such as by at least about 50%, at least about 65%, at least about 75%, at least about 90%, at least about 95%, or at least 99%. In some aspect the packaging material of a composition described herein is semi- or completely opaque, while in alternative aspects, the packaging is semi- or completely clear. In aspects, packaging can comprise different parts wherein one component of the packaging comprises a first material and one or more components of the packaging contain a second (or more) material(s).

In certain aspects, packaging can be selected based on the method of delivery of the compositions herein (e.g., compositions provided as a cream can be provided in suitable packaging for creams wherein compositions provided as a liquid can be provided in suitable packaging for liquids, e.g., in a user-friendly dropper bottle.) In aspects, the compositions provided by the invention are stored in vials capable of being penetrated by a needle such that compositions can be extracted from such vials and administered by injection. In aspects, compositions are provided in pre-filled injection devices, such as, e.g., pre-filled syringes. In aspects, the compositions of the invention are stored in a packaging that facilitates the delivery of the composition as eye drops.

In one aspect, the ophthalmic compositions comprise antimicrobial compounds, such as, e.g., quinolone antibiotics, e.g., specifically fluoroquinolone antibiotics such as, e.g., moxifloxacin or gatifloxacin, anti-inflammatory compound(s), such as, e.g., corticosteroid or non-steroid compounds, and one or more pharmaceutically acceptable excipient(s), and are provided in single-dose bottles. In an alternative aspect, such compositions are provided in multi-dose bottles, such as multi-dose eye dropper bottles. In aspects, such multi-dose bottles allow for the composition, e.g., provided as a solution to be dropped into the recipient's eye(s), to be applied as liquid drops over a course of treatment, such as, e.g., over the course of many days, several weeks, or longer.

In aspects, the average force required to release one or more drops of the compositions described herein from a dropper bottle (a standard bottle common in the art for dispensing liquid in droplet form), by compressing the middle section of the storage body of such a dropper bottle, ranges between about 1.7-2.8 kg for release of the first drop, e.g., between about 1.7-2.6, ~1.7-2.4, ~1.7-2.2, or between about ~1.7-2.0. In aspects, successive drops can require more tension, such as can require an additional ~20-30% of force for release of the second drop, and, e.g., an additional force of ~24-50% for release of the third drop.

In some aspects, compositions provided by the invention are administered by intracameral injection. In aspects, compositions are provided in packaging which is accessible via a needle such that compositions can be withdrawn by a needle in preparation for intracameral injection. In aspects, compositions are provided in pre-filled injection devices, such as pre-filled syringes. In aspects, one or more pre-filled syringes are provided in a kit as is described further elsewhere herein. In aspects, injection devices can comprise between about 0.25 mL-about 5 mL of composition, though typically up to about 1 mL, such as, e.g., between ~0.5-~5 mL, ~0.75-~5 mL, ~1-~5 mL, ~1.25-~5 mL, ~1.5-~5 mL, ~1.75-~5 mL, ~2-~5 mL, ~2.25-~5 mL, ~2.5-~5 mL, ~2.75-~5 mL, ~3-~5 mL, ~3.25-~5 mL, ~3.5-~5 mL, ~3.75-~5 mL, ~4-~5 mL, ~4.25-~5 mL, ~4.5-~5 mL, or, e.g. ~4.75-~5 mL, such as for example ~0.25-~4.5 mL, ~0.25-~4 mL, ~0.25-~3.5, ~0.25-~3.5 mL, ~0.25-~3 mL, ~0.25-~2.5 mL, ~0.25-~2 mL, ~0.25-~1.5 mL, or, e.g. ~0.25-~1 mL of composition, as in, e.g. ~0.1 mL, ~0.15 mL, ~0.2 mL, ~0.25 mL, ~0.3 mL, ~0.35 mL, ~0.4 mL, ~0.45 mL, ~0.5 mL, ~0.55 mL, ~0.6 mL, ~0.7 mL, ~0.75 mL, ~0.8 mL, ~0.85 mL, ~0.9 mL, or, e.g., ~1 mL.

In aspects, compositions provided by the invention are provided in single dose or multi-dose packaging.

In aspects, a single dose package comprises a single dose of composition within a single dose administration container. In aspects, a multi-dose package comprises a plurality of single dose administration containers. In aspects, a multi-dose package comprises a plurality of doses within a single administration container. For example, a multi-dose package can be, e.g., a single dropper bottle comprising sufficient volume of composition to administer the composition multiple times over the course of an administration period, such as (but certainly not limited to) administration of about 1-3x/day over a period of about 1-7 days.

In aspects, packaging of compositions is any suitable packaging which effectively provides compositions with a shelf life of at least about 1 month, such as, e.g., ≥~3 weeks, ≥~4 weeks (1 month), ≥~5 weeks, ≥~6 weeks, ≥~7 weeks, ≥~8 weeks (2 months), ≥~9 weeks, ≥~10 weeks, ≥~11 weeks, ≥~12 weeks (3 months), ≥~13 weeks, ≥~14 weeks, ≥~15 weeks, ≥~16 weeks (4 months), or more, such as ≥~5 months, ≥~6 months, ≥~7 months, ≥~8 months, ≥~9 months, ≥~10 months, ≥~11 months, or ≥~12 months (1 year), or even longer, such as, ≥~18 months, ≥~24 months (2 years), ≥~30 months, or, e.g., ≥~36 months (3 years) or longer.

Here, the term "shelf life" refers to the amount of time the composition is stored without loss of potency and/or loss of a suitable dissolution profile, such as, e.g., loss of suitable suspension of quinolone antibiotic component constituent(s), anti-inflammatory steroid component constituent(s), or both. In aspects, shelf life refers to the amount of time the compositions effectively maintain both a quinolone antibiotic component and an anti-inflammatory steroid component in suspension, such that the consistency of the composition is at least generally, substantially, or effectively uniform, e.g., at least about 90%, e.g., ≥~91%, ≥~92%, ≥~93%, ≥~94%, ≥~95%, ≥~96%, ≥~97%, ≥~98%, ≥~99%, or, e.g., even about 100% of the composition has a relative ratio of any single component to any other single component of no more than 1.1:1, such as no more than ~1.09:1, 1.08:1, 1.07:1, 1.06:1, 1.05:1, 1.04:1, 1.03:1, 1.02:1, 1.01:1 or, e.g., about 1:1. In aspects, shelf life refers to a period of time wherein neither the quinolone antibiotic component nor the anti-inflammatory steroid component lose more than about 10%, such as, e.g., ≤~9%, ≤~8%, ≤~7%, ≤~6%, ≤~5%, ≤~4%, ≤~3%, ≤~2%, or, e.g., ≤~1%, of the potency while in storage after manufacturing and prior to use.

"Kits" (Collections of Components)

In aspects, the invention provides kits comprising an ophthalmologically suitable composition according to any one or more of the compositions provided by aspects of the invention described herein, packaged in one or more containers, e.g., one or more single dose or multi-dose containers. In aspects, a kit comprises one or more delivery devices for administering the composition to a recipient. In aspects, kits comprise one or more container means, which can include containers described elsewhere (e.g., pharmaceutically acceptable vials) or known equivalents thereof.

In aspects, the invention provides a kit comprising a delivery device as described in this section, wherein any single use container comprising a composition present in the kit is accessible to the delivery device/system of the kit, such as, e.g., containing a stopper which effectively seals the single use container and effectively prevents contamination of the content therein prior to use but which is penetrable by the delivery device/system such that the delivery device can extract the composition from the single use container. In aspects, the invention provides the kit described above, wherein the delivery device is a syringe system, such as a syringe and an accompanying needle for use with the syringe. In aspects, a kit can comprise "delivery means" including such components or known equivalents of such components.

In aspects, the invention provides a kit wherein compositions are pre-filled in a delivery device, and a kit comprises one or more pre-filled delivery devices and one or more additional components to facilitate administration of the composition(s). For example, in aspects the invention provides a kit wherein compositions are pre-filled in a syringe and the kit comprises one or more needles to facilitate delivery of the compositions by injection, such as, e.g., for administration by intracameral injection. In aspects, the invention provides a composition which is formulated for injection and contained in an injection delivery device, a device adapted for injection delivery, or is packaged with an injection delivery device.

In aspects, the invention provides a kit wherein composition(s) are provided in one or more pre-filled containers which facilitate administration of the compositions by drops, such as, e.g., one or more pre-filled dropper bottles as described herein.

In aspects, the invention provides for a kit as described in this section, wherein the kit has a shelf life when stored at about room temperature, such as, e.g., about 25° C.+/−~2° C., for at least about 1 month, e.g., ~2, ~3, ~4, ~5, or at least about 6 months (e.g., 6-24 mos.).

Methods of Use

In aspects, the invention provides methods of using compositions disclosed here in the treatment or prevention of high-risk infection. Here, "high-risk infection" refers to an infection wherein a potentially dangerous number of bacteria is expected to be or is present in the eye or wherein the infective agent is expected to be capable of causing detectable or significant damage to the eye.

In aspects, compositions provided by the invention are administered in association with the performance of an invasive ophthalmic procedure, such as before or after an invasive ophthalmic procedure, such as an ophthalmic surgery.

In aspects the invention provides methods of using compositions described herein comprising both a quinolone antibiotic component and an anti-inflammatory steroid component, wherein the anti-inflammatory steroid component (e.g., steroidal, non-steroidal, or both) provides anti-inflammatory activity to treat or prevent inflammation associated with physical trauma to ophthalmic tissue(s), inflammation associated with microbial (e.g., bacterial) infection(s), inflammation resulting from surgical procedure(s), or any combination thereof.

In aspects, compositions provided by the invention are used in lieu of other compositions comprising different active pharmaceutical ingredients to treat an ocular infection, prevent an ocular infection, treat an ocular infection-related condition or symptom such as, e.g., inflammation, prevent an ocular infection-related condition or symptom, or any combination thereof. In aspects, compositions provided by the invention are DOS successfully treat ocular infection and related conditions caused by a higher number of, e.g., broader range of infective agents than compositions comprising different active pharmaceutical ingredients. That is, for example, compositions provided by the invention comprising one or more quinolone antibiotics effectively treat or prevent infection or related condition(s) caused by more infective agents than can be effectively treated or prevented by antibiotic agents such as neomycin, polymyxin B, gentamicin, or tobramycin, an exemplary group of antibiotics whose effectiveness is primarily useful against only gram negative bacteria, or bacitracin, gramicidin, or erythromycin, an exemplary group of antibiotics whose effectiveness is primarily useful against only gram positive bacteria.

In aspects, methods of using compositions provided by the invention, methods treatment using compositions provided by the invention, or both lead to DOS less frequent development of resistant bacteria which are commonly associated with ocular infection than methods of using alternative compositions or methods of treatment using alternative compositions comprising alternative antimicrobial (e.g., antibiotic) agents. In aspects, methods of using compositions provided by the invention, methods of treatment using compositions provided by the invention, or both comprising the antimicrobial agents described here lead to a reduction in the frequency of the development of antibiotic resistant infective bacteria by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, or more over compositions treating the same or similar conditions but which comprise alternative antimicrobial agents, such as, e.g., neomycin, polymyxin B, gentamicin, tobramycin, bacitracin, gramicidin, or erythromycin.

In aspects, the invention provides a method of use described in this section, wherein any one or more of the compositions used in the method are made according to a process/method of manufacturing provided by the invention as described herein. In aspects, the invention provides the method of use of the preceding paragraph wherein the method comprises providing the any one or more compositions for use in the method as a kit provided by the invention as described herein.

In aspects, the invention provides a method of using the composition(s) described herein, wherein the composition used in the method is delivered to the eye in a controlled manner, e.g., a drop-by-drop manner, or, e.g., in a controlled stream of composition, such as, e.g., the pressure and volume of composition in the stream of composition is controllable by the user administering the composition(s). In aspects, the invention provides a composition which is formulated for topical administration and is contained in a delivery device, a device adapted for topical delivery, or is packaged with a delivery device. In aspects, the delivery device is a dropper bottle.

In aspects, the invention provides a method of using the composition(s) described herein, wherein the composition used in the method is delivered to the eye via intracameral injection. In aspects, the invention provides a method of injecting composition(s) described herein into the anterior chamber of a mammalian eye to treat an ocular infection, to prevent an ocular infection in a patient at risk of developing an infection, to treat a condition related to an ocular infection such as inflammation, or to prevent inflammation in a patient at risk of developing inflammation related to an ophthalmic procedure, such as an invasive ophthalmic procedure, e.g., an ophthalmic-related surgery. In aspects, the invention provides a composition which is formulated for injection and contained in an injection delivery device, a device adapted for injection delivery, or is packaged with an injection delivery device.

In aspects, compositions are provided in single dose packaging, and methods of using compositions comprise use of compositions as provided in single dose packaging, such as, e.g., methods comprise the administration of at least one dose of a composition per treatment period. In aspects, compositions are provided in multi-dose packaging, and methods of using compositions comprise use of compositions as provided in multi-dose packaging, such as, e.g., methods comprise the administration of ≥1 dose of a composition per treatment period.

In aspects, the invention provides methods of using compositions described herein over the course of a treatment period of at least about 1 day, such as, e.g., ≥~2 days, ≥~3 days, ≥~4 days, ≥~5 days, ≥~6 days, ≥~7 days, ≥~8 days, ≥~9 days, ≥~11 days, ≥~12 days, ≥~13 days, or, e.g., ≥~14 days or longer. In aspects, the invention provides methods of using compositions described herein over the course of such treatment periods wherein compositions are administered about once per day, such as ~2×/day, ~3×/day, or ~4×/day, as in ~1-4 times/day, ~1-3 times/day, or, e.g., ~1-2 times/day.

In aspects, multi-dose packaging facilitates the ease of use when more than one dose is expected to be used over the course of an administration period.

Methods of Treatment

In aspects, compositions provided by the invention are used to treat ocular infections, such as, e.g., ocular bacterial infection(s), and related conditions or symptoms, such as, e.g., inflammation. Accordingly, in aspects, the invention provides methods of treating ocular infection, related conditions or symptoms, or both.

In aspects, compositions provided by the invention are used to treat bacterial conjunctivitis. In aspects, the invention provides a method of treating bacterial conjunctivitis with composition(s) described here. In aspects, compositions provided by the invention are used to treat bacterial conjunctivitis. In aspects, the bacterial conjunctivitis is caused by a *Streptococcus* sp. infection, such as *Streptococcus pneumoniae*. In aspects, the bacterial conjunctivitis is caused by a *Haemophilus* sp. infection, such as *Haemophilus influenzae*. In aspects, compositions provided by the invention DOS inhibit growth of ≥1 bacteria (i.e., ≥1 bacterial species) causing an ocular bacterial infection. In aspects, such methods DOS reduce infection-associated symptoms such as, e.g., pain, discomfort, itching, redness, swelling, discharge, reduced vision, etc. In aspects, compositions provided by the invention inhibit growth of a bacteria causing an active, ocular bacterial infection by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the infection).

In aspects, compositions provided by the invention are used to treat one or more symptoms of an ocular infection. In aspects, the invention provides a method of treating one or more symptoms of an ocular infection with composition(s) described here. In aspects, the infection arises after an ophthalmological procedure, such as, e.g., an invasive surgical procedure. In aspects, compositions provided by the invention DOS reduce one or more symptoms of an ocular infection such as pain, discomfort, itching, redness, swelling, discharge, and reduced vision.

In aspects, compositions provided by the invention reduce the level of pain associated with an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient when measured in a population of patients in an appropriately conducted and powered clinical trial. Measurement of pain can be performed using any suitable method(s), such as FDA approved pain measurement scales and the like.

In aspects, compositions provided by the invention reduce the level of discomfort associated with an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient when measured in a population of patients in an appropriately conducted and powered clinical (one or more studies characterizable as adequate and well-controlled clinical trial(s) under applicable FDA standards).

In aspects, compositions provided by the invention reduce the amount of itching associated with an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient when measured in a population of patients in an appropriately conducted and powered clinical trial.

In aspects, compositions provided by the invention reduce the level of, or degree of, redness associated with an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient or as measured by an appropriately trained clinician when measured in a population of patients in an appropriately conducted and powered clinical trial.

In aspects, compositions provided by the invention reduce the level of, or degree of, swelling associated with an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient or as measured by an appropriately trained clinician when measured in a population of patients in an appropriately conducted and powered clinical trial.

In aspects, compositions provided by the invention reduce the amount of discharge (e.g., volume of discharge) associated with an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient or as measured by an appropriately trained clinician when measured in a population of patients in an appropriately conducted and powered clinical trial.

In aspects, compositions provided by the invention improve upon a level of reduced vision caused by an ocular infection by a DOS amount or, in aspects, by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the itching) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient or measured by an appropriately trained clinician when measured in a population of patients in an appropriately conducted and powered clinical trial.

In aspects, compositions provided by the invention are used to, i.a., treat or prevent inflammation related to an ocular infection, that arises from treating an ocular infection, or both. In aspects, the invention provides a method of treating ocular inflammation. In aspects, the invention provides a method of preventing ocular inflammation related to an ocular infection, ocular procedure, or both. In aspects, compositions provided by the invention, when administered before an invasive surgical procedure, after an invasive surgical procedure, or both DOS reduce the average percentage of patients experiencing inflammation related to the procedure. In aspects, compositions provided by the invention, when administered before an invasive surgical procedure, after an invasive surgical procedure, or both reduce the average percentage of patients experiencing inflammation related to the procedure by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively preventing infection) over the average percentage of patients contracting an infection related to the same procedure who are not prophylactically treated with composition(s) here. In aspects, compositions provided by the invention, when administered before an invasive surgical procedure, after an invasive surgical procedure, or both reduce the average percentage of patients experiencing inflammation related to an ocular infection contracted in association with the procedure in a DOS amount or by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively preventing infection) over the average percentage of patients contracting an infection related to the same procedure who are not prophylactically treated with composition(s) here. In aspects, compositions provided by the invention reduce the level or degree of inflammation associated with an ocular infection by a DOS amount or at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the inflammation) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient or as measured by a trained clinician when measured in a population of patients in an appropriately conducted and powered clinical trial.

In aspects, compositions provided by the invention are used prophylactically, e.g., to prevent an ocular infection and related conditions. For example, ophthalmic surgical procedures increase the risk of a patient developing an ophthalmic infection. In aspects, compositions provided by the invention are used in connection with an ophthalmic surgical procedure, such as, used prophylactically in connection with such a procedure. For example, compositions provided by the invention are administered before an invasive surgical procedure, after an invasive surgical procedure, or both. In aspects, the invention provides a method of preventing an ocular infection, related condition, or both. In aspects, compositions provided by the invention, when administered before an invasive surgical procedure, after an invasive surgical procedure, or both DOS reduce the average percentage of patients contracting an infection related to the procedure. In aspects, compositions provided by the invention, when administered before an invasive surgical procedure, after an invasive surgical procedure, or both reduce the average percentage of patients contracting an infection related to the procedure by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively preventing infection) over the average percentage of patients contracting an infection related to the same procedure who are not prophylactically treated with composition(s) here.

In aspects, compositions provided by the invention are used to treat one or more symptoms or conditions related to an ocular infection. In aspects, compositions provided by the invention are used to treat one or more symptoms or conditions comprising inflammation related to an ocular infection, such conditions being conditions responsive to, and for which appropriate or acceptable treatment can include, treatment with one or more steroid anti-inflammatory compound(s), treatment with one or more non-steroid anti-inflammatory compounds, or a combination thereof. In aspects, such conditions include, e.g., conjunctivitis, keratitis, blepharitis, dacryocystitis, hordeolum and corneal ulcers. In aspects, compositions herein reduce the level of inflammation present (e.g., as measured by the degree of redness, degree of swelling, degree or level of pain or discomfort associated with the inflammation) by at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, ≥~96%, ≥~97%, ≥~98%, ≥~99%, or, e.g., even 100% (effectively resolving the inflammation associated with the condition) within less than 1 week, such as, e.g., within ≤~6 days, ≤~5 days, ≤~4 days, ≤~3 days, ≤~2 days, or, e.g., ≤~24 hours, such as ≤~12 hours, ≤~6 hours, or even less as reported by the average patient or as measured by a trained clinician when measured in a population of patients in an appropriately conducted and powered clinical trial.

In aspects, compositions herein reduce the length of time of an active ophthalmic infection, reduce the length of time one or conditions related to an ophthalmic condition exist, or both by a DOS amount or at least about 1%, such as, e.g., by ≥~2%, ≥~4%, ≥~6%, ≥~8%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, or, e.g., ≥~75% or more compared to non-treatment of such a condition. In aspects, compositions herein reduce the length of time of an active ophthalmic infection, reduce the length of time one or more conditions related to an ophthalmic condition exist, or both by a DOS amount or at least about 1%, such as, e.g., by ≥~2%, ≥~4%, ≥~5%, ≥~6%, ≥~7%, ≥~8%, ≥~9%, ≥~10%, ≥~11%, ≥~12%, ≥~13%, ≥~14%, ≥~15%, ≥~16%, ≥~17%, ≥~18%, ≥~19%, ≥~20%, or more, such as ≥~25%, ≥~30%, ≥~35%, ≥~40%, ≥~45%, or, e.g., ≥~50%, or more compared to treatment using a similar composition comprising a non-quinolone antibiotic, a non-fluoroquinolone antibiotic, or both.

In aspects, the invention provides a method of treating a patient suffering from an ophthalmic infection, a condition related to an ophthalmic infection (such as, e.g., inflammation), or both, comprising application of a composition comprising pharmaceutically acceptable amounts of each of a quinolone antibiotic component, an anti-inflammatory steroid component, and a suspension component. In aspects, the quinolone antibiotic component is a moxifloxacin compound, such as, e.g., moxifloxacin hydrochloride. In aspects, the antimicrobial agent is a gatifloxacin compound. In aspects, the anti-inflammatory agent is a triamcinolone compound such as, e.g., triamcinolone acetonide. In aspects, the anti-inflammatory agent is a prednisolone compound, such as, e.g., prednisolone acetate. In aspects, the anti-inflammatory agent is a loteprednol compound, such as, e.g., loteprednol etabonate. In aspects, the anti-inflammatory agent is a bromfenac compound, such as bromfenac sodium sesquihydrate. In aspects, the anti-inflammatory steroid component comprises both a prednisolone compound (e.g., prednisolone acetate) and a bromfenac compound (e.g., bromfenac sodium sesquihydrate).

In aspects, the invention provides a method of treating a patient at risk of developing an ophthalmic infection or inflammation, such as a patient undergoing or having completed an invasive ophthalmic procedure (e.g., an ophthalmic-related surgery), comprising application of a composition comprising pharmaceutically acceptable amounts of each of a quinolone antibiotic component, an anti-inflammatory steroid component, and a suspension component. In aspects, the quinolone antibiotic component is a moxifloxacin compound, such as, e.g., moxifloxacin hydrochloride. In aspects, the antimicrobial agent is a gatifloxacin compound. In aspects, the anti-inflammatory agent is a triamcinolone compound such as, e.g., triamcinolone acetonide. In aspects, the anti-inflammatory agent is a prednisolone compound, such as, e.g., prednisolone acetate. In aspects, the anti-inflammatory agent is a loteprednol compound, such as, e.g., loteprednol etabonate. In aspects, the anti-inflammatory agent is a bromfenac compound, such as bromfenac sodium sesquihydrate. In aspects, the anti-inflammatory steroid component comprises both a prednisolone compound (e.g., prednisolone acetate) and a bromfenac compound (e.g., bromfenac sodium sesquihydrate). In aspects, the composition mostly, generally only, or essentially only contains any of such referenced API(s) but can contain amounts of other API(s). In aspects, the referenced API(s) is/are the primary API(s) or essentially the only API(s) of the composition.

In aspects, the invention provides a method of treating a disease or condition benefiting from a combination therapy of antimicrobial and anti-inflammatory compound(s), the method comprising application of a composition comprising pharmaceutically acceptable amounts of each of a quinolone antibiotic component, an anti-inflammatory steroid component, and a suspension component. In aspects, the quinolone antibiotic component is a moxifloxacin compound, such as, e.g., moxifloxacin hydrochloride. In aspects, the antimicrobial agent is a gatifloxacin compound. In aspects, the anti-inflammatory agent is a triamcinolone compound such as, e.g., triamcinolone acetonide. In aspects, the anti-inflammatory agent is a prednisolone compound, such as, e.g., prednisolone acetate. In aspects, the anti-inflammatory agent is a loteprednol compound, such as, e.g., loteprednol etabonate. In aspects, the anti-inflammatory agent is a bromfenac compound, such as bromfenac sodium sesquihydrate. In aspects, the anti-inflammatory steroid component comprises both a prednisolone compound (e.g., prednisolone acetate) and a bromfenac compound (e.g., bromfenac sodium sesquihydrate).

In aspects, the invention provides the methods of treatment described in this section, wherein the compositions further comprise one or more characteristics described elsewhere herein, such as comprising one or more additional excipients, one or more additional APIs, or both, such as comprising, e.g., one or more chelating agents such as an ethylenediaminetetraacetic acid (EDTA) compound (e.g., disodium edetate dihydrate) or salt thereof, one or more surfactants such as polysorbate-80, or one or more preservative(s) (such as sodium citrate, which, in aspects, can also provide buffering, emulsifying, or sequestering activity). In aspects, such compositions can comprise one or more carriers, such as, e.g., an aqueous carrier, e.g., WFI.

In aspects, the invention provides the methods of treatment described in this section, wherein the method is applied a patient who has undergone, or who will receive, an ophthalmologically-related procedure/ophthalmic procedure, such as an invasive ophthalmologically-related procedure/ophthalmic procedure, which is selected from a group comprising cataract surgery and intraocular lens replacement.

In aspects, the invention provides the methods of treatment described in this section, wherein any one or more of the compositions used in the method are made according to a process or method of manufacturing described herein.

In aspects, the invention provides the methods of treatment described in this section, wherein any one or more compositions used in the method are provided for use in the method as a component of a kit as described herein.

In aspects, the invention provides the methods of treatment described in this section, wherein the compositions used in the method are delivered to the eye in a controlled manner, such as, e.g., in a drop-by-drop manner or, e.g., in a controlled stream of composition, such as, e.g., the pressure and volume of composition in the stream of composition is controllable by the user administering the composition(s).

In aspects, the invention provides the methods of treatment described in this section, wherein the compositions used in the method are delivered to the eye by injection, such as, e.g., by intracameral injection.

In aspects, the invention provides the methods of treatment described in this section wherein the composition(s) are administered once, twice, three times, or four times per day for a period of about 1, ~2, ~3, ~4, ~5, ~6, or, e.g., ~7 days.

In aspects, the invention provides the method of treatment of any one or more of the paragraphs of this section, wherein treatment with the composition(s) provides detectably or significantly fewer side effects selected from a group comprising accommodation disturbance, anterior uveitis, blepharitis, conjunctival hyperemia, conjunctivitis, corneal perforation or ulcer, decreased visual acuity, eye infection, glaucoma, increased intraocular pressure, keratitis, mydriasis, optic nerve damage, visual field defect, wound healing impairment, conjunctival irritation, dysgeusia, eye discharge, eye irritation, eye pain, eye redness, eyelid edema, headache, increased lacrimation, papillary conjunctivitis, pyrexia, subconjunctival hemorrhage, tearing, abnormal sensation in eye(s), anterior chamber eye hemorrhage, burning, corneal erosion, corneal thinning, epithelial keratopathy, pruritus, iritis, prolonged bleeding, stinging, or hypersensitivity reaction than treatment with any one or more of ImprimusRx Moxifloxacin Intraocular Solution for Injection, ImprimusRx Prednisolone Acetate Moxifloxacin ophthalmic suspension, ImprimusRx Prednisolone Acetate Moxifloxacin Nepafenac ophthalmic suspension, ImprimusRx Prednisolone-Bromfenac suspension, ImprimusRx Prednisolone-Bromfenac ophthalmic drops, ImprimusRx Prednisolone Sodium Phosphate Bromfenac ophthalmic solution, ImprimusRx Prednisolone-Gatifloxacin-Bromfenac ophthalmic drops, ImprimusRx Prednisolone Acetate Moxifloxacin Bromfenac ophthalmic suspension, and ImprimusRx Triamcinolone Acetonide Moxifloxacin HCl intraocular suspension for Injection. In aspects, compositions of the invention lack one or more of the excipients contained in such compositions. In aspects, compositions of the invention also or alternatively lack any one or more of the excipients described in any of the prior art compositions cited in the Background of the Invention (Background) section of this disclosure.

EXEMPLARY ASPECTS OF THE INVENTION

The following is a non-limiting list of exemplary aspects of the invention.

In aspects, the invention provides an ophthalmologically suitable pharmaceutical composition in the form of a solution or suspension comprising: (a) a suspension component consisting of both (1) an effective amount of least one non-ionic suspension agent and (2) an effective amount of at least one ionic suspension agent; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL (aspect 1).

In aspects, the invention provides the composition of aspect 1, wherein the suspension component of the composition comprises only two suspension agents (aspect 2).

In aspects, the invention provides the composition of one or both of aspect 1 or aspect 2, wherein the ratio of gatifloxacin to the suspension component is from 1:6 to 1:3 (aspect 3).

In aspects, the invention provides the compositions of any one or more of aspects 1-3, wherein the ratio of the ionic suspension agent to the non-ionic suspension agent is from 1:8 to 4:1 (aspect 4).

In aspects, the invention provides the compositions of any one or more of aspects 1-4, wherein the chelating agent is disodium edetate in a concentration of about 0.1 to 0.5 mg/mL (aspect 5).

In aspects, the invention provides the compositions of any one or more of aspects 1-5, wherein the ionic suspension agent comprises an effective amount of a hyaluronic acid, carboxymethylcellulose, acacia gum, or a mixture of any or all thereof (aspect 6).

In aspects, the invention provides the composition of aspect 6, wherein the ionic suspension agent is at least mostly composed of hyaluronic acid (aspect 7).

In aspects, the invention provides the composition of aspect 7, wherein composition comprises hyaluronic acid in a concentration of about 2.0 to about 20.0 mg/mL (aspect 8).

In aspects, the invention provides the composition of one or both of aspect 7 or aspect 8, wherein most of the hyaluronic acid in the composition hyaluronic acid has a molecular weight is from about 360 to about 1200 kDa (aspect 9).

In aspects, the invention provides the composition of any one or more of aspects 7-9, wherein the average molecular weight of most of the hyaluronic acid in the composition is from about 360 to about 1200 kDa (aspect 10).

In aspects, the invention provides the composition of any one or more of aspects 7-10, wherein the composition comprises chondroitin sulfate in a concentration of about 5.0 to about 50.0 mg/mL (aspect 11).

In aspects, the invention provides the composition of any one or more of aspects 1-11, wherein the composition has a pH of from about 6.5 to about 8.5 (aspect 12).

In aspects, the invention provides the composition of any one or more of aspects 1-12, wherein the concentration of gatifloxacin is about 0.5% by weight (aspect 13).

In aspects, the invention provides the composition of any one or more of aspects 1-13, wherein the concentration of prednisolone is about 1.5% by weight (aspect 14).

In aspects, the invention provides the composition of any one or more of aspects 1-14, wherein the concentration of bromfenac is about 0.09% by weight (aspect 15).

In aspects, the invention provides the composition of any one or more of aspects 1-15, wherein the osmolality of the composition is from 200 mOsm/kg to 350 mOsm/kg (aspect 16).

In aspects, the invention provides the composition of any one or more of aspects 1-16, wherein the non-ionic suspension agent is a polysorbate (aspect 17).

In aspects, the invention provides the composition of aspect 17, wherein the non-ionic suspension agent is polysorbate 80 (aspect 18).

In aspects, the invention provides the composition of aspect 18, wherein the polysorbate 80 is present in from 5 mg/mL to about 15 mg/mL (aspect 19).

In aspects, the invention provides the composition of any one or more of aspects 1-19, wherein the composition is devoid of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 20).

In aspects, the invention provides the composition of any one or more of aspects 11-20, wherein at least 2 of the ingredients of the composition are naturally occurring compounds found in the eye (aspect 21).

In aspects, the invention provides the composition of aspect 21, wherein the at least 2 ingredients are naturally occurring compounds found in the vitreous humor of the eye (aspect 22).

In aspects, the invention provides the composition of any one or more of aspects 1-22, wherein at least one ionic suspension agent is an approved FDA product for intracameral injection (aspect 23).

In aspects, the invention provides the composition of any one or more of aspects 1-23, wherein at least one ionic suspension agent is a natural or semi-natural suspension agent having a greater hygroscopicity than that of hydroxypropylmethylcellulose (HPMC) (aspect 24).

In aspects, the invention provides the composition of any one or more of aspects 1-24, wherein at least one ionic suspension agent has a rate of water absorption greater than that of xanthan gum (aspect 25).

In aspects, the invention provides the composition of any one or more of aspects 1-25, wherein at least one ionic suspension agent is a natural or semi-natural suspension agent having a greater hygroscopicity than that of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 26).

In aspects, the invention provides the composition of any one or more of aspects 1-26, wherein the composition is formulated for injection (aspect 27).

In aspects, the invention provides the composition of aspect 27, wherein the composition is provided in a form ready for injection (aspect 28).

In aspects, the invention provides the composition of aspect 28, wherein the composition is provided ready for injection in a pre-filled syringe (aspect 29).

In aspects, the invention provides an ophthalmologically suitable pharmaceutical composition in the form of a solution or suspension comprising: (a) an effective amount of at least one ionic suspension agent; (b) an effective amount of at least one non-ionic surfactant; (c) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (d) a pharmaceutically acceptable chelating agent that results in a significantly similar or improved stability of the active ingredients as compared to disodium edetate in a concentration of about 0.1 to 0.5 mg/mL (aspect 30).

In aspects, the invention provides the composition of aspect 30, wherein the composition comprises only a single ionic suspension agent (aspect 31).

In aspects, the invention provides the composition of one or both of aspect 30 or aspect 31, wherein at least one non-ionic surfactant is also a non-ionic suspension agent (aspect 32).

In aspects, the invention provides the composition of any one or more of aspects 30-32, wherein the non-ionic surfactant comprises an effective amount of a polysorbate, a polyoxyl-ethylated castor oil, or a combination thereof (aspect 33).

In aspects, the invention provides the composition of any one or more of aspects 30-33, wherein the ratio of gatifloxacin to the suspension agent component is from 1:6 to 1:3 (aspect 34).

In aspects, the invention provides the composition of any one or more of aspects 30-34, wherein the ratio of the ionic suspension agent to the non-ionic suspension agent is from 1:8 to 4:1 (aspect 35).

In aspects, the invention provides the composition of any one or more of aspects 30-35, wherein the chelating agent is disodium edetate in a concentration of about 0.1 to 0.5 mg/mL (aspect 36).

In aspects, the invention provides the composition of any one or more of aspects 30-36, wherein the ionic suspension agent comprises an effective amount of a hyaluronic acid, carboxymethylcellulose, acacia gum, or a mixture of any or all thereof (aspect 37).

In aspects, the invention provides the composition of aspect 37, wherein the ionic suspension agent is primarily composed of hyaluronic acid (aspect 38).

In aspects, the invention provides the composition of aspect 38, wherein composition comprises hyaluronic acid in a concentration of about 2.0 to about 20.0 mg/mL (aspect 39).

In aspects, the invention provides the composition of one or both of aspect 38 or aspect 39, wherein most of the hyaluronic acid in the composition hyaluronic acid has a molecular weight is from about 360 to about 1200 kDa (aspect 40).

In aspects, the invention provides the composition of any one or more of aspects 38-40, wherein the average molecular weight of most of the hyaluronic acid in the composition is from about 360 to about 1200 kDa (aspect 41).

In aspects, the invention provides the composition of any one or more of aspects 38-41, wherein the composition comprises chondroitin sulfate in a concentration of about 5.0 to about 50.0 mg/mL (aspect 42).

In aspects, the invention provides the composition of any one or more of aspects 30-42, wherein the composition has a pH of from about 6.5 to about 8.5 (aspect 43).

In aspects, the invention provides the composition of any one or more of aspects 30-43, wherein the concentration of gatifloxacin is about 0.5% by weight (aspect 44).

In aspects, the invention provides the composition of any one or more of aspects 30-44, wherein the concentration of prednisolone is about 1.5% by weight (aspect 45).

In aspects, the invention provides the composition of any one or more of aspects 30-45, wherein the concentration of bromfenac is about 0.09% by weight (aspect 46).

In aspects, the invention provides the composition of any one or more of aspects 30-46, wherein the osmolality of the composition is from 200 mOsm/kg to 350 mOsm/kg (aspect 47).

In aspects, the invention provides the composition of aspect 33, wherein the non-ionic surfactant comprises an effective amount of polysorbate 80 (aspect 48).

In aspects, the invention provides the composition of aspect 33, wherein polysorbate 80 is present in the composition in a concentration of from 5 mg/mL to about 15 mg/mL (aspect 49).

In aspects, the invention provides the composition of aspect 33, wherein the non-ionic surfactant comprises an effective amount of a polyoxyl-ethylated castor oil (aspect 50).

In aspects, the invention provides the composition of aspect 50, wherein the polyoxyl-ethylated castor oil is present in an amount of from about 0.1% to about 1% (aspect 51).

In aspects, the invention provides the composition of one or both of aspect 50 or aspect 51, wherein the composition comprises an effective amount of Cremophor EL (aspect 52).

In aspects, the invention provides the composition of any one or more of aspects 50-52, wherein the composition comprises an effective amount of Cremophor RH-40 (aspect 53).

In aspects, the invention provides the composition of any one or more of aspects 30-53, wherein the composition is devoid of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 54).

In aspects, the invention provides the composition of any one or more of aspects 42-54, wherein at least 2 of the ingredients of the composition are naturally occurring compounds found in the eye (aspect 55).

In aspects, the invention provides the composition of aspect 55, wherein the at least 2 ingredients are naturally occurring compounds found in the vitreous humor of the eye (aspect 56).

In aspects, the invention provides the composition of any one or more of aspects 30-56, wherein at least one ionic suspension agent is an approved FDA product for intracameral injection (aspect 57).

In aspects, the invention provides the composition of any one or more of aspects 30-57, wherein at least one ionic suspension agent is a natural or semi-natural suspension agent having a greater hygroscopicity than that of hydroxypropylmethylcellulose (HPMC) (aspect 58).

In aspects, the invention provides the composition of any one or more of aspects 30-58, wherein at least one ionic suspension agent has a rate of water absorption greater than that of xanthan gum (aspect 59).

In aspects, the invention provides the composition of any one or more of aspects 30-59, wherein at least one ionic suspension agent is a natural or semi-natural suspension agent having a greater hygroscopicity than that of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 60).

In aspects, the invention provides the composition of any one or more of aspects 30-60, wherein the composition is formulated for injection (aspect 61).

In aspects, the invention provides the composition of aspect 61, wherein the composition is provided in a form ready for injection (aspect 62).

In aspects, the invention provides the composition of aspect 62, wherein the composition is provided ready for injection in a pre-filled syringe (aspect 63).

In aspects, the invention provides an ophthalmologically suitable pharmaceutical composition in the form of a solution or suspension comprising: (a) at least 1.5 wt. % of a suspension agent component comprising an effective amount of a natural or semi-synthetic suspension agent other than xanthan gum; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL, (d) wherein (a) the composition has a viscosity of about 3.5-about 25 mPas and (b) the composition exhibits significantly less flocculation, coagulation, clumping, or combination of any or all thereof as opposed to a corresponding formulation comprising xanthan gum in place of the suspension agent (aspect 64).

In aspects, the invention provides the composition of aspect 64, wherein the composition comprises only a single natural or semi-synthetic suspension agent (aspect 65).

In aspects, the invention provides the composition of one or both of aspect 64 or aspect 65, wherein the composition further comprises an effective amount of a non-ionic surfactant (aspect 66).

In aspects, the invention provides the composition of aspect 66, wherein the non-ionic surfactant is also a suspension agent (aspect 67).

In aspects, the invention provides the composition of one or both of aspect 66 or aspect 67, wherein the non-ionic surfactant comprises an effective amount of a polysorbate, a polyoxyl-ethylated castor oil, or a combination thereof (aspect 68).

In aspects, the invention provides the composition of any one or more of aspects 64-68, wherein the ratio of gatifloxacin to the suspension agent component is from 1:3 to 1:6 (aspect 69).

In aspects, the invention provides the composition of any one or more of aspects 64-69, wherein the ratio of the ionic suspension agent to the non-ionic suspension agent is from 1:8 to 4:1 (aspect 70).

In aspects, the invention provides the composition of any one or more of aspects 64-70, wherein the chelating agent is disodium edetate in a concentration of about 0.1 to 0.5 mg/mL (aspect 71).

In aspects, the invention provides the composition of any one or more of aspects 64-71, wherein the suspension agent has an average molecular weight of less than 1200 kDa (aspect 72).

In aspects, the invention provides the composition of aspect 72, wherein the suspension agent has an average molecular weight of less than 1000 kDa (aspect 73).

In aspects, the invention provides the composition of any one or more of aspects 64-73, wherein the suspension agent comprises an effective amount of a hyaluronic acid, carboxymethylcellulose, acacia gum, or a mixture of any or all thereof (aspect 74).

In aspects, the invention provides the composition of any one or more of aspects 64-74, wherein the suspension agent comprises an effective amount of hyaluronic acid (aspect 75).

In aspects, the invention provides the composition of any one or more of aspects 64-74, wherein composition comprises hyaluronic acid in a concentration of about 2.0 to about 20.0 mg/mL (aspect 76).

In aspects, the invention provides the composition of one or both of aspect 75 or aspect 76, wherein most of the hyaluronic acid in the composition hyaluronic acid has a molecular weight is from about 360 to about 1200 kDa (aspect 77).

In aspects, the invention provides the composition of any one or more of aspects 75-77, wherein the average molecular weight of most of the hyaluronic acid in the composition is from about 360 to about 1200 kDa (aspect 78).

In aspects, the invention provides the composition of any one or more of aspects 75-78, wherein the composition comprises chondroitin sulfate in a concentration of about 5.0 to about 50.0 mg/mL (aspect 79).

In aspects, the invention provides the composition of any one or more of aspects 64-79, wherein the composition has a pH of from about 6.5 to about 8.5 (aspect 80).

In aspects, the invention provides the composition of any one or more of aspects 64-80, wherein the concentration of gatifloxacin is about 0.5% by weight (aspect 81).

In aspects, the invention provides the composition of any one or more of aspects 64-81, wherein the concentration of prednisolone is about 1.5% by weight (aspect 82).

In aspects, the invention provides the composition of any one or more of aspects 64-82, wherein the concentration of bromfenac is about 0.09% by weight (aspect 83).

In aspects, the invention provides the composition of any one or more of aspects 64-83, wherein the osmolality of the composition is from 200 mOsm/kg to 350 mOsm/kg (aspect 84).

In aspects, the invention provides the composition of aspect 67, wherein the non-ionic suspension agent comprises an effective amount of a polysorbate (aspect 85).

In aspects, the invention provides the composition of aspect 85, wherein the non-ionic suspension agent is polysorbate 80 (aspect 86).

In aspects, the invention provides the composition of aspect 86, wherein the polysorbate 80 is present in from 5 mg/mL to about 15 mg/mL (aspect 87).

In aspects, the invention provides the composition of any one or more of aspects 64-87, wherein the composition is devoid of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 88).

In aspects, the invention provides the composition of any one or more of aspects 64-88, wherein the composition is free of hydroxypropyl methylcellulose (aspect 89).

In aspects, the invention provides the composition of any one or more of aspects 79-89, wherein at least 2 of the ingredients of the composition are naturally occurring compounds found in the eye (aspect 90).

In aspects, the invention provides the composition of aspect 90, wherein the at least 2 ingredients are naturally occurring compounds found in the vitreous humor of the eye (aspect 91).

In aspects, the invention provides the composition of any one or more of aspects 64-91, wherein at least one ionic suspension agent is an approved FDA product for intracameral injection (aspect 92).

In aspects, the invention provides the composition of any one or more of aspects 64-92, wherein at least one ionic suspension agent is a natural or semi-natural suspension agent having a greater hygroscopicity than that of hydroxypropylmethylcellulose (HPMC) (aspect 93).

In aspects, the invention provides the composition of any one or more of aspects 64-93, wherein at least one ionic suspension agent has a rate of water absorption greater than that of xanthan gum (aspect 94).

In aspects, the invention provides the composition of any one or more of aspects 64-94, wherein at least one ionic suspension agent is a natural or semi-natural suspension agent having a greater hygroscopicity than that of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 95).

In aspects, the invention provides the composition of any one or more of aspects 64-95, wherein the composition is formulated for injection (aspect 96).

In aspects, the invention provides the composition of aspect 96, wherein the composition is provided in a form ready for injection (aspect 97).

In aspects, the invention provides the composition of aspect 97, wherein the composition is provided ready for injection in a pre-filled syringe (aspect 98).

In aspects, the invention provides an ophthalmologically suitable pharmaceutical composition in the form of a solution or suspension comprising: (a) an effective amount of at least one natural or semi-synthetic suspension agent composed of a compound having an average molecular weight of between 10,000 and 1,000,000 Daltons; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL (aspect 99).

In aspects, the invention provides the composition of aspect 99, wherein the composition comprises only a single natural or semi-synthetic suspension agent (aspect 100).

In aspects, the invention provides the composition of one or both of aspect 99 or aspect 100, wherein the composition further comprises an effective amount of a non-ionic surfactant (aspect 101).

In aspects, the invention provides the composition of aspect 101, wherein the non-ionic surfactant is also a suspension agent (aspect 102).

In aspects, the invention provides the composition of one or both of aspect 101 or aspect 102, wherein the non-ionic surfactant comprises an effective amount of a polysorbate, a polyoxyl-ethylated castor oil, or a combination thereof (aspect 103).

In aspects, the invention provides the composition of any one or more of aspects 99-103, wherein the ratio of gatifloxacin to the suspension agent component is from 1:6 to 1:3 (aspect 104).

In aspects, the invention provides the composition of any one or more of aspects 99-104, wherein the ratio of the ionic suspension agent to the non-ionic suspension agent is from 1:8 and 4:1 (aspect 105).

In aspects, the invention provides the composition of any one or more of aspects 99-105, wherein the chelating agent is disodium edetate in a concentration of about 0.1 to 0.5 mg/mL (aspect 106).

In aspects, the invention provides the composition of any one or more of aspects 99-106, wherein the suspension agent comprises an effective amount of a hyaluronic acid, acacia gum, or a mixture of any or all thereof (aspect 107).

In aspects, the invention provides the composition of any one or more of aspects 99-107, wherein the suspension agent comprises an effective amount of hyaluronic acid (aspect 108).

In aspects, the invention provides the composition of any one or more of aspects 99-107, wherein composition comprises hyaluronic acid in a concentration of about 2.0 to about 20.0 mg/mL (aspect 109).

In aspects, the invention provides the composition of one or both of aspect 108 or aspect 109, wherein most of the hyaluronic acid in the composition hyaluronic acid has a molecular weight is from about 360 to about 1200 kDa (aspect 110).

In aspects, the invention provides the composition of any one or more of aspects 106-110, wherein the average molecular weight of most of the hyaluronic acid in the composition is from about 360 to about 1200 kDa (aspect 111).

In aspects, the invention provides the composition of any one or more of aspects 108-111, wherein the composition comprises chondroitin sulfate in a concentration of about 5.0 to about 50.0 mg/mL (aspect 112).

In aspects, the invention provides the composition of any one or more of aspects 99-112, wherein the composition has a pH of from about 6.5 to about 8.5 (aspect 113).

In aspects, the invention provides the composition of any one or more of aspects 99-113, wherein the concentration of gatifloxacin is about 0.5% by weight (aspect 114).

In aspects, the invention provides the composition of any one or more of aspects 99-114, wherein the concentration of prednisolone is about 1.5% by weight (aspect 115).

In aspects, the invention provides the composition of any one or more of aspects 99-115, wherein the concentration of bromfenac is about 0.09% by weight (aspect 116).

In aspects, the invention provides the composition of any one or more of aspects 99-116, wherein the osmolality of the composition is from 200 mOsm/kg to 350 mOsm/kg (aspect 117).

In aspects, the invention provides the composition of aspect 103, wherein the non-ionic suspension agent comprises an effective amount of a polysorbate (aspect 118).

In aspects, the invention provides the composition of aspect 118, wherein the non-ionic suspension agent is polysorbate 80 (aspect 119).

In aspects, the invention provides the composition of aspect 119, wherein the polysorbate 80 is present in from 5 mg/mL to about 15 mg/mL (aspect 120).

In aspects, the invention provides the composition of any one or more of aspects 99-120, wherein the composition is devoid of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 121).

In aspects, the invention provides the composition of any one or more of aspects 99-121, wherein the composition is free of hydroxypropyl methylcellulose (aspect 122).

In aspects, the invention provides the composition of any one or more of aspects 112-122, wherein at least 2 of the ingredients of the composition are naturally occurring compounds found in the eye (aspect 123).

In aspects, the invention provides the composition of aspect 123, wherein the at least 2 ingredients are naturally occurring compounds found in the vitreous humor of the eye (aspect 124).

In aspects, the invention provides the composition of any one or more of aspects 99-124, wherein at least one ionic suspension agent is an approved FDA product for intracameral injection (aspect 125).

In aspects, the invention provides the composition of any one or more of aspects 99-125, wherein at least one ionic suspension agent is a natural or semi-natural suspension agent having a greater hygroscopicity than that of hydroxypropylmethylcellulose (HPMC) (aspect 126).

In aspects, the invention provides the composition of any one or more of aspects 99-126, wherein at least one ionic suspension agent has a rate of water absorption greater than that of xanthan gum (aspect 127).

In aspects, the invention provides the composition of any one or more of aspects 99-127, wherein at least one ionic suspension agent is a natural or semi-natural suspension agent having a greater hygroscopicity than that of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 128).

In aspects, the invention provides the composition of any one or more of aspects 99-128, wherein the composition is formulated for injection (aspect 129).

In aspects, the invention provides the composition of aspect 129, wherein the composition is provided in a form ready for injection (aspect 130).

In aspects, the invention provides the composition of aspect 130, wherein the composition is provided ready for injection in a pre-filled syringe (aspect 131).

In aspects, the invention provides an ophthalmologically suitable pharmaceutical composition in the form of a solution or suspension comprising: (a) an effective amount of a suspension agent comprising effective amounts of two non-ionic suspension agents, one of which nonionic suspension agents having surface active activity; (b) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (c) a pharmaceutically acceptable chelating agent that results in a significantly similar or improved stability of the active ingredients as compared to disodium edetate in a concentration of about 0.1 to 0.5 mg/mL (aspect 132).

In aspects, the invention provides the composition of aspect 132, wherein the composition comprises only two suspension agents (aspect 133).

In aspects, the invention provides the composition of one or both of aspect 132 or aspect 133, wherein non-ionic suspension agent that is a non-ionic surfactant comprises an effective amount of a polysorbate, a polyoxyl-ethylated castor oil, or a combination thereof (aspect 134).

In aspects, the invention provides the composition of any one or more of aspects 132-134, wherein the ratio of gatifloxacin to the suspension agent component is from 1:6 to 1:3 (aspect 135).

In aspects, the invention provides the composition of any one or more of aspects 132-135, wherein the ratio of the ionic suspension agent to the nonionic suspension agent is from 1:8 and 4:1 (aspect 136).

In aspects, the invention provides the composition of any one or more of aspects 132-136, wherein the chelating agent is disodium edetate in a concentration of about 0.1 to 0.5 mg/mL (aspect 137).

In aspects, the invention provides the composition of any one or more of aspects 132-138, wherein the suspension agent that is not a non-ionic surfactant comprises an effective amount of a hyaluronic acid, acacia gum, or a mixture of any or all thereof (aspect 138).

In aspects, the invention provides the composition of aspect 137, wherein the suspension agent comprises an effective amount of hyaluronic acid (aspect 139).

In aspects, the invention provides the composition of aspect 137, wherein composition comprises hyaluronic acid in a concentration of about 2.0 to about 20.0 mg/mL (aspect 140).

In aspects, the invention provides the composition of one or both of aspect 139 or aspect 140, wherein most of the hyaluronic acid in the composition hyaluronic acid has a molecular weight is from about 360 to about 1200 kDa (aspect 141).

In aspects, the invention provides the composition of any one or more of aspects 139-141, wherein the average molecular weight of most of the hyaluronic acid in the composition is from about 360 to about 1200 kDa (aspect 142).

In aspects, the invention provides the composition of any one or more of aspects 139-142, wherein the composition comprises chondroitin sulfate in a concentration of about 5.0 to about 50.0 mg/mL (aspect 143).

In aspects, the invention provides the composition of any one or more of aspects 99-143, wherein the composition has a pH of from about 6.5 to about 8.5 (aspect 144).

In aspects, the invention provides the composition of any one or more of aspects 99-144, wherein the concentration of gatifloxacin is about 0.5% by weight (aspect 145).

In aspects, the invention provides the composition of any one or more of aspects 99-145, wherein the concentration of prednisolone is about 1.5% by weight (aspect 146).

In aspects, the invention provides the composition of any one or more of aspects 99-146, wherein the concentration of bromfenac is about 0.09% by weight (aspect 147).

In aspects, the invention provides the composition of any one or more of aspects 99-147, wherein the osmolality of the composition is from 200 mOsm/kg to 350 mOsm/kg (aspect 148).

In aspects, the invention provides the composition of aspect 101, wherein the non-ionic suspension agent that is a non-ionic surfactant comprises an effective amount of a polysorbate (aspect 149).

In aspects, the invention provides the composition of aspect 116, wherein the non-ionic suspension agent that is a non-ionic surfactant is polysorbate 80 (aspect 150).

In aspects, the invention provides the composition of aspect 117, wherein the polysorbate 80 is present in from 5 mg/mL to about 15 mg/mL (aspect 151).

In aspects, the invention provides the composition of any one or more of aspects 99-118, wherein the composition is devoid of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 152).

In aspects, the invention provides the composition of any one or more of aspects 99-119, wherein the composition is free of hydroxypropyl methylcellulose (aspect 153).

In aspects, the invention provides the composition of any one or more of aspects 110-120, wherein at least 2 of the ingredients of the composition are naturally occurring compounds found in the eye (aspect 154).

In aspects, the invention provides the composition of aspect 154, wherein the at least 2 ingredients are naturally occurring compounds found in the vitreous humor of the eye (aspect 155).

In aspects, the invention provides the composition of any one or more of aspects 99-155, wherein at least one ionic suspension agent is an approved FDA product for intracameral injection (aspect 156).

In aspects, the invention provides the composition of any one or more of aspects 99-156, wherein at least one ionic suspension agent is a natural or semi-natural suspension agent having a greater hygroscopicity than that of hydroxypropylmethylcellulose (HPMC) (aspect 157).

In aspects, the invention provides the composition of any one or more of aspects 99-157, wherein at least one ionic suspension agent has a rate of water absorption greater than that of xanthan gum (aspect 158).

In aspects, the invention provides the composition of any one or more of aspects 99-125, wherein at least one ionic suspension agent is a natural or semi-natural suspension agent having a greater hygroscopicity than that of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 159).

In aspects, the invention provides the composition of any one or more of aspects 99-159, wherein the composition is formulated for injection (aspect 160).

In aspects, the invention provides the composition of aspect 160, wherein the composition is provided in a form ready for injection (aspect 161).

In aspects, the invention provides the composition of aspect 161, wherein the composition is provided ready for injection in a pre-filled syringe (aspect 162).

In aspects, the invention provides an ophthalmologically suitable pharmaceutical composition in the form of a solution or suspension comprising: (a) an effective amount of a suspension agent; (b) an effective amount of a polyoxylethylated castor oil; (c) at least three pharmaceutical ingredients comprising (1) gatifloxacin in a range of about 0.1% to about 1.0% by weight, (2) prednisolone in a range of about 0.1% to about 5% by weight, and (3) bromfenac in a range of about 0.01% to about 0.1% by weight, or a pharmaceutically acceptable salt thereof; and (d) a pharmaceutically acceptable chelating agent that results in a significantly similar or improved stability of the active ingredients as compared to disodium edetate in a concentration of about 0.1 to 0.5 mg/mL (aspect 163).

In aspects, the invention provides the composition of aspect 163, wherein the composition comprises from about 0.1-about 1% of polyoxyl-ethylated castor oil (aspect 164).

In aspects, the invention provides the composition of one or both of aspect 163 or aspect 164, wherein the composition comprises an effective amount of Cremophor EL (aspect 165).

In aspects, the invention provides the composition of one or both of aspect 163 or aspect 164, wherein the composition comprises an effective amount of Cremophor RH-40 (aspect 166).

In aspects, the invention provides the composition of any one or more of aspects 163-166, wherein the composition comprises only a single suspension agent (aspect 167).

In aspects, the invention provides the composition of any one or more of aspects 163-167, wherein the ratio of gatifloxacin to the suspension agent component is from 1:6 to 1:3 (aspect 168).

In aspects, the invention provides the composition of any one or more of aspects 163-168, wherein the ratio of the ionic suspension agent to the non-ionic suspension agent is from 1:8 to 4:1 (aspect 169).

In aspects, the invention provides the composition of any one or more of aspects 163-169, wherein the chelating agent is disodium edetate in a concentration of about 0.1 to 0.5 mg/mL (aspect 170).

In aspects, the invention provides the composition of any one or more of aspects 163-170, wherein the suspension agent is an ionic suspension agent (aspect 171).

In aspects, the invention provides the composition of aspect 171, wherein the ionic suspension agent comprises an effective amount of a hyaluronic acid, carboxymethylcellulose, acacia gum, or a mixture of any or all thereof (aspect 172).

In aspects, the invention provides the composition of aspect 172, wherein the ionic suspension agent comprises an effective amount of hyaluronic acid (aspect 173).

In aspects, the invention provides the composition of aspect 173, wherein composition comprises hyaluronic acid in a concentration of about 2.0 to about 20.0 mg/mL (aspect 174).

In aspects, the invention provides the composition of any one or more of aspect 173 or aspect 174, wherein most of the hyaluronic acid in the composition hyaluronic acid has a molecular weight is from about 360 to about 1200 kDa (aspect 175).

In aspects, the invention provides the composition of any one or more of aspects 173-175, wherein the average molecular weight of most of the hyaluronic acid in the composition is from about 360 to about 1200 kDa (aspect 176).

In aspects, the invention provides the composition of any one or more of aspects 173-176, wherein the composition comprises chondroitin sulfate in a concentration of about 5.0 to about 50.0 mg/mL (aspect 177).

In aspects, the invention provides the composition of aspect 172, wherein the composition comprises an effective amount of carboxymethylcellulose (aspect 178).

In aspects, the invention provides the composition of any one or more of aspects 163-170, wherein the suspension agent is a non-ionic suspension agent (aspect 179).

In aspects, the invention provides the composition of aspect 179, wherein the non-ionic suspension agent comprises an effective amount of methylcellulose, hydroxyethylcellulose, gelatin, polyvinylpyrrolidone, polyethylene glycol, or a mixture of any or all thereof (aspect 180).

In aspects, the invention provides the composition of any one or more of aspects 163-177, wherein the composition has a pH of from about 6.5 to about 8.5 (aspect 181).

In aspects, the invention provides the composition of any one or more of aspects 163-181, wherein the concentration of gatifloxacin is about 0.5% by weight (aspect 182).

In aspects, the invention provides the composition of any one or more of aspects 163-182, wherein the concentration of prednisolone is about 1.5% by weight (aspect 183).

In aspects, the invention provides the composition of any one or more of aspects 163-183, wherein the concentration of bromfenac is about 0.09% by weight (aspect 184).

In aspects, the invention provides the composition of any one or more of aspects 163-184, wherein the osmolality of the composition is from 200 mOsm/kg to 350 mOsm/kg (aspect 185).

In aspects, the invention provides the composition of any one or more of aspects 177-185, wherein at least 2 of the ingredients of the composition are naturally occurring compounds found in the eye (aspect 186).

In aspects, the invention provides the composition of aspect 186, wherein the at least 2 ingredients are naturally occurring compounds found in the vitreous humor of the eye (aspect 187).

In aspects, the invention provides the composition of any one or more of aspects 163-187, wherein at least one ionic suspension agent is an approved FDA product for intracameral injection (aspect 188).

In aspects, the invention provides the composition of any one or more of aspects 163-186, wherein at least one ionic suspension agent is a natural or semi-natural suspension agent having a greater hygroscopicity than that of hydroxypropylmethylcellulose (HPMC) (aspect 189).

In aspects, the invention provides the composition of any one or more of aspects 163-189, wherein at least one ionic suspension agent has a rate of water absorption greater than that of xanthan gum (aspect 190).

In aspects, the invention provides the composition of any one or more of aspects 163-190, wherein at least one ionic suspension agent is a natural or semi-natural suspension agent having a greater hygroscopicity than that of a non-ionic polyoxyethylene-polyoxypropylene block copolymer having the following chemical structure —HO—(CH2-CH2-O)x-(C3H6-O)y-(CH2-CH2-O)x-H, wherein x is an integer having the value of at least 8 and y is an integer having the value of at least 38 (aspect 191).

In aspects, the invention provides the composition of any one or more of aspects 163-191, wherein the composition is formulated for injection (aspect 192).

In aspects, the invention provides the composition of aspect 192, wherein the composition is provided in a form ready for injection (aspect 193).

In aspects, the invention provides the composition of aspect 193, wherein the composition is provided ready for injection in a pre-filled syringe (aspect 194).

In aspects, the invention provides a kit comprising a pharmaceutically acceptable composition of any one or more of aspects 1-194 packaged in one or more single use containers, wherein the kit further comprises one or more delivery devices for administering the composition to a recipient (aspect 195).

In aspects, the invention provides the kit of aspect 195, wherein the delivery device is a syringe system (aspect 196).

In aspects, the invention provides the kit of aspect 196, wherein the delivery device is a syringe system wherein any single use container comprising a pharmaceutically acceptable composition present in the kit is accessible to a delivery device/system of the kit, such as, e.g., containing a stopper which effectively seals the single use container but which is penetrable by the delivery device/system such that the delivery device can extract the composition from the single use container (aspect 197).

In aspects, the invention provides the kit of aspect 196 or aspect 197, wherein the delivery system is a syringe system and wherein the composition(s) are individual packaged in pre-filled syringes (aspect 198).

In aspects, the invention provides the kit of aspect 198, wherein 1 or more individual doses of between about 0.5 mL-about 5 mL of composition are provided (aspect 199).

In aspects, the invention provides the kit of aspects 195-199, wherein the delivery system is a dropper bottle for providing the composition in a drop-by-drop manner (aspect 200).

In aspects, the invention provides the kit of aspect 200, wherein the kit comprises one or more dropper bottles each comprising between about 1 mL and about 10 mL of a carrier composition (aspect 201).

In aspects, the invention provides a method of using any one or more pharmaceutically acceptable and ophthalmologically suitable compositions described herein to treat or prevent inflammation associated with physical trauma to ophthalmic tissue(s), inflammation associated with microbial (e.g., bacterial) infection(s), inflammation resulting from surgical procedure(s), or any combination thereof (aspect 202).

In aspects, the invention provides a method of using any one or more pharmaceutically acceptable and ophthalmologically suitable compositions described herein to treat or prevent an ocular microbial infection (aspect 203).

In aspects, the invention provides a method of using any one or more pharmaceutically acceptable and ophthalmologically suitable compositions described herein to treat or prevent significant inflammation associated with physical trauma to ophthalmic tissue(s), significant inflammation associated with microbial (e.g., bacterial) infection(s), inflammation resulting from surgical procedure(s), to treat or prevent an ocular microbial infection, or any combination thereof (aspect 204).

In aspects, the invention provides the method of any one or more of aspects 202-204, wherein the method comprises providing the any one or more pharmaceutically acceptable and ophthalmologically suitable compositions for use in the method as a kit of any one or more of aspects 195-201 (aspect 205).

In aspects, the invention provides the method of any one or more of aspects 202-205, wherein the pharmaceutically acceptable and ophthalmologically suitable composition is delivered to the eye in a controlled manner (aspect 206).

In aspects, the invention provides the method of any one or more of aspects 202-206, wherein the pharmaceutically acceptable and ophthalmologically suitable composition is delivered in a drop-by-drop manner (aspect 207).

In aspects, the invention provides the method of any one or more of aspects 202-207, wherein the pharmaceutically acceptable and ophthalmologically suitable composition is delivered to the eye by injection, e.g., by intracameral injection (aspect 208).

In aspects, the invention provides a method of treating or preventing a disease or condition benefiting from a combination therapy of an quinolone antibiotic antimicrobial component and a steroid or steroid and non-steroid anti-inflammatory component, the method comprising administering an effective amount of a pharmaceutically acceptable and ophthalmologically suitable composition, comprising pharmaceutically acceptable amounts of any one or more compositions of aspects 1-194 (aspect 209).

In aspects, the invention provides the method of aspect 209, wherein the disease or condition is bacterial conjunctivitis (aspect 210).

In aspects, the invention provides the method of aspect 209, wherein the disease or condition is an ocular infection (aspect 211).

In aspects, the invention provides the method of aspect 209, wherein the disease or condition is an ocular infection, inflammation, or both arising after an invasive ophthalmic procedure (aspect 212).

In aspects, the invention provides the method of aspect 209, wherein the ophthalmologically-related procedure is selected from a group comprising cataract surgery and intraocular lens replacement (aspect 213).

In aspects, the invention provides the method of aspect 209, wherein the disease or condition is conjunctivitis, keratitis, blepharitis, dacryocytitis, hordeoleum, and corneal ulcers (aspect 214).

In aspects, the invention provides the method of aspect 209, wherein the method comprises providing the any one or more pharmaceutically acceptable and ophthalmologically suitable compositions for use in the method as a kit of any one or more of aspects 195-201 (aspect 215).

In aspects, the invention provides the method of any one or more of aspects 209-215, wherein the pharmaceutically acceptable and ophthalmologically suitable composition is delivered in a drop-by-drop manner (aspect 216).

In aspects, the invention provides the method of any one or more of aspects 209-216, wherein the pharmaceutically acceptable and ophthalmologically suitable composition is administered prior to an ophthalmologically-related procedure (aspect 217).

In aspects, the invention provides the method of any one or more of aspects 209-217, wherein the pharmaceutically acceptable and ophthalmologically suitable composition is administered for a period following an ophthalmologically-related procedure (aspect 218).

In aspects, the invention provides the method of any one or more of aspects 209-218, wherein the pharmaceutically acceptable and ophthalmologically suitable composition is administered over an administration period ranging from a one-time administration to an administration of twice, or three times per day for a period of between about 1-7 days (aspect 219).

In aspects, the invention provides the method of any one or more of aspects 209-219, wherein treatment with the pharmaceutically acceptable and ophthalmologically suitable composition provides detectably or significantly fewer side effects selected from a group accommodation disturbance, anterior uveitis, blepharitis, conjunctival hyperemia, conjunctivitis, corneal perforation or ulcer, decreased visual acuity, eye infection, glaucoma, increased intraocular pressure, keratitis, mydriasis, optic nerve damage, visual field defect, wound healing impairment, conjunctival irritation, dysgeusia, eye discharge, eye irritation, eye pain, eye redness, eyelid edema, headache, increased lacrimation, papillary conjunctivitis, pyrexia, subconjunctival hemorrhage, tearing, abnormal sensation in eye(s), anterior chamber eye hemorrhage, burning, corneal erosion, corneal thinning, epithelial keratopathy, pruritis, iritis, prolonged bleeding, stinging, or hypersensitivity reaction than treatment with any one or more of ImprimusRx Moxifloxacin Intraocular Solution for Injection, ImprimusRx Prednisolone Acetate Moxifloxacin Ophthalmic Suspension, ImprimusRx Prednisolone Acetate Moxifloxacin Nepafenac Ophthalmic Suspension, ImprimusRx Prednisolone-Bromfenac Suspension, ImprimusRx Prednisolone-Bromfenac Ophthalmic Drops, ImprimusRx Prednisolone Sodium Phosphate Bromfenac Ophthalmic Solution, ImprimusRx Prednisolone-Gatifloxacin-Bromfenac Ophthalmic Drops, ImprimusRx Prednisolone Acetate Moxifloxacin Bromfenac Ophthalmic Suspension, and ImprimusRx Triamcinolone Acetonide Moxifloxacin HCl Intraocular Suspension for Injection (aspect 220).

EXAMPLES
(TRIAMCINOLONE+MOXIFLOXACIN)

The following ophthalmologically suitable antimicrobial-anti-inflammatory combination formulations of Table 2 were generated according to the following procedures.

TABLE 2

Exemplary Formulations.

| INGREDIENT | QUANTITY/mL (mg) | | | | |
|---|---|---|---|---|---|
| | Form. I | Form. II | Form. III | Form. IV | Form. V |
| Triamcinolone acetonide (as base) | 10.0-20.0 | 10.0-20.0 | 10.0-20.0 | 10.0-20.0 | 1.0-30.0 |
| Moxifloxacin HCl (as base) | 1.0 | 1.0 | 1.0 | 1.0 | 1.0 |
| Polysorbate-80 | 10.0 | 10.0 | 10.0 | 10.0 | 10.0 |
| Polyethylene glycol 3350 (PEG 3350) | — | 10.0-100.0 | — | — | — |
| Hyaluronic acid | 2.0-20.0 | — | — | 2.0-20.0 | 2.0-20.0 |
| Sodium carboxymethyl cellulose (CMC) | — | — | 2.0-20.0 | — | — |
| Chondroitin sulfate | — | — | — | 5.0-50.0 | 50-50.0 |
| Sodium citrate monohydrate | 1.0-10.0 | 1.0-10.0 | 1.0-10.0 | 1.0-10.0 | 1.0-10.0 |
| Disodium edetate dihydrate | 1.0-5.0 | 1.0-5.0 | 1.0-5.0 | 1.0-5.0 | 1.0-5.0 |
| Benzalkonium chloride | — | — | — | — | 0.05 |
| Hydrochloric acid/ sodium hydroxide | QS to adjust pH to 7.0 ± 0.2 | QS to adjust pH to 7.0 ± 0.2 | QS to adjust pH to 7.0 ± 0.2 | QS to adjust pH to 7.0 ± 0.2 | QS to adjust pH to 7.0 ± 0.2 |
| Water | QS to 1.0 mL | QS to 1.0 mL | QS to 1.0 mL | QS to 1.0 mL | QS to 1.0 mL |

("Form." = formulation)

Example 1

Moxifloxacin Hydrochloride and Triamcinolone Acetonide Ophthalmic Suspension (Single Dose)

The composition having Formulation I was manufactured according to the following process.

Part I:
1. The total quantity of triamcinolone acetonide was added to 30% of the total required volume of water forming a triamcinolone acetonide suspension.
2. The triamcinolone acetonide suspension was passed through a homogenizer to form a suspension of particles having a D50 particle size of 0.5-1.5 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 50% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. The total quantity of hyaluronic acid was added to the completely dissolved solution of sodium citrate monohydrate, polysorbate-80, and disodium edetate dihydrate and stirred for 2 hours at moderate speed (to ensure complete dissolution of the hyaluronic acid).
5. Upon complete dissolution of the hyaluronic acid, the resulting solution was autoclaved at 121° C. for 20 minutes.
6. The solution was allowed to cool after autoclaving.
7. Once the solution was cooled to room temperature, the total quantity of moxifloxacin was added and allowed to completely dissolve.
8. The resulting solution was QS to 65% of the final volume.
9. The pH was adjusted using pH adjusting agents (HCl and NaOH) to 7.0±0.2.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 2

Moxifloxacin Hydrochloride and Triamcinolone Acetonide Ophthalmic Suspension (Single Dose)

The composition having Formulation II was manufactured according to the following process.

Part I:
1. The total quantity of triamcinolone acetonide was added to 30% of the total required volume of water forming a triamcinolone acetonide suspension.
2. The triamcinolone acetonide suspension was passed through a homogenizer to form a suspension of particles having a D50 particle size of 0.5-1.5 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.

2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate in the sodium citrate monohydrate and polysorbate-80 solution, the complete quantity of moxifloxacin hydrochloride was added and stirred until completely dissolved.
5. Upon complete dissolution of moxifloxacin hydrochloride, the total quantity of PEG 3350 was added to the completely dissolved solution of sodium citrate monohydrate, polysorbate-80, disodium edetate dihydrate and moxifloxacin hydrochloride and stirred for 2 hours at moderate speed (to ensure complete dissolution of the PEG 3350).
6. The pH was adjusted using pH adjusting agents (HCl and NaOH) to 7.0±0.2.
7. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 3

Moxifloxacin Hydrochloride and Triamcinolone Acetonide Ophthalmic Suspension (Single Dose)

The composition having Formulation III was manufactured according to the following process.

Part I:
1. The total quantity of triamcinolone acetonide was added to 30% of the total required volume of water forming a triamcinolone acetonide suspension.
2. The triamcinolone acetonide suspension was passed through a homogenizer to form a suspension of particles having a D50 particle size of 0.5-1.5 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate in the sodium citrate monohydrate and polysorbate-80 solution, the complete quantity of moxifloxacin hydrochloride was added and stirred until completely dissolved.
5. Upon complete dissolution of moxifloxacin hydrochloride, the total quantity of CMC was added to the completely dissolved solution of sodium citrate monohydrate, polysorbate-80, disodium edetate dihydrate and moxifloxacin hydrochloride and stirred for 2 hours at moderate speed (to ensure complete dissolution of the CMC).
6. The pH was adjusted using pH adjusting agents (HCl and NaOH) to 7.0±0.2.
7. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 4

Moxifloxacin Hydrochloride and Triamcinolone Acetonide Ophthalmic Suspension (Single Dose)

The composition having Formulation IV was manufactured according to the following process.

Part I:
1. The total quantity of triamcinolone acetonide was added to 30% of the total required volume of water forming a triamcinolone acetonide suspension.
2. The triamcinolone acetonide suspension was passed through a homogenizer to form a suspension of particles having a D50 particle size of 0.5-1.5 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 50% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.

4. Upon complete dissolution of the disodium edetate dihydrate in the sodium citrate monohydrate and polysorbate-80 solution, the complete quantity of hyaluronic acid was added, and the mixture was stirred for 2 hours at moderate speed (to ensure complete dissolution of the hyaluronic acid).
5. Upon complete dissolution of the hyaluronic acid, the total quantity of chondroitin sulfate was added and the solution of sodium citrate monohydrate, polysorbate-80, disodium edetate dihydrate, and hyaluronic acid, and stirred for 2 hours at moderate speed (to ensure complete dissolution of the chondroitin sulfate).
6. Upon complete dissolution of the chondroitin sulfate, the resulting solution was autoclaved at 121° C. for 20 min.
7. The solution was allowed to cool to room temperature.
8. The total required quantity of moxifloxacin hydrochloride was added to the cooled solution and stirred until completely dissolved.
9. The solution was QS to 65% of the final volume.
10. The pH was adjusted using pH adjusting agents (HCl and NaOH) to 7.0±0.2.

Part III
1. Part II (i.e., the Part II composition, described above) was sterile filtered into Part I (i.e., the Part I composition, described above) through a 0.2 µm filter.
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 5

Moxifloxacin Hydrochloride and Triamcinolone Acetonide Ophthalmic Suspension (Multi-Dose)

The composition having Formulation V was manufactured according to the following process.

Part I:
1. The total quantity of triamcinolone acetonide was added to 30% of the total required volume of water forming a triamcinolone acetonide suspension.
2. The triamcinolone acetonide suspension was passed through a homogenizer to form a suspension of particles having a D50 particle size of 0.5-1.5 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 50% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate in the sodium citrate monohydrate and polysorbate-80 solution, the complete quantity of hyaluronic acid was added, and the mixture was stirred for 2 hours at moderate speed (to ensure complete dissolution of the hyaluronic acid).
5. Upon complete dissolution of the hyaluronic acid, the total quantity of chondroitin sulfate was added and the solution of sodium citrate monohydrate, polysorbate-80, disodium edetate dihydrate, and hyaluronic acid, and stirred for 2 hours at moderate speed (to ensure complete dissolution of the chondroitin sulfate).
6. Upon complete dissolution of the chondroitin sulfate, the resulting solution was autoclaved at 121° C. for 20 min.
7. The solution was allowed to cool to room temperature.
8. The total required quantity of moxifloxacin hydrochloride and total required quantity of benzalkonium chloride were added to the cooled solution and stirred until completely dissolved.
9. The solution was QS to 65% of the final volume.
10. The pH was adjusted using pH adjusting agents (HCl and NaOH) to 7.0±0.2.

Part III
1. Part II (i.e., the Part II composition, described above) was sterile filtered into Part I (i.e., the Part I composition, described above) through a 0.2 µm filter.
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

EXAMPLES
(PREDNISOLONE+MOXIFLOXACIN)

The following ophthalmologically suitable antimicrobial-anti-inflammatory combination formulations of Table 3 were generated according to the following procedures.

TABLE 3

Exemplary Formulations.

| | QUANTITY/mL (mg) | | | |
|---|---|---|---|---|
| INGREDIENT | Form. I | Form. II | Form. III | Form. IV |
| Prednisolone acetate (as base) | 10.0-15.0 | 10.0-15.0 | 10.0-15.0 | 10.0-15.0 |
| Moxifloxacin HCl (as base) | 1.0 | 1.0 | 1.0 | 1.0 |
| Polysorbate-80 | 10.0 | 10.0 | 10.0 | 10.0 |
| Hyaluronic acid | 2.0-20.0 | 2.0-20.0 | 2.0-20.0 | 2.0-20.0 |
| Chondroitin sulfate | — | — | 5.0-50.0 | 5.0-50.0 |
| Sodium citrate monohydrate | 1.0-10.0 | 1.0-10.0 | 1.0-10.0 | 1.0-10.0 |
| Disodium edetate dihydrate | 1.0-5.0 | 1.0-5.0 | 1.0-5.0 | 1.0-5.0 |
| Benzalkonium chloride | — | 0.05 | — | 0.05 |

TABLE 3-continued

Exemplary Formulations.

| INGREDIENT | QUANTITY/mL (mg) | | | |
|---|---|---|---|---|
| | Form. I | Form. II | Form. III | Form. IV |
| Hydrochloric acid/ sodium hydroxide | QS to adjust pH to 7.0 ± 0.2 | QS to adjust pH to 7.0 ± 0.2 | QS to adjust pH to 7.0 ± 0.2 | QS to adjust pH to 7.0 ± 0.2 |
| Water | QS to 1.0 mL | QS to 1.0 mL | QS to 1.0 mL | QS to 1.0 mL |

("Form." = formulation)

Example 1

Moxifloxacin Hydrochloride and Prednisolone Acetate Ophthalmic Suspension (Single Dose)

The composition having Formulation I was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of moxifloxacin was added and completely dissolved.
5. Upon completion of the dissolution of moxifloxacin, the total quantity of hyaluronic acid was added to the completely dissolved solution of sodium citrate monohydrate, polysorbate-80, disodium edetate dihydrate, and moxifloxacin and stirred for 2 hours at moderate speed (to ensure complete dissolution of the hyaluronic acid).
6. The pH was adjusted using pH adjusting agents (HCl and NaOH) to 7.0±0.2.
7. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 2

Moxifloxacin Hydrochloride and Prednisolone Acetate Ophthalmic Suspension (Multi Dose)

The composition having Formulation II was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and completely dissolved.
5. Upon complete dissolution of the benzalkonium in the sodium citrate monohydrate, polysorbate-80 solution, and disodium edetate solution, the complete quantity of moxifloxacin hydrochloride was added and stirred until completely dissolved.
6. Upon complete dissolution of moxifloxacin hydrochloride, the total quantity of hyaluronic acid was added to the completely dissolved solution of sodium citrate monohydrate, polysorbate-80, disodium edetate dihydrate and moxifloxacin hydrochloride and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 3

Moxifloxacin Hydrochloride and Prednisolone Acetate Ophthalmic Suspension (Single Dose)

The composition having Formulation III was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate in the sodium citrate monohydrate and polysorbate-80 solution, the complete quantity of moxifloxacin hydrochloride was added and stirred until completely dissolved.
5. Upon complete dissolution of moxifloxacin hydrochloride, the total quantity of hyaluronic acid was added to the completely dissolved solution of sodium citrate monohydrate, polysorbate-80, disodium edetate dihydrate and moxifloxacin hydrochloride and stirred for 2 hours at moderate speed (to ensure complete dissolution of the hyaluronic acid).
6. Upon complete dissolution of the hyaluronic acid, the total quantity of chondroitin sulfate was added and completely dissolved.
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 µm filter.
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 4

Moxifloxacin Hydrochloride and Prednisolone Acetate Ophthalmic Suspension (Multi Dose)

The composition having Formulation IV was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and allowed to completely dissolve.
5. Upon complete dissolution of the benzalkonium chloride, the total quantity of moxifloxacin was added and allowed to completely dissolve.
6. Upon complete dissolution of the moxifloxacin in the sodium citrate monohydrate, polysorbate-80 solution, disodium edetate dihydrate, and benzalkonium chloride solution, the complete quantity of hyaluronic acid was added, and the mixture was stirred for 2 hours at moderate speed (to ensure complete dissolution of the hyaluronic acid).
7. Upon complete dissolution of the hyaluronic acid, the total quantity of chondroitin sulfate was added and the solution of sodium citrate monohydrate, polysorbate-80, disodium edetate dihydrate, benzalkonium, and moxifloxacin solution and allowed to completely dissolve.
8. The pH was adjusted using pH adjusting agents (HCl and NaOH) to 7.0±0.2.
9. The solution was QS to 65% of the final volume.

Part III
1. Part II (i.e., the Part II composition, described above) was sterile filtered into Part I (i.e., the Part I composition, described above) through a 0.2 µm filter.
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

EXAMPLES
(LOTEPREDNOL+MOXIFLOXACIN)

The following ophthalmologically suitable antimicrobial-anti-inflammatory combination formulations of Table 4 were generated according to the following procedures.

TABLE 4

Exemplary Formulations.

| INGREDIENT | QUANTITY/mL (mg) | | | |
|---|---|---|---|---|
| | Form. I | Form. II | Form. III | Form. IV |
| Loteprednol etabonate (as base) | 10.0-15.0 | 10.0-15.0 | 10.0-15.0 | 10.0-15.0 |
| Moxifloxacin HCl (as base) | 1.0 | 1.0 | 1.0 | 1.0 |
| Polysorbate-80 | 10.0 | 10.0 | 10.0 | 10.0 |
| Hyaluronic acid | 2.0-20.0 | 2.0-20.0 | 2.0-20.0 | 2.0-20.0 |
| Chondroitin sulfate | — | — | 5.0-50.0 | 5.0-50.0 |
| Sodium citrate monohydrate | 1.0-10.0 | 1.0-10.0 | 1.0-10.0 | 1.0-10.0 |
| Disodium edetate dihydrate | 1.0-5.0 | 1.0-5.0 | 1.0-5.0 | 1.0-5.0 |
| Benzalkonium chloride | — | 0.05 | — | 0.05 |
| Hydrochloric acid/ sodium hydroxide | QS to adjust pH to 7.0 ± 0.2 | QS to adjust pH to 7.0 ± 0.2 | QS to adjust pH to 7.0 ± 0.2 | QS to adjust pH to 7.0 ± 0.2 |
| Water | QS to 1.0 mL | QS to 1.0 mL | QS to 1.0 mL | QS to 1.0 mL |

("Form." = formulation)

Example 1

Moxifloxacin Hydrochloride and Loteprednol Etabonate Ophthalmic Suspension (Single Dose)

The composition having Formulation I was manufactured according to the following process.
Part I:
1. The total quantity of loteprednol etabonate was added to 30% of the total required volume of water forming a loteprednol etabonate suspension.
2. The loteprednol etabonate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.
Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of moxifloxacin was added and completely dissolved.
5. Upon completion of the dissolution of moxifloxacin, the total quantity of hyaluronic acid was added to the completely dissolved solution of sodium citrate monohydrate, polysorbate-80, disodium edetate dihydrate, and moxifloxacin and stirred for 2 hours at moderate speed (to ensure complete dissolution of the hyaluronic acid).
6. The pH was adjusted using pH adjusting agents (HCl and NaOH) to 7.0±0.2.
7. The resulting solution was QS to 65% of the final volume.
Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 2

Moxifloxacin Hydrochloride and Loteprednol Etabonate Ophthalmic Suspension (Multi Dose)

The composition having Formulation II was manufactured according to the following process.
Part I:
1. The total quantity of loteprednol etabonate was added to 30% of the total required volume of water forming a loteprednol etabonate suspension.
2. The loteprednol etabonate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.
Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and completely dissolved.
5. Upon complete dissolution of the benzalkonium in the sodium citrate monohydrate, polysorbate-80 solution, and disodium edetate solution, the complete quantity of moxifloxacin hydrochloride was added and stirred until completely dissolved.
6. Upon complete dissolution of moxifloxacin hydrochloride, the total quantity of hyaluronic acid was added to the completely dissolved solution of sodium citrate monohydrate, polysorbate-80, disodium edetate dihydrate and moxifloxacin hydrochloride and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 3

Moxifloxacin Hydrochloride and Loteprednol Etabonate Ophthalmic Suspension (Single Dose)

The composition having Formulation III was manufactured according to the following process.

Part I:
1. The total quantity of loteprednol etabonate was added to 30% of the total required volume of water forming a loteprednol etabonate suspension.
2. The loteprednol etabonate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate in the sodium citrate monohydrate and polysorbate-80 solution, the complete quantity of moxifloxacin hydrochloride was added and stirred until completely dissolved.
5. Upon complete dissolution of moxifloxacin hydrochloride, the total quantity of hyaluronic acid was added to the completely dissolved solution of sodium citrate monohydrate, polysorbate-80, disodium edetate dihydrate and moxifloxacin hydrochloride and stirred for 2 hours at moderate speed (to ensure complete dissolution of the hyaluronic acid).
6. Upon complete dissolution of the hyaluronic acid, the total quantity of chondroitin sulfate was added and completely dissolved.
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 4

Moxifloxacin Hydrochloride and Loteprednol Etabonate Ophthalmic Suspension (Multi Dose)

The composition having Formulation IV was manufactured according to the following process.

Part I:
1. The total quantity of loteprednol etabonate was added to 30% of the total required volume of water forming a loteprednol etabonate suspension.
2. The loteprednol etabonate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and allowed to completely dissolve.
5. Upon complete dissolution of the benzalkonium chloride, the total quantity of moxifloxacin was added and allowed to completely dissolve.
6. Upon complete dissolution of the moxifloxacin in the sodium citrate monohydrate, polysorbate-80 solution, disodium edetate dihydrate, and benzalkonium chloride solution, the complete quantity of hyaluronic acid was added, and the mixture was stirred for 2 hours at moderate speed (to ensure complete dissolution of the hyaluronic acid).
7. Upon complete dissolution of the hyaluronic acid, the total quantity of chondroitin sulfate was added and the solution of sodium citrate monohydrate, polysorbate-80, disodium edetate dihydrate, benzalkonium, and moxifloxacin solution and allowed to completely dissolve.
8. The pH was adjusted using pH adjusting agents (HCl and NaOH) to 7.0±0.2.
9. The solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Examples (Gatifloxacin+Prednisolone+Bromfenac)

The following ophthalmologically suitable antimicrobial-anti-inflammatory combination formulations of Table 5 were generated according to the following procedures.

Example 1

Gatifloxacin, Prednisolone Acetate, and Bromfenac Sodium Sesquihydrate Ophthalmic Suspension (Single Dose)

The composition having Formulation I was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of gatifloxacin was added and completely dissolved.
5. Upon complete dissolution of the gatifloxacin, the total quantity of bromfenac sodium sesquihydrate was added and completely dissolved.
6. Upon completion of the dissolution of bromfenac sodium sesquihydrate, the total quantity of hyaluronic

TABLE 5

Exemplary Formulations.

| INGREDIENT | QUANTITY/mL (mg) | | | | | |
|---|---|---|---|---|---|---|
| | Form. I | Form. II | Form. III | Form. IV | Form. V | Form. VI |
| Prednisolone acetate (as base) | 10.0-15.0 | 10.0-15.0 | 10.0-15.0 | 10.0-15.0 | 10.0-15.0 | 10.0-15.0 |
| Gatifloxacin (as base) | 5.0 | 5.0 | 5.0 | 5.0 | 5.0 | 5.0 |
| Bromfenac sodium sesquihydrate | 1.04 | 1.04 | 1.04 | 1.04 | 1.04 | 1.04 |
| Polysorbate-80 | 10.0 | 10.0 | 10.0 | 10.0 | — | — |
| Hyaluronic acid | 2.0-20.0 | 2.0-20.0 | 2.0-20.0 | 2.0-20.0 | 2.0-20.0 | 2.0-20.0 |
| Chondroitin sulfate | — | — | 5.0-50.0 | 5.0-50.0 | — | — |
| Sodium citrate monohydrate | 1.0-10.0 | 1.0-10.0 | 1.0-10.0 | 1.0-10.0 | 1.0-10.0 | 1.0-10.0 |
| Disodium edetate dihydrate | 1.0-5.0 | 1.0-5.0 | 1.0-5.0 | 1.0-5.0 | 1.0-5.0 | 1.0-5.0 |
| Benzalkonium chloride | — | 0.05 | — | 0.05 | 0.05 | 0.05 |
| Hydrochloric acid/ sodium hydroxide | QS to adjust pH to 7.0 ± 0.2 | QS to adjust pH to 7.0 ± 0.2 | QS to adjust pH to 7.0 ± 0.2 | QS to adjust pH to 7.0 ± 0.2 | QS to adjust pH to 7.0 ± 0.2 | QS to adjust pH to 7.0 ± 0.2 |
| Water | QS to 1.0 mL | QS to 1.0 mL | QS to 1.0 mL | QS to 1.0 mL | QS to 1.0 mL | QS to 1.0 mL |

("Form." = formulation)

acid was added to the completely dissolved solution of sodium citrate monohydrate, polysorbate-80, disodium edetate dihydrate, gatifloxacin, and bromfenac sodium sesquihydrate, and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 2

Gatifloxacin, Prednisolone Acetate, and Bromfenac Sodium Sesquihydrate Ophthalmic Suspension (Multi-Dose)

The composition having Formulation II was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and completely dissolved.
5. Upon complete dissolution of the benzalkonium in the sodium citrate monohydrate, polysorbate-80 solution, and disodium edetate solution, the total quantity of gatifloxacin was added and allowed to completely dissolve.
6. Upon the complete dissolution of the gatifloxacin, the total quantity of bromfenac sodium sesquihydrate was added and allowed to completely dissolve.
7. Upon complete dissolution of bromfenac sodium sesquihydrate, the total quantity of hyaluronic acid was added to the completely dissolved solution of sodium citrate monohydrate, polysorbate-80, disodium edetate dihydrate, gatifloxacin, and bromfenac sodium sesquihydrate and stirred for 2 hours at moderate speed (to ensure complete dissolution of the hyaluronic acid).
8. The pH was adjusted using pH adjusting agents (HCl and NaOH) to 7.0±0.2.
9. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 3

Gatifloxacin, Prednisolone Acetate, and Bromfenac Sodium Sesquihydrate Ophthalmic Suspension (Single Dose)

The composition having Formulation III was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate in the sodium citrate monohydrate and polysorbate-80 solution, the complete quantity of gatifloxacin was added and stirred until completely dissolved.
5. Upon complete dissolution of moxifloxacin hydrochloride, the total quantity of hyaluronic acid was added to the completely dissolved solution of sodium citrate monohydrate, polysorbate-80, disodium edetate dihydrate and gatifloxacin and stirred for 2 hours at moderate speed (to ensure complete dissolution of the hyaluronic acid).
6. Upon complete dissolution of the hyaluronic acid, the total quantity of chondroitin sulfate was added and completely dissolved.
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Example 4

Gatifloxacin, Prednisolone Acetate, and Bromfenac Sodium Sesquihydrate Ophthalmic Suspension (Multi-Dose)

The composition having Formulation IV was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and allowed to completely dissolve.
5. Upon complete dissolution of the benzalkonium chloride, the total quantity of gatifloxacin was added and allowed to completely dissolve.
6. Upon the complete dissolution of gatifloxacin, the total quantity of bromfenac sodium sesquihydrate was added and allowed to completely dissolve.
7. Upon complete dissolution of the bromfenac sodium sesquihydrate in the sodium citrate monohydrate, polysorbate-80 solution, disodium edetate dihydrate, benzalkonium chloride, and gatifloxacin solution, the complete quantity of hyaluronic acid was added, and the mixture was stirred for 2 hours at moderate speed (to ensure complete dissolution of the hyaluronic acid).
8. Upon complete dissolution of the hyaluronic acid, the total quantity of chondroitin sulfate was added and the solution of sodium citrate monohydrate, polysorbate-80, disodium edetate dihydrate, benzalkonium, and moxifloxacin solution and allowed to completely dissolve.
9. The pH was adjusted using pH adjusting agents (HCl and NaOH) to 7.0±0.2.
10. The solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 5

Gatifloxacin, Prednisolone Acetate, and Bromfenac Sodium Sesquihydrate Ophthalmic Suspension (Single Dose)

The composition having Formulation V was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of disodium edetate dihydrate was added to the completely dissolved solution of sodium citrate monohydrate and completely dissolved.
3. Upon complete dissolution of the disodium edetate dihydrate, the total quantity of benzalkonium chloride was added and completely dissolved.
4. Upon complete dissolution of the benzalkonium in the sodium citrate monohydrate and disodium edetate solution, the total quantity of gatifloxacin was added and allowed to completely dissolve.
5. Upon the complete dissolution of the gatifloxacin, the total quantity of bromfenac sodium sesquihydrate was added and allowed to completely dissolve.
6. Upon complete dissolution of bromfenac sodium sesquihydrate, the total quantity of hyaluronic acid was added to the completely dissolved solution of sodium citrate monohydrate, disodium edetate dihydrate, gatifloxacin, and bromfenac sodium sesquihydrate and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 6

Gatifloxacin, Prednisolone Acetate, and Bromfenac Sodium Sesquihydrate Ophthalmic Suspension (Multi Dose)

The composition having Formulation V was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of disodium edetate dihydrate was added to the completely dissolved solution of sodium citrate monohydrate and completely dissolved.
3. Upon complete dissolution of the disodium edetate dihydrate, the total quantity of benzalkonium chloride was added and completely dissolved.
4. Upon complete dissolution of the benzalkonium in the sodium citrate monohydrate and disodium edetate solution, the total quantity of gatifloxacin was added and allowed to completely dissolve.
5. Upon the complete dissolution of the gatifloxacin, the total quantity of bromfenac sodium sesquihydrate was added and allowed to completely dissolve.
6. Upon complete dissolution of bromfenac sodium sesquihydrate, the total quantity of hyaluronic acid was added to the completely dissolved solution of sodium citrate monohydrate, disodium edetate dihydrate, gatifloxacin, and bromfenac sodium sesquihydrate and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Examples (Moxifloxacin+Prednisolone+Bromfenac)

The following ophthalmologically suitable antimicrobial-anti-inflammatory combination formulations of Table 6 were generated according to the following procedures.

TABLE 6

Exemplary Formulations.

| INGREDIENT | QUANTITY/mL (mg) | | | | | |
|---|---|---|---|---|---|---|
| | Form. I | Form. II | Form. III | Form. IV | Form. V | Form. VI |
| Prednisolone acetate (as base) | 10.0-15.0 | 10.0-15.0 | 10.0-15.0 | 10.0-15.0 | 10.0-15.0 | 10.0-15.0 |
| Moxifloxacin hydrochloride (as base) | 5.0 | 5.0 | 5.0 | 5.0 | 5.0 | 5.0 |
| Bromfenac sodium sesquihydrate | 1.04 | 1.04 | 1.04 | 1.04 | 1.04 | 1.04 |
| Polysorbate-80 | 10.0 | 10.0 | 10.0 | 10.0 | — | — |
| Hyaluronic acid | 2.0-20.0 | 2.0-20.0 | 2.0-20.0 | 2.0-20.0 | 2.0-20.0 | 2.0-20.0 |
| Chondroitin sulfate | — | — | 5.0-50.0 | 5.0-50.0 | — | — |
| Sodium citrate monohydrate | 1.0-10.0 | 1.0-10.0 | 1.0-10.0 | 1.0-10.0 | 1.0-10.0 | 1.0-10.0 |

TABLE 6-continued

Exemplary Formulations.

| INGREDIENT | QUANTITY/mL (mg) | | | | | |
|---|---|---|---|---|---|---|
| | Form. I | Form. II | Form. III | Form. IV | Form. V | Form. VI |
| Disodium edetate dihydrate | 1.0-5.0 | 1.0-5.0 | 1.0-5.0 | 1.0-5.0 | 1.0-5.0 | 1.0-5.0 |
| Benzalkonium chloride | — | 0.05 | — | 0.05 | 0.05 | 0.05 |
| Hydrochloric acid/ sodium hydroxide | QS to adjust pH to 7.0 ± 0.2 | QS to adjust pH to 7.0 ± 0.2 | QS to adjust pH to 7.0 ± 0.2 | QS to adjust pH to 7.0 ± 0.2 | QS to adjust pH to 7.0 ± 0.2 | QS to adjust pH to 7.0 ± 0.2 |
| Water | QS to 1.0 mL | QS to 1.0 mL | QS to 1.0 mL | QS to 1.0 mL | QS to 1.0 mL | QS to 1.0 mL |

("Form." = formulation)

Example 1

Moxifloxacin hydrochloride, prednisolone acetate, and bromfenac sodium sesquihydrate ophthalmic suspension (single dose)

The composition having Formulation I was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of moxifloxacin hydrochloride was added and completely dissolved.
5. Upon complete dissolution of the moxifloxacin hydrochloride, the total quantity of bromfenac sodium sesquihydrate was added and completely dissolved.
6. Upon completion of the dissolution of bromfenac sodium sesquihydrate, the total quantity of hyaluronic acid was added to the completely dissolved solution of sodium citrate monohydrate, polysorbate-80, disodium edetate dihydrate, moxifloxacin hydrochloride, and bromfenac sodium sesquihydrate, and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 2

Moxifloxacin Hydrochloride, Prednisolone Acetate, and Bromfenac Sodium Sesquihydrate Ophthalmic Suspension (Multi-Dose)

The composition having Formulation II was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 μm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.
4. Upon complete dissolution of the disodium edetate dihydrate, the total quantity of benzalkonium chloride was added and completely dissolved.

5. Upon complete dissolution of the benzalkonium in the sodium citrate monohydrate, polysorbate-80 solution, and disodium edetate solution, the total quantity of moxifloxacin hydrochloride was added and allowed to completely dissolve.
6. Upon the complete dissolution of the moxifloxacin hydrochloride, the total quantity of bromfenac sodium sesquihydrate was added and allowed to completely dissolve.
7. Upon complete dissolution of bromfenac sodium sesquihydrate, the total quantity of hyaluronic acid was added to the completely dissolved solution of sodium citrate monohydrate, polysorbate-80, disodium edetate dihydrate, moxifloxacin hydrochloride, and bromfenac sodium sesquihydrate and stirred for 2 hours at moderate speed (to ensure complete dissolution of the hyaluronic acid).
8. The pH was adjusted using pH adjusting agents (HCl and NaOH) to 7.0±0.2.
9. The resulting solution was QS to 65% of the final volume.

Part III
1. Part II (above) was sterile filtered into Part I (above) through a 0.2 µm filter
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 3

Moxifloxacin Hydrochloride, Prednisolone Acetate, and Bromfenac Sodium Sesquihydrate Ophthalmic Suspension (Single Dose)

The composition having Formulation III was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.

4. Upon complete dissolution of the disodium edetate dihydrate in the sodium citrate monohydrate and polysorbate-80 solution, the complete quantity of moxifloxacin hydrochloride was added and stirred until completely dissolved.
5. Upon complete dissolution of moxifloxacin hydrochloride, the total quantity of hyaluronic acid was added to the completely dissolved solution of sodium citrate monohydrate, polysorbate-80, disodium edetate dihydrate and moxifloxacin hydrochloride and stirred for 2 hours at moderate speed (to ensure complete dissolution of the hyaluronic acid).
6. Upon complete dissolution of the hyaluronic acid, the total quantity of chondroitin sulfate was added and completely dissolved.
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 µm filter.
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 4

Moxifloxacin Hydrochloride, Prednisolone Acetate, and Bromfenac Sodium Sesquihydrate Ophthalmic Suspension (Multi-Dose)

The composition having Formulation IV was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of polysorbate-80 was added to the completely dissolved solution of sodium citrate monohydrate and completely dissolved.
3. Upon complete dissolution of the polysorbate-80, disodium edetate dihydrate was added to the completely dissolved solution of sodium citrate monohydrate and polysorbate-80 and completely dissolved.

4. Upon complete dissolution of the disodium edetate dihydrate, the total quantity of benzalkonium chloride was added and allowed to completely dissolve.
5. Upon complete dissolution of the benzalkonium chloride, the total quantity of gatifloxacin was added and allowed to completely dissolve.
6. Upon the complete dissolution of moxifloxacin hydrochloride, the total quantity of bromfenac sodium sesquihydrate was added and allowed to completely dissolve.
7. Upon complete dissolution of the bromfenac sodium sesquihydrate in the sodium citrate monohydrate, polysorbate-80 solution, disodium edetate dihydrate, benzalkonium chloride, and moxifloxacin hydrochloride solution, the complete quantity of hyaluronic acid was added, and the mixture was stirred for 2 hours at moderate speed (to ensure complete dissolution of the hyaluronic acid).
8. Upon complete dissolution of the hyaluronic acid, the total quantity of chondroitin sulfate was added and the solution of sodium citrate monohydrate, polysorbate-80, disodium edetate dihydrate, benzalkonium, and moxifloxacin solution and allowed to completely dissolve.
9. The pH was adjusted using pH adjusting agents (HCl and NaOH) to 7.0±0.2.
10. The solution was QS to 65% of the final volume.

Part III
1. Part II (above) was sterile filtered into Part I (above) through a 0.2 µm filter
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 5

Moxifloxacin Hydrochloride, Prednisolone Acetate, and Bromfenac Sodium Sesquihydrate Ophthalmic Suspension (Single Dose)

The composition having Formulation V was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of disodium edetate dihydrate was added to the completely dissolved solution of sodium citrate monohydrate and completely dissolved.
3. Upon complete dissolution of the disodium edetate dihydrate, the total quantity of benzalkonium chloride was added and completely dissolved.
4. Upon complete dissolution of the benzalkonium in the sodium citrate monohydrate and disodium edetate solution, the total quantity of moxifloxacin hydrochloride was added and allowed to completely dissolve.
5. Upon the complete dissolution of the moxifloxacin hydrochloride, the total quantity of bromfenac sodium sesquihydrate was added and allowed to completely dissolve.
6. Upon complete dissolution of bromfenac sodium sesquihydrate, the total quantity of hyaluronic acid was added to the completely dissolved solution of sodium citrate monohydrate, disodium edetate dihydrate, moxifloxacin hydrochloride, and bromfenac sodium sesquihydrate and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III
1. Part II (i.e., the Part II composition, described above) was sterile filtered into Part I (i.e., the Part I composition, described above) through a 0.2 µm filter.
2. The remaining 5% of the total volume of water was used to rinse the container of Part II and this was passed through the same 0.2 µm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

Example 6

Moxifloxacin, Prednisolone Acetate, and Bromfenac Sodium Sesquihydrate Ophthalmic Suspension (Multi Dose)

The composition having Formulation V was manufactured according to the following process.

Part I:
1. The total quantity of prednisolone acetate was added to 30% of the total required volume of water forming a prednisolone acetate suspension.
2. The prednisolone acetate suspension was passed through a homogenizer to form a suspension of particles having a D50 particle size of 2-3 µm.
3. The resulting suspension was sterilized by autoclaving at 121° C. for 30 min.
4. The sterilized solution was constantly stirred while being allowed to cool.

Part II:
1. The total quantity of sodium citrate monohydrate was completely dissolved in 55% of the total required water.
2. Upon complete dissolution of the sodium citrate monohydrate, the total quantity of disodium edetate dihydrate was added to the completely dissolved solution of sodium citrate monohydrate and completely dissolved.

3. Upon complete dissolution of the disodium edetate dihydrate, the total quantity of benzalkonium chloride was added and completely dissolved.
4. Upon complete dissolution of the benzalkonium in the sodium citrate monohydrate and disodium edetate solution, the total quantity of moxifloxacin hydrochloride was added and allowed to completely dissolve.
5. Upon the complete dissolution of the moxifloxacin hydrochloride, the total quantity of bromfenac sodium sesquihydrate was added and allowed to completely dissolve.
6. Upon complete dissolution of bromfenac sodium sesquihydrate, the total quantity of hyaluronic acid was added to the completely dissolved solution of sodium citrate monohydrate, disodium edetate dihydrate, moxifloxacin hydrochloride, and bromfenac sodium sesquihydrate and stirred for 2 hours at moderate speed (to ensure complete dissolution of the hyaluronic acid).
7. The pH was adjusted using pH adjusting agents (HCl and NaOH) to 7.0±0.2.
8. The resulting solution was QS to 65% of the final volume.

Part III

1. Part II (i.e., the Part II composition, described above) was sterile filtered into Part I (i.e., the Part I composition, described above) through a 0.2 μm filter.
2. The remaining 5% of the total volume of water was used to rinse the container of Part II and this was passed through the same 0.2 μm filter.
3. The final solution was QS to a final volume with additional sterile-filtered water for injection (WFI).

Composition(s) exemplified in this Example are expected to be stable over relevant periods of storage under typical conditions and to be ophthalmologically suitable and when provided in therapeutically effective amounts over a suitable treatment protocol effective at treating one or more bacterial conditions.

The invention claimed is:

1. An ophthalmologically suitable pharmaceutical composition in the form of a suspension comprising:
   (a) an effective amount of at least one ionic suspension agent;
   (b) an effective amount of at least one non-ionic suspension agent;
   (c) at least three pharmaceutical ingredients comprising (1) gatifloxacin or a pharmaceutically acceptable salt thereof in a range of about 0.01% to about 1% by weight, (2) prednisolone or a pharmaceutically acceptable salt thereof in a range of about 0.1% to about 5% by weight, and (3) bromfenac or a pharmaceutically acceptable salt thereof in a range of about 0.01%-to about 1% by weight; and
   (d) an effective amount of a pharmaceutically acceptable chelating agent; wherein the composition is free of an effective amount of any non-ionic polyoxyethylene-polyoxypropylene block copolymer having the following chemical structure —HO—(CH2-CH2-O)x-(C3H6-O)y-(CH2-CH2-O)x-H, wherein x is an integer having a value of at least 8 and y is an integer having a value of at least 38, wherein the at least one ionic suspension agent is mostly composed of a hyaluronic acid component with an average molecular weight of about 360 kDa to about 1200 kDa.

2. The composition of claim 1, wherein one or more of the at least one ionic suspension agents in the composition is not capable of significantly increasing the solubilization of any of the at least three pharmaceutical ingredients.

3. The composition of claim 2, wherein the composition comprises only a single ionic suspension agent.

4. The composition of claim 3, wherein one or more of the at least one non-ionic suspension agents is also a non-ionic surfactant.

5. The composition of claim 4, wherein the non-ionic surfactant comprises an effective amount of a polysorbate, a polyoxyl-ethylated castor oil, or a combination thereof.

6. The composition of claim 1, wherein the ratio of gatifloxacin or a pharmaceutically acceptable salt thereof to the combination of the at least one ionic suspension agent and the at least one non-ionic suspension agent is about 1:2 to about 1:10.

7. The composition of claim 1, wherein the ratio of the at least one ionic suspension agent to the at least one non-ionic suspension agent is about 1:8 to about 4:1.

8. The composition of claim 1, wherein the pharmaceutically acceptable chelating agent is disodium edetate in a concentration of about 0.1 mg/mL to about 0.5 mg/mL.

9. The composition of claim 1, wherein the composition comprises hyaluronic acid in a concentration of about 2 mg/mL to about 20 mg/mL.

10. The composition of claim 9, wherein the composition further comprises chondroitin sulfate in a concentration is about 5 mg/mL to about 50 mg/mL.

11. The composition of claim 1, wherein (a) the concentration of gatifloxacin or a pharmaceutically acceptable salt thereof is about 0.5% by weight, (b) the concentration of prednisolone or a pharmaceutically acceptable salt thereof is about 1.5% by weight, (c) the concentration of bromfenac or a pharmaceutically acceptable salt thereof is about 0.09% by weight, or (d) the concentration of gatifloxacin or a pharmaceutically acceptable salt thereof is about 0.5% by weight, the concentration of prednisolone or a pharmaceutically acceptable salt thereof is about 1.5% by weight, and the concentration of bromfenac or a pharmaceutically acceptable salt thereof is about 0.09% by weight.

12. The composition of claim 1, wherein the osmolality of the composition is about 200 mOsm/kg to about 350 mOsm/kg.

13. The composition of claim 5, wherein the non-ionic surfactant comprises an effective amount of polysorbate 80.

14. The composition of claim 13, wherein polysorbate 80 is present in the composition in a concentration of about 5 mg/mL to about 15 mg/mL.

15. The composition of claim 1, wherein the pharmaceutically acceptable chelating agent is a chelating agent which results in a significantly similar or improved stability of the gatifloxacin or pharmaceutically acceptable salt thereof, prednisolone or pharmaceutically acceptable salt thereof, or bromfenac or pharmaceutically acceptable salt thereof as compared to disodium edetate in a concentration of about 0.1 mg/mL to about 0.5 mg/mL.

16. The composition of claim 1, wherein the composition is formulated for topical administration and is contained in a device adapted for delivery by drops to the eye.

17. A method of treating or preventing an ocular bacterial infection in a mammalian eye comprising administering to the mammalian eye an effective amount of an ophthalmologically suitable composition comprising:
   (a) an effective amount of at least one ionic suspension agent;
   (b) an effective amount of at least one non-ionic suspension agent;
   (c) at least three pharmaceutical ingredients comprising (1) gatifloxacin or a pharmaceutically acceptable salt thereof in a range of about 0.01% to about 1% by weight, (2) prednisolone or a pharmaceutically acceptable salt thereof in a range of about 0.1% to about 5% by weight, and (3) bromfenac or a pharmaceutically acceptable salt thereof in a range of about 0.01% to about 1% by weight; and (d) an effective amount of a pharmaceutically acceptable chelating agent, wherein the composition does not comprise any block copolymers of poly(ethylene oxide) and poly(propylene oxide), wherein the at least one ionic suspension agent is mostly composed of a hyaluronic acid component with an average molecular weight of about 360 kDa to about 1200 kDa.

18. The method of claim 17, wherein the composition comprises only a single ionic suspension agent.

19. The method of claim 17, wherein one or more of the at least one non-ionic suspension agents of the composition is also a non-ionic surfactant.

20. The method of claim 19, wherein a non-ionic surfactant of the composition comprises an effective amount of a polysorbate, a polyoxyl-ethylated castor oil, or a combination thereof.

21. The method of claim 17, wherein the ratio of gatifloxacin or a pharmaceutically acceptable salt thereof to the combination of the at least one ionic suspension agent and at least one non-ionic suspension agent is about 1:2 to about 1:10 and the ratio of the at least one ionic suspension agent to the at least one non-ionic suspension agent is about 1:8 to about 4:1.

22. The method of claim 17, wherein the composition comprises hyaluronic acid in a concentration of about 2 mg/mL to about 20 mg/mL.

23. The method of claim 17, wherein (a) the concentration of gatifloxacin or a pharmaceutically acceptable salt thereof in the composition is about 0.5% by weight; (b) the concentration of prednisolone or a pharmaceutically acceptable salt thereof in the composition is about 1.5% by weight; (c) the concentration of bromfenac or a pharmaceutically acceptable salt thereof in the composition is about 0.09% by weight; or (d) the concentration of gatifloxacin or a pharmaceutically acceptable salt thereof in the composition is about 0.5% by weight, the concentration of prednisolone or a pharmaceutically acceptable salt thereof in the composition is about 1.5% by weight, and the concentration of bromfenac or a pharmaceutically acceptable salt thereof in the composition is about 0.09% by weight.

24. The method of claim 19, wherein the non-ionic surfactant comprises polysorbate 80 in a concentration of about 5 mg/mL to about 15 mg/mL or a polyoxyl-ethylated castor oil in an amount of about 0.1% to about 1% by weight.

* * * * *

UNITED STATES PATENT AND TRADEMARK OFFICE
CERTIFICATE OF CORRECTION

| | |
|---|---|
| PATENT NO. | : 11,510,930 B2 |
| APPLICATION NO. | : 17/458529 |
| DATED | : November 29, 2022 |
| INVENTOR(S) | : Mandar V. Shah et al. |

It is certified that error appears in the above-identified patent and that said Letters Patent is hereby corrected as shown below:

In the Claims

At Column 144, Line numbers 23-25, Claim 10 should read "The composition of claim 9, wherein the composition further comprises chondroitin sulfate in a concentration of about 5 mg/mL to about 50 mg/mL."

Signed and Sealed this
Twenty-ninth Day of October, 2024

*Katherine Kelly Vidal*

Katherine Kelly Vidal
*Director of the United States Patent and Trademark Office*